(12) United States Patent
Ginn et al.

(10) Patent No.: US 9,079,880 B2
(45) Date of Patent: Jul. 14, 2015

(54) RHO KINASE INHIBITORS

(75) Inventors: John David Ginn, New Milford, CT (US); Daniel Richard Marshall, Norwalk, CT (US); Robert Sibley, North Haven, CT (US); Ronald John Sorcek, Bethel, CT (US); Erick Richard Roush Young, Danbury, CT (US); Yunlong Zhang, North Haven, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 255 days.

(21) Appl. No.: 13/171,701

(22) Filed: Jun. 29, 2011

(65) Prior Publication Data

US 2012/0178752 A1 Jul. 12, 2012

Related U.S. Application Data

(60) Provisional application No. 61/362,036, filed on Jul. 7, 2010.

(51) Int. Cl.
| | | |
|---|---|---|
| C07D 513/04 | (2006.01) | |
| A61K 31/381 | (2006.01) | |
| C07D 401/12 | (2006.01) | |
| C07D 207/09 | (2006.01) | |
| C07D 217/22 | (2006.01) | |
| C07D 277/60 | (2006.01) | |
| C07D 417/12 | (2006.01) | |
| C07D 417/14 | (2006.01) | |

(52) U.S. Cl.
CPC ............ *C07D 401/12* (2013.01); *C07D 207/09* (2013.01); *C07D 217/22* (2013.01); *C07D 277/60* (2013.01); *C07D 417/12* (2013.01); *C07D 417/14* (2013.01); *C07D 513/04* (2013.01)

(58) Field of Classification Search
CPC ........................... A61K 31/381; C07D 513/04
USPC ............................ 544/106; 546/114; 514/301
See application file for complete search history.

(56) References Cited

U.S. PATENT DOCUMENTS

| 8,093,266 B2 * | 1/2012 | Dahmann et al. ............. 514/310 |
|---|---|---|
| 2004/0082563 A1 | 4/2004 | Dorsch et al. |
| 2007/0173530 A1 | 7/2007 | deLong et al. |
| 2009/0270359 A1 | 10/2009 | Ito et al. |
| 2010/0041645 A1 | 2/2010 | Dahmann et al. |
| 2010/0227846 A1 | 9/2010 | Ito et al. |
| 2012/0165322 A1 | 6/2012 | Cook et al. |
| 2012/0178752 A1 | 7/2012 | Ginn et al. |
| 2012/0270868 A1 | 10/2012 | Kirrane et al. |

FOREIGN PATENT DOCUMENTS

| DE | 10112768 A1 | 9/2002 |
|---|---|---|
| EP | 1256574 A1 | 11/2002 |
| EP | 1403255 A1 | 3/2004 |
| JP | 11130751 A | 5/1999 |
| WO | 9205145 A1 | 4/1992 |
| WO | 9304682 A1 | 3/1993 |
| WO | 9304684 A1 | 3/1993 |
| WO | 0244126 A2 | 6/2002 |
| WO | 03015774 A1 | 2/2003 |
| WO | 2004071448 A2 | 8/2004 |
| WO | 2005051892 A1 | 6/2005 |
| WO | 2006034441 A1 | 3/2006 |
| WO | 2006052542 A2 | 5/2006 |
| WO | 2006129199 A1 | 12/2006 |
| WO | 2007008926 A1 | 1/2007 |
| WO | 2008053319 A1 | 5/2008 |
| WO | 2008083124 A1 | 7/2008 |
| WO | 2008086047 A1 | 7/2008 |
| WO | WO-2008086047 | * 7/2008 |
| WO | 2008157330 A1 | 12/2008 |
| WO | 2009027392 A1 | 3/2009 |
| WO | 2009028543 A1 | 3/2009 |

(Continued)

OTHER PUBLICATIONS

Chen, Jichou, et al; Synthesis of Carboxyphenoxyacetic Acid Derivatives Using Liquid-Liquid Phase Transfer Catalysis; Gaodeng Xuexiao Huaxue Xuebao (1991) vol. 12, No. 9 pp. 1195-1199.
Hoering, Heidi, et al; From Bench to Clinic and Back: Perspective on the 1st IQPC Translational Research Conference; Journal of Translational Medicine (2004) vol. 2, Chapter 44 pp. 1-8.
International Search Report and Written Opinion for PCT/US2008/050014 mailed May 8, 2008.
International Search Report and Written Opinion for PCT/US2011/042507 mailed Oct. 11, 2011.
International Search Report and Written Opinion for PCT/US2011/042508 mailed Oct. 12, 2011.

(Continued)

*Primary Examiner* — Yong Chu
*Assistant Examiner* — Sonya Wright
(74) *Attorney, Agent, or Firm* — Michael P. Morris; Edward S. Lazer

(57) ABSTRACT

The present invention relates to compounds of formula (I):

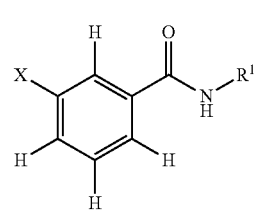

and pharmaceutically acceptable salts thereof, wherein $R^1$ and X are as defined herein. The invention also relates to pharmaceutical compositions comprising these compounds, methods of using these compounds in the treatment of various diseases and disorders, processes for preparing these compounds and intermediates useful in these processes.

11 Claims, No Drawings

(56) References Cited

FOREIGN PATENT DOCUMENTS

| WO | 2009065131 A1 | 5/2009 |
|---|---|---|
| WO | 2009119880 A1 | 10/2009 |
| WO | 2012006202 A1 | 1/2012 |
| WO | 2012006203 A1 | 1/2012 |
| WO | 2012054367 A1 | 4/2012 |

OTHER PUBLICATIONS

International Search Report and Written Opinion for PCT/US2011/056505 mailed Dec. 23, 2011.

Loirand, Gervaise, et al; Rho Kinases in Cardiovasculasr Physiology and Phathophysiology; Circulation Research (2006) vol. 98 pp. 322-334.

Lorthioir, Olivier, et al; Single Bead Characterization Using Analytical Constructs: Application to Quality Control of Libraries; Analytical Chemistry (2001) vol. 73 pp. 963-970.

Morwick, Tina, et al; Hit to Lead Account of the Discovery of Bisbenzamide and Related Ureidobenzamide inhibitors of Rho Kinase; Journal of Medicinal Chemistry (2010) vol. 53 pp. 759-777.

Schaefer, Stefan, et al; Failure is an Option: Learning From Unsuccessfull Proof-Of-Concept Trials; Drug Discovery Today (2008) vol. 13, No. 21/22 pp. 913-916.

Tawara, Shunsuke, et al; Progress of the Study of Rho-Kinase and Future Perspective of the Inhibitor; Yakugarku Zasshi (2007) vol. 127, No. 3 Abstract p. 501.

* cited by examiner

RHO KINASE INHIBITORS

FIELD OF THE INVENTION

This invention relates to substituted amide derivatives which are useful as inhibitors of Rho kinase and are thus useful for treating a variety of diseases and disorders that are mediated or sustained through the activity of Rho kinase, including cardiovascular diseases, cancer, neurological diseases, renal diseases, bronchial asthma, erectile dysfunction, and glaucoma. This invention also relates to pharmaceutical compositions comprising these compounds, methods of using these compounds in the treatment of various diseases and disorders, processes for preparing these compounds and intermediates useful in these processes.

BACKGROUND

Rho-Kinase (ROCK) is a member of the serine-threonine protein kinase family. ROCK exists in two isoforms, ROCK1 and ROCK2 (T. Ishizaki et al., EMBO J., 1996, 15, 1885-1893). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (K. Riento and A. J. Ridley, Nat Rev Mol Cell Biol, 2003, 4, 446-56). It is also directly involved in regulating smooth muscle contraction (A. P. Somlyo, Nature, 1997, 389, 908-911). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the RhoA/ROCK signaling pathway plays an important role in signal transduction initiated by several vasoactive factors, for example angiotensin II (T. Yamakawa et al., Hypertension, 2000, 35, 313-318), urotension II (V. Sauzeau et al., Circ. Res., 2001, 88, 1102-1104), endothelin-1 (P. Tangkijvanich et al., Hepatology, 2001, 33, 74-80), serotonin (H. Shimokawa, Jpn. Circ. J., 2000, 64, 1-12), norepinephrine (M. C. Martinez, et al., Am. J. Physiol., 2000, 279, H1228-H1238) and platelet-derived growth factor (PDGF) (H. Kishi et al., J. Biochem., 2000, 128, 719-722). Many of these factors are implicated in the pathogenesis of cardiovascular disease.

Additional studies in the literature, some using the known ROCK inhibitors fasudil (T. Asano et al., J. Pharmacol. Exp. Ther., 1987, 241, 1033-1040) or Y-27632 (M. Uehata et al., Nature, 1997, 389, 990-994) further illustrate the link between ROCK and cardiovascular disease. For example, ROCK expression and activity have been shown to be elevated in spontaneously hypertensive rats, suggesting a link to the development of hypertension in these animals (Y. Mukai et al., FASEB J., 2001, 15, 1062-1064). The ROCK inhibitor Y-27632 (M. Uehata et al., Nature, ibid) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Y. Eto et al., Am. J. Physiol. Heart Circ. Physiol., 2000, 278, H1744-H1750). In a similar model, ROCK inhibitor Y-27632 also inhibited neointimal formation in rats (N. Sawada et al., Circulation, 2000, 101, 2030-2033). In a porcine model of IL-1 beta-induced coronary stenosis, long term treatment with the ROCK inhibitor fasudil was shown to progressively reduce coronary stenosis, as well as promote a regression of coronary constrictive remodeling (H. Shimokawa et al., Cardiovascular Res., 2001, 51, 169-177).

Additional investigations suggest that a ROCK inhibitor would be useful in treating other cardiovascular diseases. For example, in a rat stroke model, fasudil was shown to reduce both the infarct size and neurologic deficit (Y. Toshima, Stroke, 2000, 31, 2245-2250). The ROCK inhibitor Y-27632 was shown to improve ventricular hypertrophy and function in a model of congestive heart failure in Dahl salt-sensitive rats (N. Kobayashi et al., Cardiovascular Res., 2002, 55, 757-767).

Other animal or clinical studies have implicated ROCK in additional diseases including coronary vasospasm (H. Shimokawa et al., Cardiovasc. Res., 1999, 43, 1029-1039), cerebral vasospasm (M. Sato et al., Circ. Res., 2000, 87, 195-200), ischemia/reperfusion injury (T. Yada et al., J. Am. Coll. Cardiol., 2505, 45, 599-607), pulmonary hypertension (Y. Fukumoto et al., Heart, 2005, 91, 391-392), angina (H. Shimokawa et al., J. Cardiovasc. Pharmacol., 2002, 39, 319-327), renal disease (S. Satoh et al., Eur. J. Pharmacol., 2002, 455, 169-174) and erectile dysfunction (N. F. Gonzalez-Cadavid and J. Rajifer, Endocrine, 2004, 23, 167-176).

In another study, it has been demonstrated that inhibition of the RhoA/ROCK signaling pathway allows formation of multiple competing lamellipodia that disrupt the productive migration of monocytes (R. A. Worthylake et al. The Journal of Biol. Chem., 2003, 278, 13578-13584). It has also been reported that small molecule inhibitors of Rho Kinase are capable of inhibiting MCP-1 mediated chemotaxis in vitro (H. Iijima, Biorganic and Medicinal Chemistry, 2007, 15, 1022-1033). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (H. Shimokawa et al., Arterioscler. Thromb. Vasc. Biol., 2005, 25, 1767-1775). Furthermore, Rho-kinase has been indicated as a drug target for the treatment of various other diseases, including airway inflammation and hyperresponsiveness (P. J. Henry et al., Pulm Pharmacol Ther., 2005, 18, 67-74), cancer (R. Rattan et al., J. Neurosci. Res., 2006, 83, 243-55. D. Lepley et al., Cancer Res., 2005, 65, 3788-95), as well as neurological disorders, such as spinal-cord injury, Alzheimer disease, multiple sclerosis, stroke and neuropathic pain (B. K. Mueller et al., Nat Rev Drug Disc, 2005, 4, 387-398; X. Sun et. al., J. Neuroimmunology, 2006, 180, 126-134).

There remains an unmet medical need for new drugs to treat cardiovascular disease. A study published in 2003 estimated that almost 29% of the adult U.S. population had hypertension in 1999-2000 (I. Hajjar et al., JAMA, 2003, 290, 199-206). Furthermore, 69% of the hypertensive individuals studied during this period did not have their hypertension controlled at the time their blood pressure was measured. This figure was worse in patients with diabetes and hypertension where 75% of those patients studied did not have their blood pressure controlled to the target level. Another more recent study showed similar results, with less than one-third of hypertensive patients studied having blood pressure controlled to the target level (V. Andros, Am. J. Manag. Care, 2005, 11, S215-S219). Therefore, despite the number of medications available to treat hypertension, including diuretics, beta blockers, angiotensin converting enzyme inhibitors, angiotensin blockers and calcium channel blockers, hypertension remains poorly controlled or resistant to current medication for many patients. If not adequately treated, hypertension can lead to other cardiovascular diseases and organ failure including coronary artery disease, stroke, myocardial infarction, cardiac failure, renal failure and peripheral artery disease.

Although there are many reports of ROCK inhibitors under investigation (see, for example, U.S. 20100041645 A1, U.S. 20080161297 A1 and E. Hu and D. Lee, Expert Opin. Ther. Targets, 2005, 9, 715-736), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, bronchial asthma, erectile dysfunction, and glaucoma.

BRIEF SUMMARY OF THE INVENTION

In a general aspect, the present invention is directed to the compounds of the formula I:

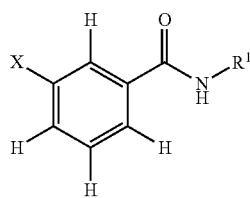

I wherein $R^1$ and X are as defined herein, as well as the tautomers and pharmaceutically acceptable salts thereof. It has been found that the compounds of formula I have valuable pharmacological properties, particularly on inhibiting activity of Rho kinase.

In another aspect, the present invention is directed to a method of inhibiting Rho kinase activity in a patient comprising administering to the patient a compound of the present invention as described above.

In another aspect, the present invention is directed to a method for treating a disease or disorder associated with the activation of Rho kinase which method comprises administering to a patient in need of such treatment a compound of the present invention as described above.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, cardiac failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma and glaucoma, which method comprises administering to a patient in need of such treatment a compound of the present invention as described above.

In another aspect, the present invention is directed to a method of treating diseases mediated at least partially by Rho kinase including spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

DETAILED DESCRIPTION OF THE INVENTION

In an embodiment, there are provided compounds of the formula I

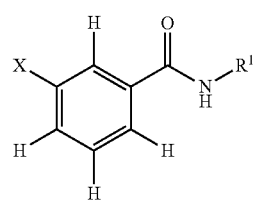

I wherein:
$R^1$ is selected from the group $R^{1a}$ consisting of

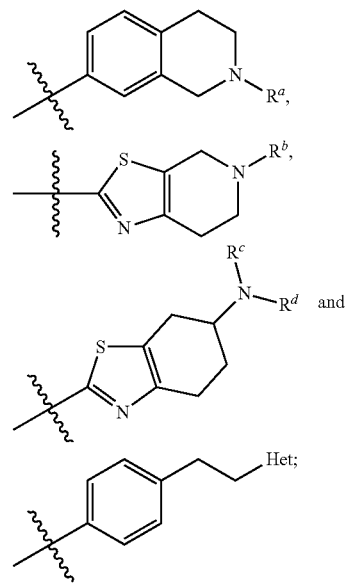

$R^a$ is selected from the group $R^{a1}$ consisting of H and $C_{1-6}$alkyl;
$R^b$ is selected from the group $R^{b1}$ consisting of $C_{1-6}$alkyl and benzyl;
$R^c$ and $R^d$ are independently selected from the group $R^{cd1}$ consisting of H, $C_{1-6}$alkyl, —(CH$_2$)$_2$OMe, —(CH$_2$)$_2$CF$_3$, and —(CH$_2$)$_2$CN; or, included in the group $R^{cd1}$, $R^c$ and $R^d$, together with the N they are bonded to, form a heterocycle selected from morpholine and piperazine, optionally substituted with cyclopropyl or methyl;

Het is selected from N-pyrrolidinyl and N-morpholinyl;

X is selected from the group $X^a$ consisting of

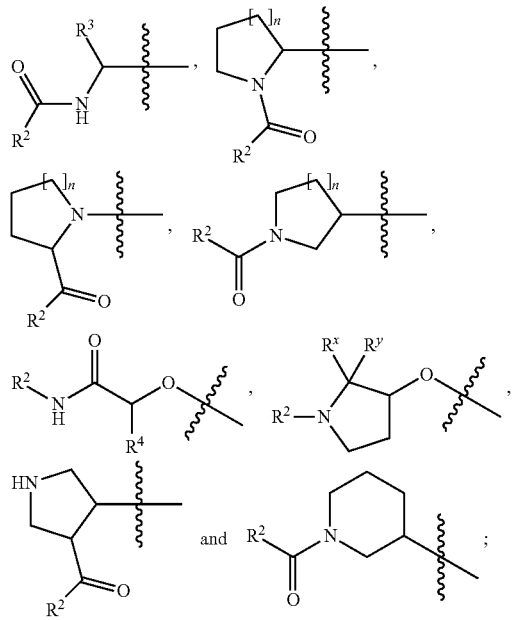

wherein n=1 or 2;

$R^x$ and $R^y$ are H; or $R^x$ and $R^y$ taken together represent oxo;

$R^2$ is selected from the group $R^{2a}$ consisting of

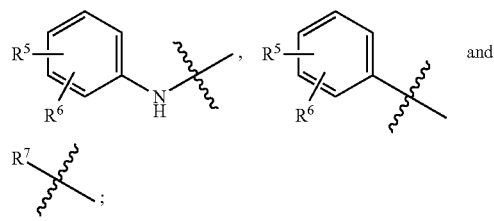

with the proviso that if $R^2$ is

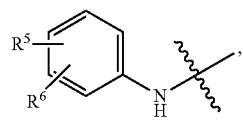

X is not

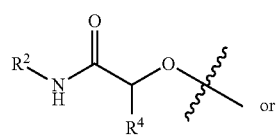

-continued

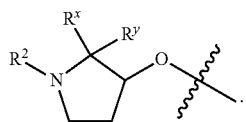

$R^3$ is selected from the group $R^{3a}$ consisting of $C_{1-6}$alkyl, $C_{3-6}$cycloalkyl, and —$CH_2C(O)NHCH_3$;

$R^4$ is selected from H and —$CH_3$;

$R^5$ and $R^6$ are independently selected from H, —$CH_3$, —$OCH_3$, —$C(O)NH_2$, and —CN, provided that $R^5$ and $R^6$ are not both H;

$R^7$ is selected from the group $R^{7a}$ consisting of

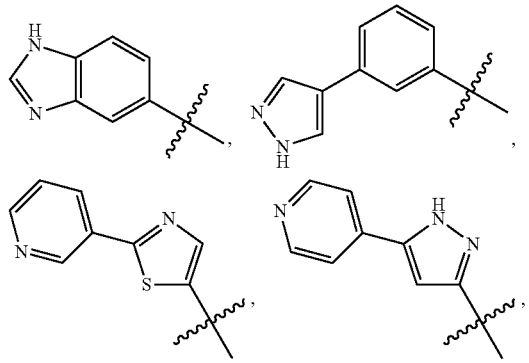

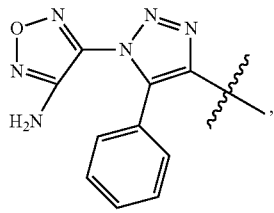

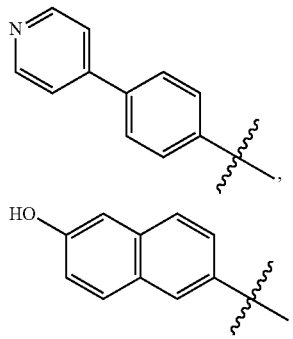

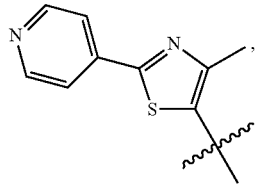

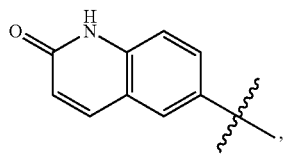

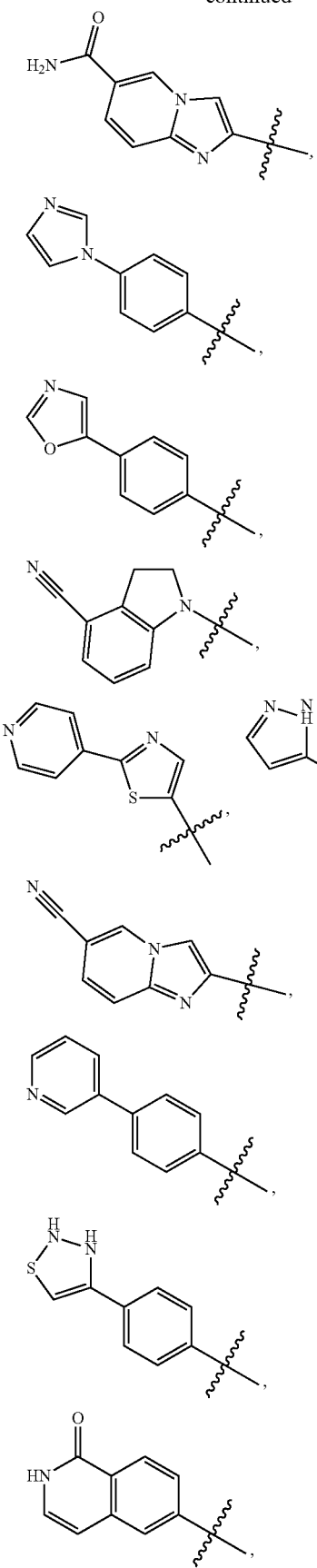
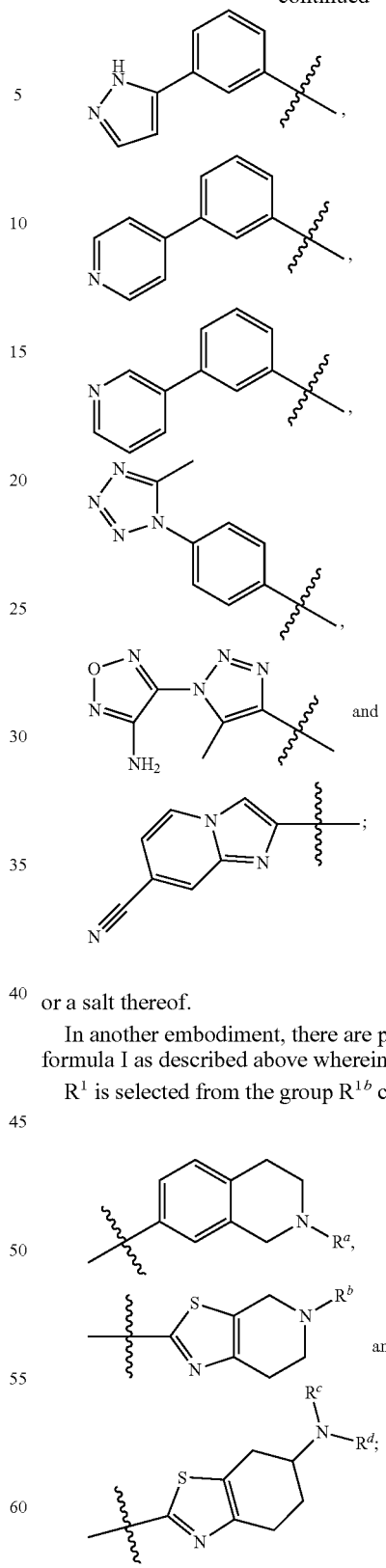
or a salt thereof.
In another embodiment, there are provided compounds of formula I as described above wherein:
$R^1$ is selected from the group $R^{1b}$ consisting of
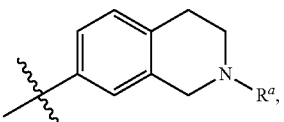
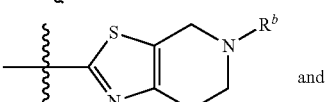
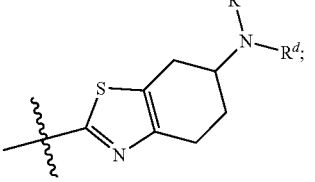
or a salt thereof.
In another embodiment, there are provided compounds of formula I as described in the first embodiment wherein:

$R^1$ is the group $R^{1c}$ consisting of

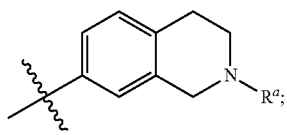

or a salt thereof.

In another embodiment, there are provided compounds of formula I as described in the first embodiment wherein:
$R^1$ is selected from the group $R^{1d}$ consisting of

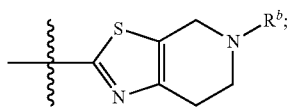

or a salt thereof.

In another embodiment, there are provided compounds of formula I as described in the first embodiment wherein:
$R^1$ is selected from the group $R^{1e}$ consisting of

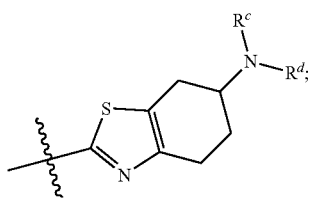

or a salt thereof.

In another embodiment, there are provided compounds of formula I as described in any of the embodiments above wherein:
X is selected from the group $X^b$ consisting of

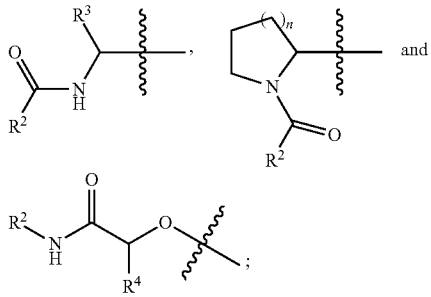

or a salt thereof.

In another embodiment, there are provided compounds of formula I as described in any of the embodiments above wherein:
X is selected from the group $X^c$ consisting of

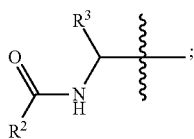

or a salt thereof.

In another embodiment, there are provided compounds of formula I as described in any of the embodiments above wherein:

X is selected from the group $X^d$ consisting of

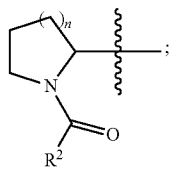

or a salt thereof.

In another embodiment, there are provided compounds of formula I as described in any of the embodiments above wherein:
X is selected from the group $X^e$ consisting of

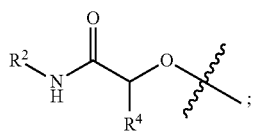

or a salt thereof.

In another embodiment, there are provided compounds of formula I as described in any of the embodiments above wherein:
$R^2$ is selected from the group $R^{2b}$ consisting of

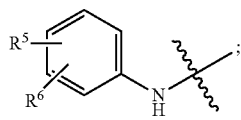

or a salt thereof, with the proviso that X is not

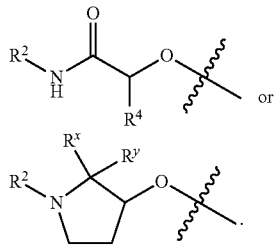

In another embodiment, there are provided compounds of formula I as described in any of the embodiments above wherein:
$R^2$ is selected from the group $R^{2c}$ consisting of

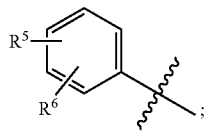

or a salt thereof.

In another embodiment, there are provided compounds of formula I as described in any of the embodiments above wherein:

$R^2$ is selected from the group $R^{2d}$ consisting of

or a salt thereof.

In another embodiment, there are provided compounds of formula I as described in any of the embodiments above wherein:

$R^7$ is selected from the group $R^{7b}$ consisting of

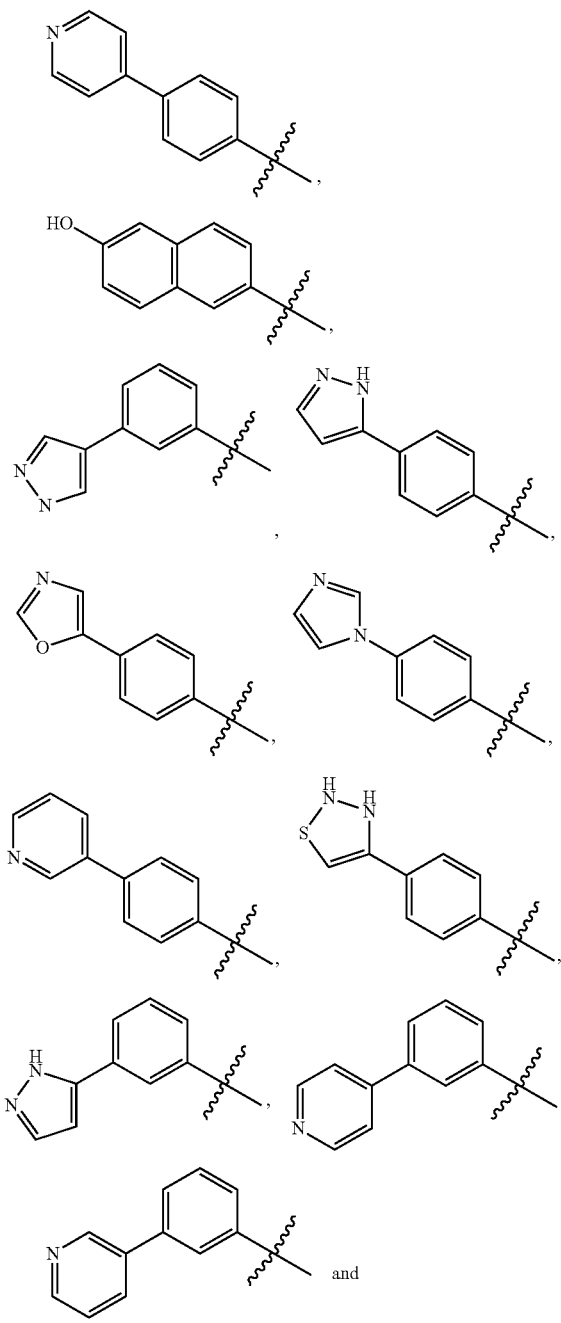

and

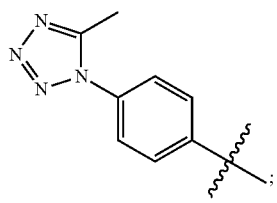

or a salt thereof.

In another embodiment, there are provided compounds of formula I as described in any of the embodiments above wherein:

$R^7$ is selected from the group $R^{7c}$ consisting of

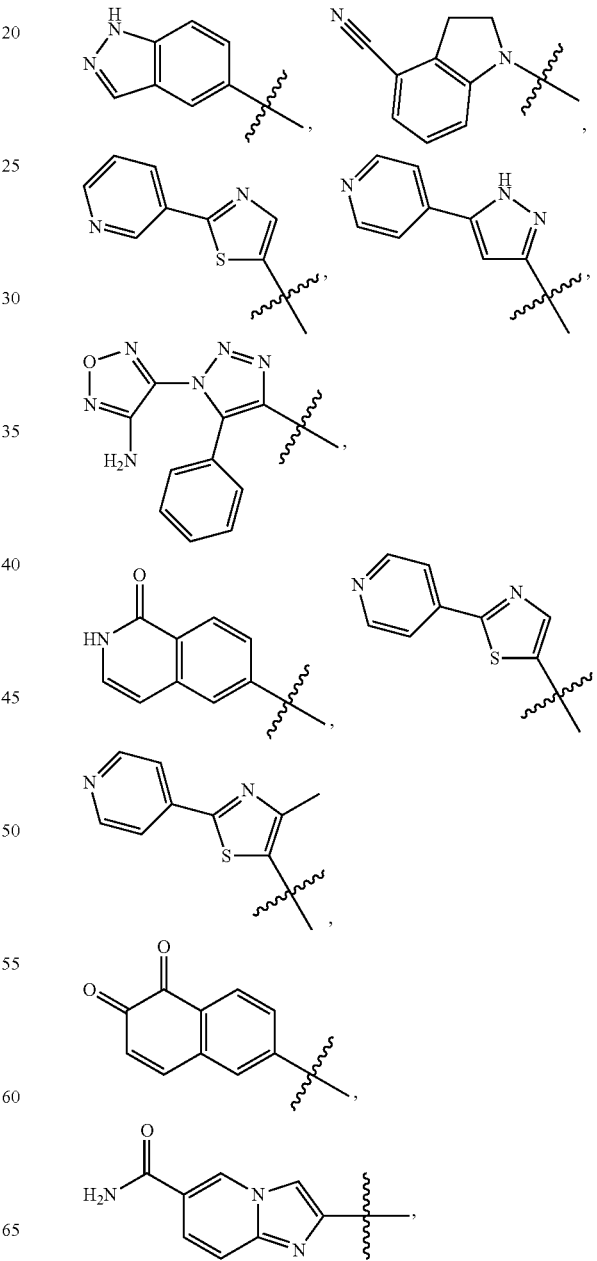

-continued

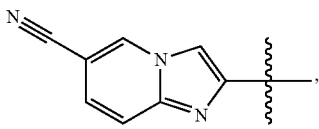

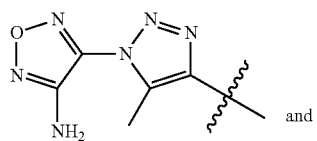
and

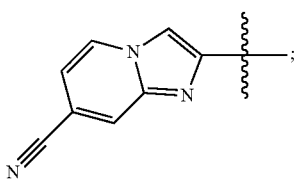
;

or a salt thereof.

In another embodiment, there are provided compounds of formula I as described in any of the embodiments above wherein:

$R^a$ is selected from the group $R^{a2}$ consisting of H and methyl;

$R^c$ and $R^d$ are independently selected from the group $R^{cd2}$ consisting of H, methyl, —(CH$_2$)$_2$OMe, —(CH$_2$)$_2$CF$_3$, and —(CH$_2$)$_2$CN; or $R^c$ and $R^d$, together with the N they are bonded to, form a heterocycle selected from morpholine and piperazine, optionally substituted with cyclopropyl or methyl; and $R^3$ is selected from the group $R^{3b}$ consisting of methyl and cyclopropyl;

or a salt thereof.

Any of the above substituent definitions may be combined to form additional embodiments. For example, the following table shows further representative embodiments of compounds of formula I:

| Embodiment | | | | | | | | |
|---|---|---|---|---|---|---|---|---|
| I-a | $R^{1b}$ | $R^{a1}$ | $R^{b1}$ | $R^{cd1}$ | $X^b$ | $R^{2b}$ | $R^{3b}$ | $R^{7a}$ |
| I-b | $R^{1b}$ | $R^{a1}$ | $R^{b1}$ | $R^{cd1}$ | $X^b$ | $R^{2c}$ | $R^{3b}$ | $R^{7a}$ |
| I-c | $R^{1b}$ | $R^{a1}$ | $R^{b1}$ | $R^{cd1}$ | $X^b$ | $R^{2d}$ | $R^{3b}$ | $R^{7a}$ |
| I-d | $R^{1b}$ | $R^{a1}$ | $R^{b1}$ | $R^{cd1}$ | $X^b$ | $R^{2d}$ | $R^{3b}$ | $R^{7b}$ |
| I-e | $R^{1b}$ | $R^{a1}$ | $R^{b1}$ | $R^{cd1}$ | $X^b$ | $R^{2d}$ | $R^{3b}$ | $R^{7c}$ |
| I-f | $R^{1b}$ | $R^{a1}$ | $R^{b1}$ | $R^{cd1}$ | $X^c$ | $R^{2b}$ | $R^{3b}$ | $R^{7a}$ |
| I-g | $R^{1b}$ | $R^{a1}$ | $R^{b1}$ | $R^{cd1}$ | $X^d$ | $R^{2b}$ | $R^{3b}$ | $R^{7a}$ |
| I-h | $R^{1b}$ | $R^{a1}$ | $R^{b1}$ | $R^{cd1}$ | $X^d$ | $R^{2b}$ | $R^{3b}$ | $R^{7b}$ |
| I-i | $R^{1c}$ | $R^{a1}$ | $R^{b1}$ | $R^{cd1}$ | $X^b$ | $R^{2d}$ | $R^{3b}$ | $R^{7a}$ |
| I-j | $R^{1d}$ | $R^{a1}$ | $R^{b1}$ | $R^{cd1}$ | $X^b$ | $R^{2d}$ | $R^{3b}$ | $R^{7a}$ |
| I-k | $R^{1e}$ | $R^{a1}$ | $R^{b1}$ | $R^{cd1}$ | $X^b$ | $R^{2d}$ | $R^{3b}$ | $R^{7a}$ |
| 1-l | $R^{1d}$ | $R^{a1}$ | $R^{b1}$ | $R^{cd1}$ | $X^d$ | $R^{2c}$ | $R^{3b}$ | $R^{7a}$ |
| I-m | $R^{1d}$ | $R^{a1}$ | $R^{b1}$ | $R^{cd1}$ | $X^d$ | $R^{2d}$ | $R^{3b}$ | $R^{7a}$ |
| I-n | $R^{1e}$ | $R^{a1}$ | $R^{b1}$ | $R^{cd1}$ | $X^d$ | $R^{2c}$ | $R^{3b}$ | $R^{7a}$ |
| I-o | $R^{1e}$ | $R^{a1}$ | $R^{b1}$ | $R^{cd1}$ | $X^d$ | $R^{2d}$ | $R^{3b}$ | $R^{7a}$ |

Further embodiments include any of the embodiments listed above the table or in the table wherein n=1.

The following are representative compounds of the invention which can be made by the general synthetic schemes, the examples, and known methods in the art.

TABLE 1

| Cpd # |
|---|
| 1 |

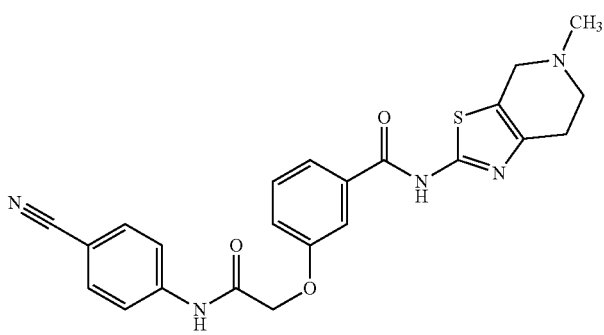 [SMILES: CN1CCc2nc(NC(=O)c3cccc(OCC(=O)Nc4ccc(C#N)cc4)c3)sc2C1]

| 2 |

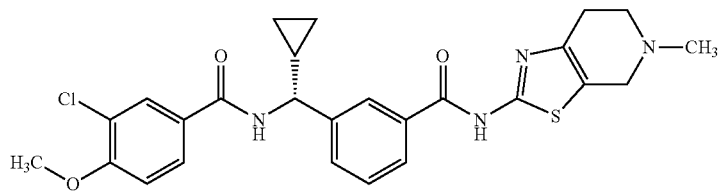

TABLE 1-continued
| Cpd # | |
|---|---|
| 3 | 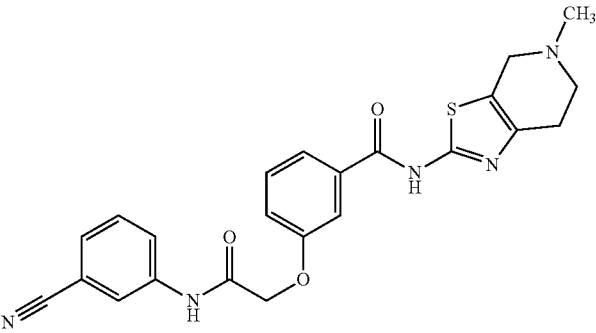 [SMILES: CN1CCc2nc(NC(=O)c3cccc(OCC(=O)Nc4cccc(C#N)c4)c3)sc2C1] |
| 4 | 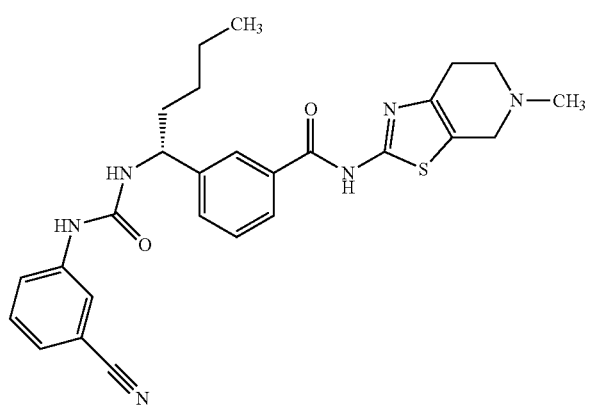 [SMILES: CCCC[C@@H](NC(=O)Nc1cccc(C#N)c1)c1cccc(C(=O)Nc2nc3c(s2)CN(C)CC3)c1] |
| 5 | 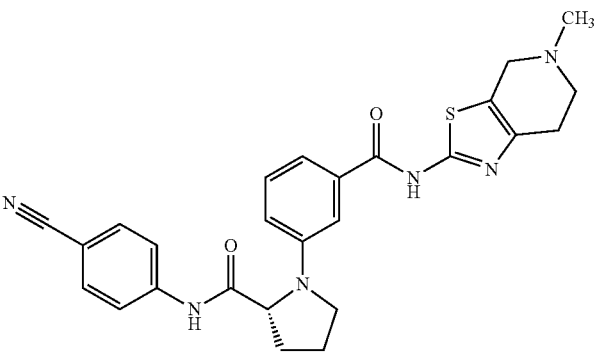 [SMILES: CN1CCc2nc(NC(=O)c3cccc(N4CCC[C@@H]4C(=O)Nc4ccc(C#N)cc4)c3)sc2C1] |
| 6 | 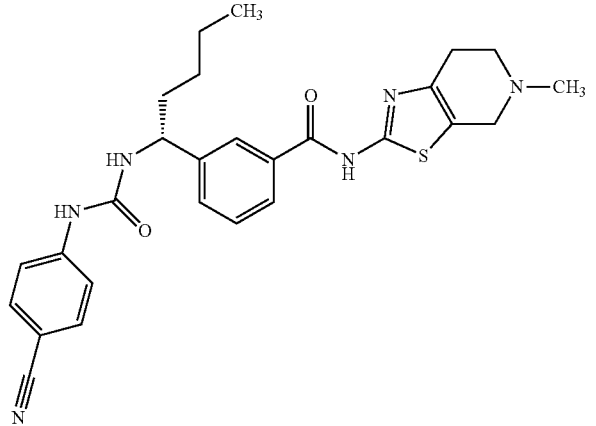 [SMILES: CCCC[C@@H](NC(=O)Nc1ccc(C#N)cc1)c1cccc(C(=O)Nc2nc3c(s2)CN(C)CC3)c1] |

TABLE 1-continued
| Cpd # |
| --- |
| 7 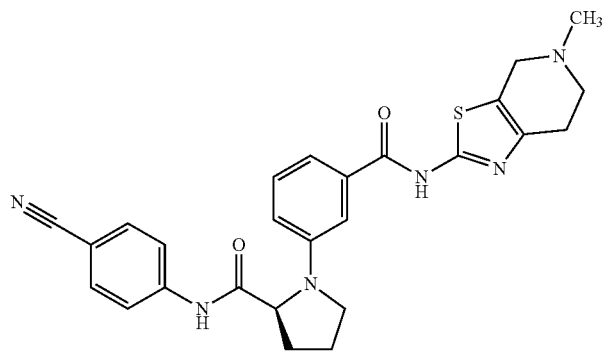 [SMILES: CN1CCc2nc(NC(=O)c3cccc(N4CCC[C@H]4C(=O)Nc4ccc(C#N)cc4)c3)sc2C1] |
| 8 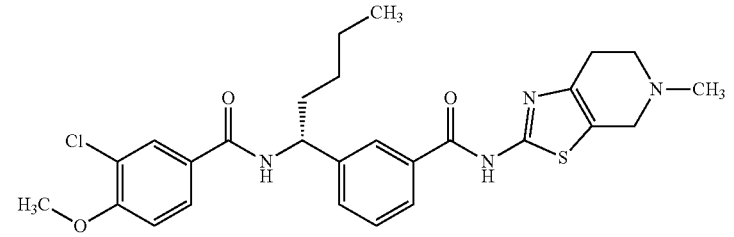 |
| 9 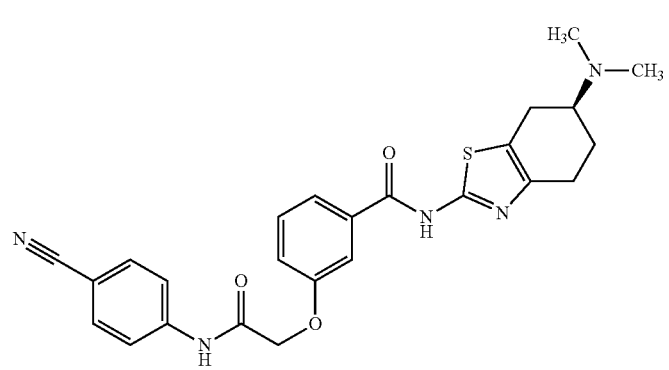 [SMILES: CN(C)[C@H]1CCc2nc(NC(=O)c3cccc(OCC(=O)Nc4ccc(C#N)cc4)c3)sc2C1] |
| 10 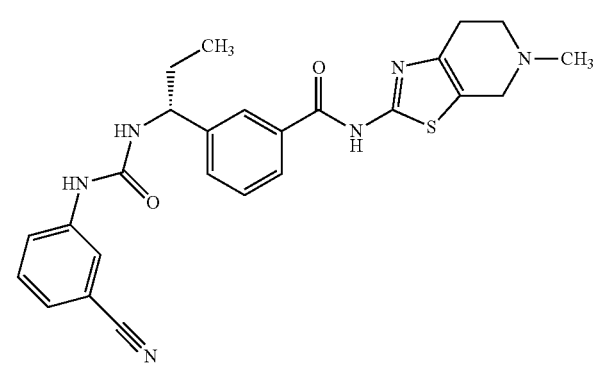 [SMILES: CC[C@@H](NC(=O)Nc1cccc(C#N)c1)c1cccc(C(=O)Nc2nc3c(s2)CN(C)CC3)c1] |

TABLE 1-continued
| Cpd # |
| --- |
| 11 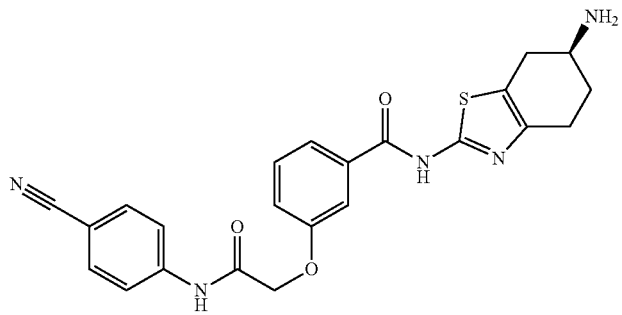 [SMILES: N#Cc1ccc(NC(=O)COc2cccc(C(=O)Nc3nc4c(s3)C[C@@H](N)CC4)c2)cc1] |
| 12 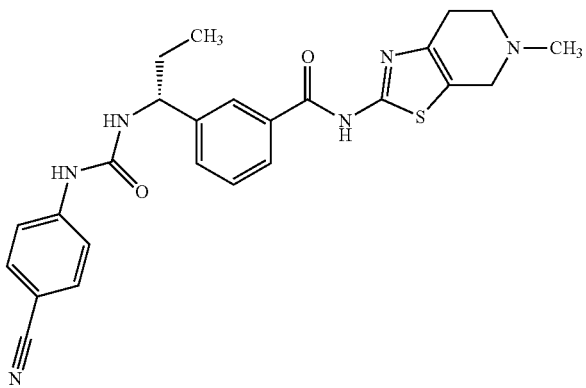 [SMILES: CC[C@@H](NC(=O)Nc1ccc(C#N)cc1)c1cccc(C(=O)Nc2nc3c(s2)CN(C)CC3)c1] |
| 13 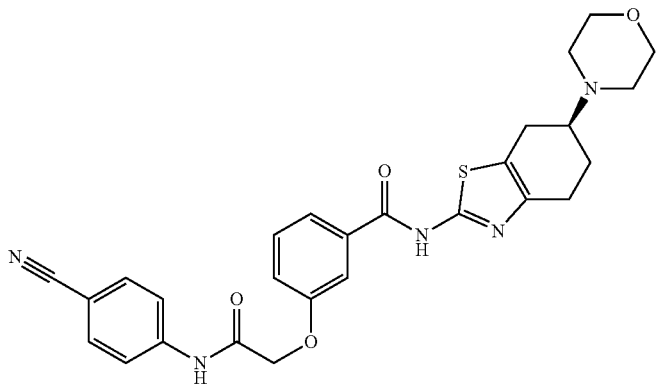 [SMILES: N#Cc1ccc(NC(=O)COc2cccc(C(=O)Nc3nc4c(s3)C[C@@H](N3CCOCC3)CC4)c2)cc1] |
| 14 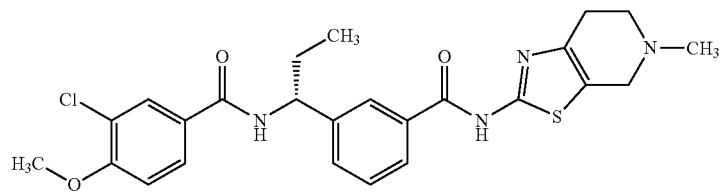 |

TABLE 1-continued
| Cpd # | |
|---|---|
| 15 | 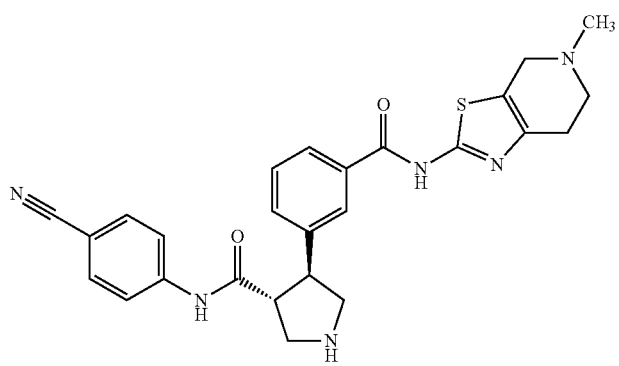 [SMILES: CN1CCc2nc(NC(=O)c3cccc([C@H]4CNC[C@@H]4C(=O)Nc4ccc(C#N)cc4)c3)sc2C1] |
| 16 | 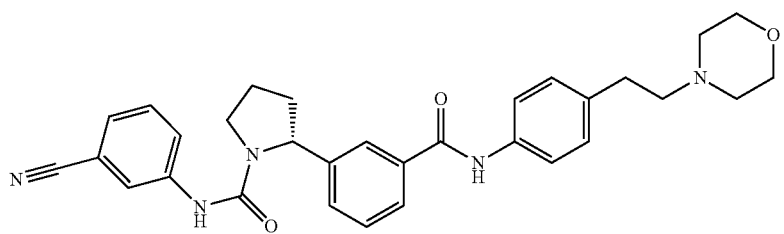 [SMILES: N#Cc1cccc(NC(=O)N2CCC[C@@H]2c2cccc(C(=O)Nc3ccc(CCN4CCOCC4)cc3)c2)c1] |
| 17 | 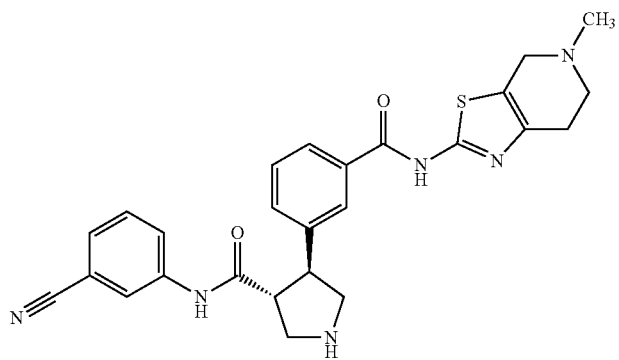 [SMILES: CN1CCc2nc(NC(=O)c3cccc([C@H]4CNC[C@@H]4C(=O)Nc4cccc(C#N)c4)c3)sc2C1] |
| 18 | 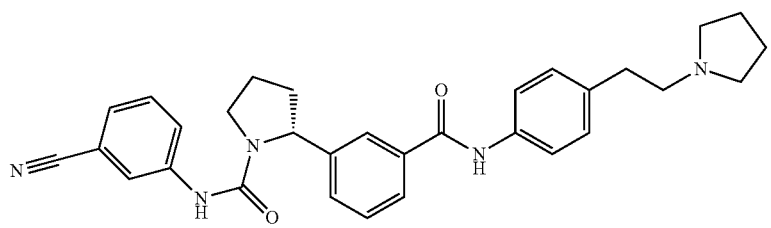 [SMILES: N#Cc1cccc(NC(=O)N2CCC[C@@H]2c2cccc(C(=O)Nc3ccc(CCN4CCCC4)cc3)c2)c1] |
| 19 | 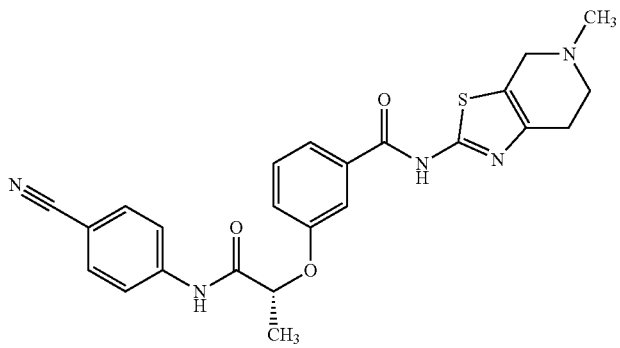 [SMILES: C[C@@H](Oc1cccc(C(=O)Nc2nc3c(s2)CN(C)CC3)c1)C(=O)Nc1ccc(C#N)cc1] |

TABLE 1-continued
Cpd #
20
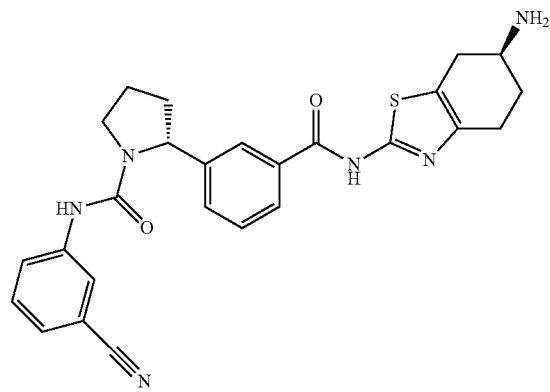 [SMILES: N#Cc1cccc(NC(=O)N2CCC[C@@H]2c2cccc(C(=O)Nc3nc4c(s3)C[C@@H](N)CC4)c2)c1]
21
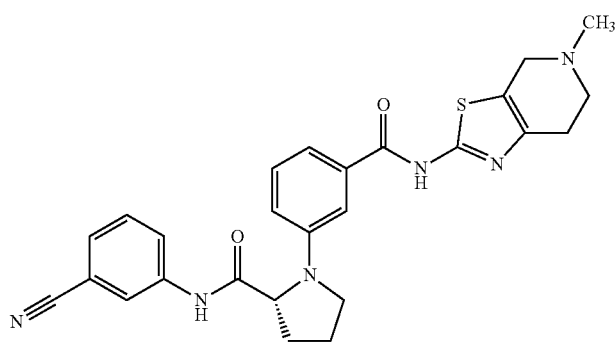 [SMILES: CN1CCc2nc(NC(=O)c3cccc(N4CCC[C@@H]4C(=O)Nc4cccc(C#N)c4)c3)sc2C1]
22
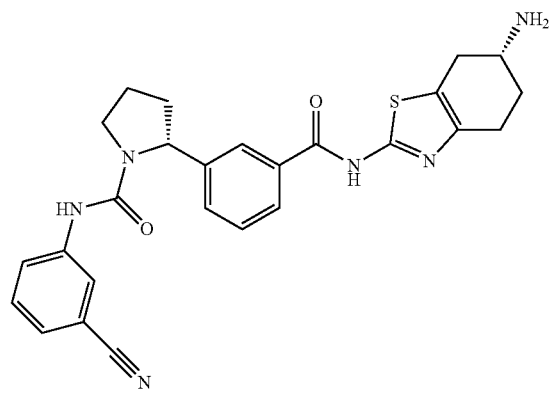 [SMILES: N#Cc1cccc(NC(=O)N2CCC[C@@H]2c2cccc(C(=O)Nc3nc4c(s3)C[C@H](N)CC4)c2)c1]
23
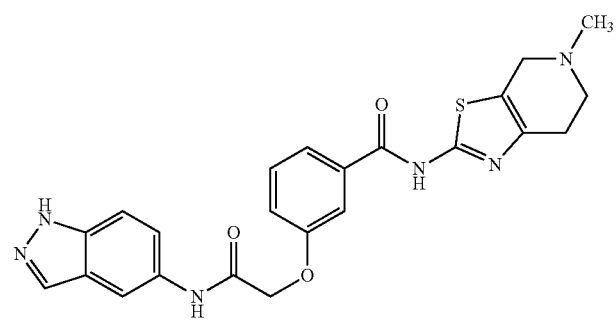 [SMILES: CN1CCc2nc(NC(=O)c3cccc(OCC(=O)Nc4ccc5[nH]ncc5c4)c3)sc2C1]

TABLE 1-continued

| Cpd # |
| --- |
| 24 |
| 25 |
| 26 |
| 27 |
| 28 |

TABLE 1-continued

| Cpd # |
|---|
| 29 |
| 30 |
| 31 |
| 32 |
| 33 |

TABLE 1-continued
| Cpd # | |
|---|---|
| 34 | 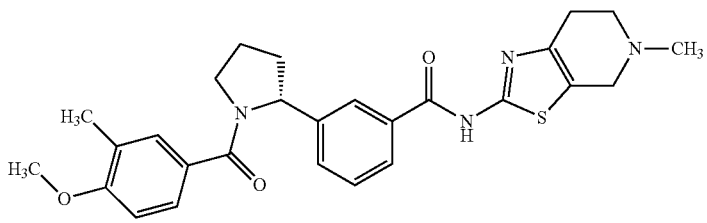 |
| 35 | 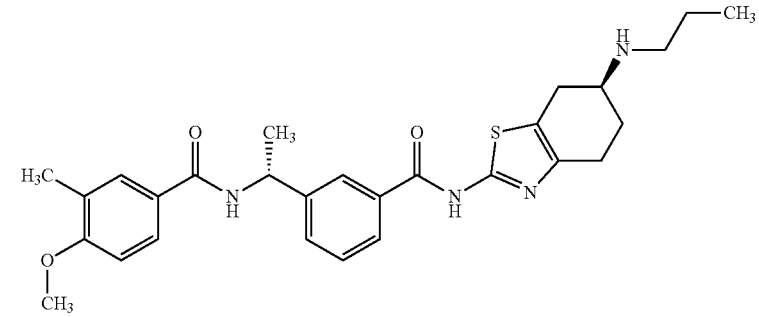 [SMILES: CCCN[C@H]1CCc2nc(NC(=O)c3cccc([C@@H](C)NC(=O)c4ccc(OC)c(C)c4)c3)sc2C1] |
| 36 | 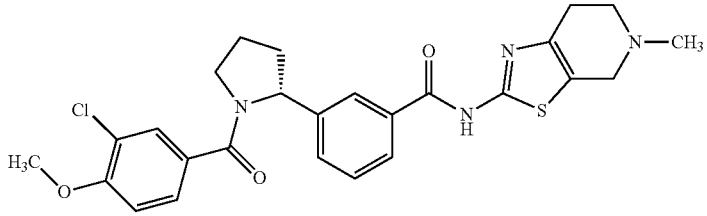 |
| 37 | 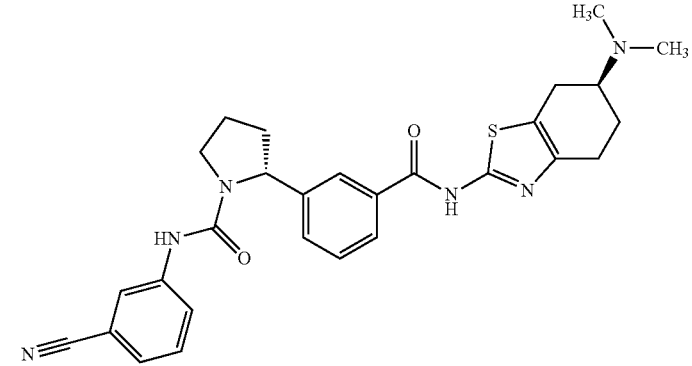 [SMILES: CN(C)[C@H]1CCc2nc(NC(=O)c3cccc([C@H]4CCCN4C(=O)Nc4cccc(C#N)c4)c3)sc2C1] |
| 38 | 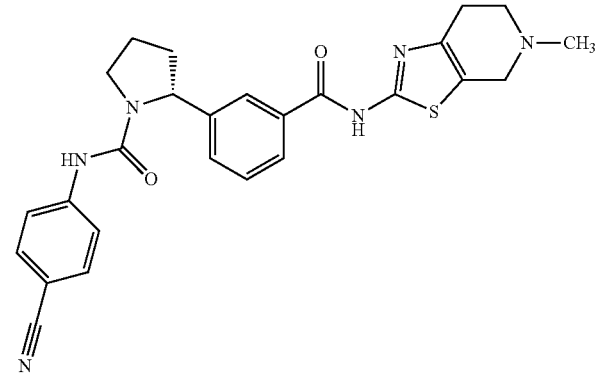 [SMILES: CN1CCc2nc(NC(=O)c3cccc([C@H]4CCCN4C(=O)Nc4ccc(C#N)cc4)c3)sc2C1] |

TABLE 1-continued
Cpd #
39
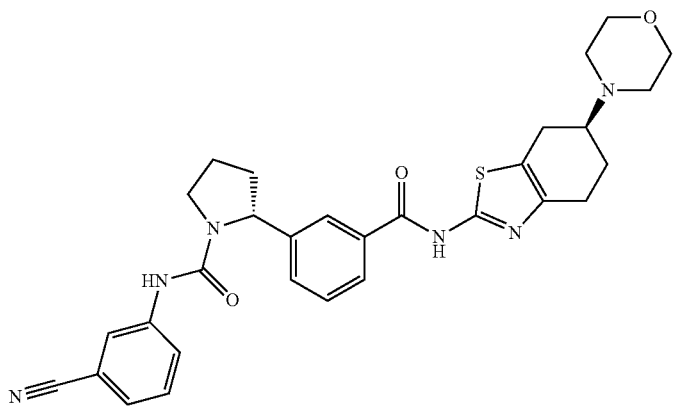 [SMILES: N#Cc1cccc(NC(=O)N2CCC[C@@H]2c2cccc(C(=O)Nc3nc4c(s3)C[C@@H](N3CCOCC3)CC4)c2)c1]
40
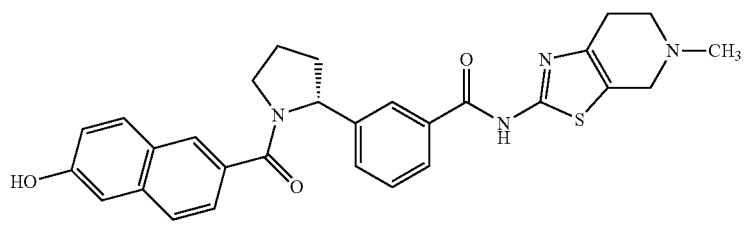 [SMILES: CN1CCc2nc(NC(=O)c3cccc([C@H]4CCCN4C(=O)c4ccc5cc(O)ccc5c4)c3)sc2C1]
41
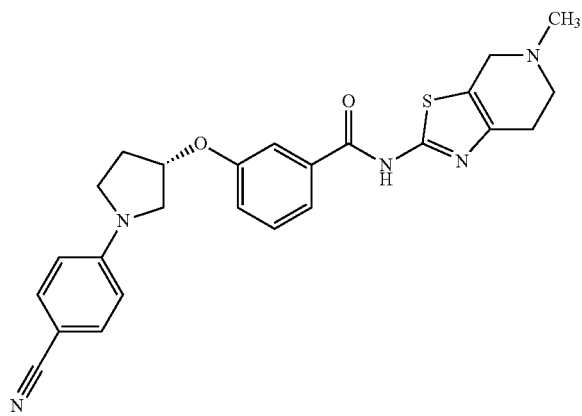 [SMILES: CN1CCc2nc(NC(=O)c3cccc(O[C@H]4CCN(c5ccc(C#N)cc5)C4)c3)sc2C1]
42
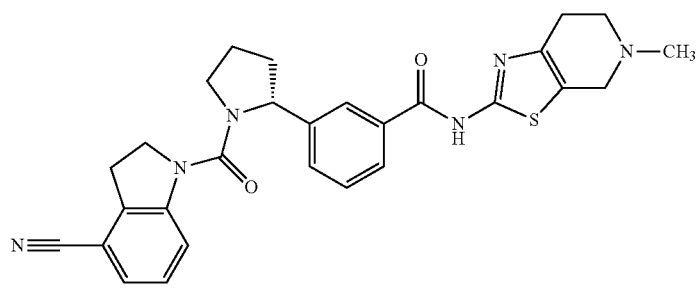 [SMILES: CN1CCc2nc(NC(=O)c3cccc([C@H]4CCCN4C(=O)N4CCc5c(C#N)cccc54)c3)sc2C1]

TABLE 1-continued
| Cpd # |
| --- |
| 43 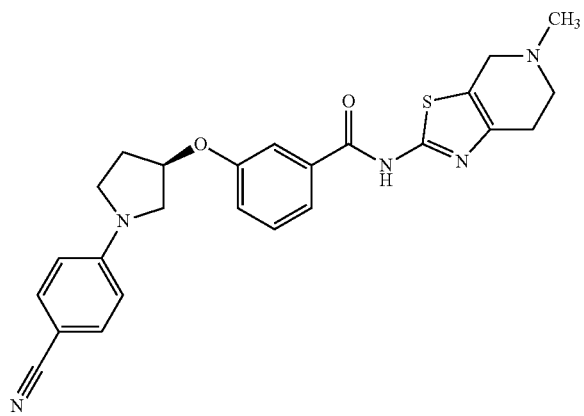 [SMILES: CN1CCc2nc(NC(=O)c3cccc(O[C@@H]4CCN(c5ccc(C#N)cc5)C4)c3)sc2C1] |
| 44 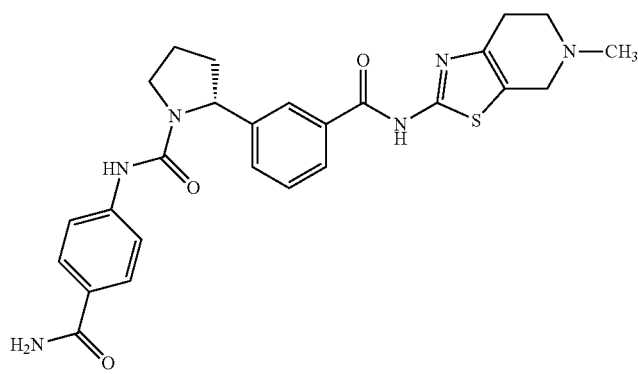 [SMILES: CN1CCc2nc(NC(=O)c3cccc([C@H]4CCCN4C(=O)Nc4ccc(C(N)=O)cc4)c3)sc2C1] |
| 45 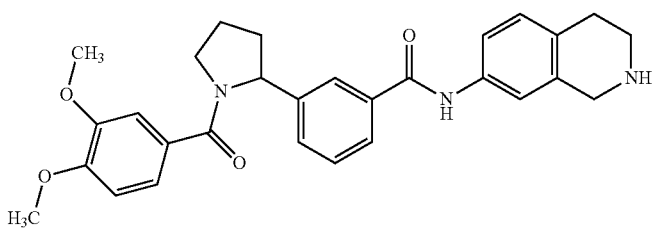 [SMILES: COc1ccc(C(=O)N2CCCC2c2cccc(C(=O)Nc3ccc4c(c3)CNCC4)c2)cc1OC] |
| 46 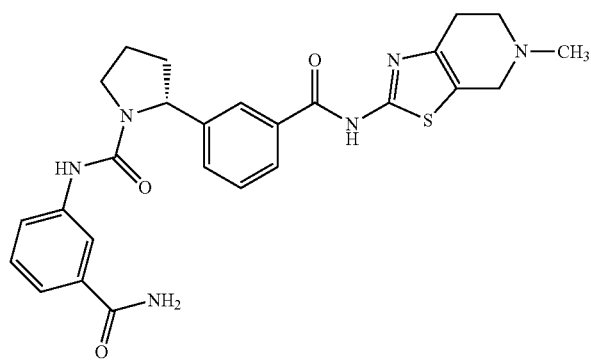 [SMILES: CN1CCc2nc(NC(=O)c3cccc([C@H]4CCCN4C(=O)Nc4cccc(C(N)=O)c4)c3)sc2C1] |

TABLE 1-continued

Cpd #

47

48

49

50

TABLE 1-continued

| Cpd # |
|---|
| 51 |
| 52 |
| 53 |
| 54 |
| 55 |

TABLE 1-continued
Cpd #
56
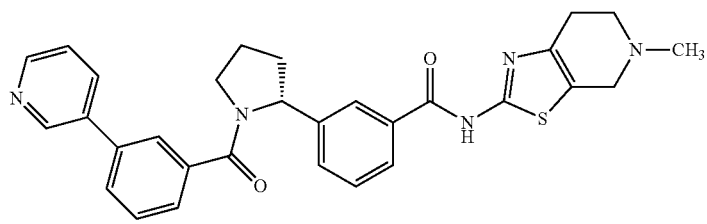 [SMILES: CN1CCc2nc(NC(=O)c3cccc([C@H]4CCCN4C(=O)c4cccc(-c5cccnc5)c4)c3)sc2C1]
57
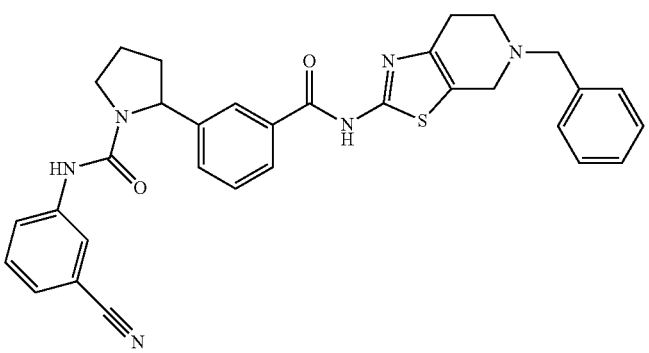
58
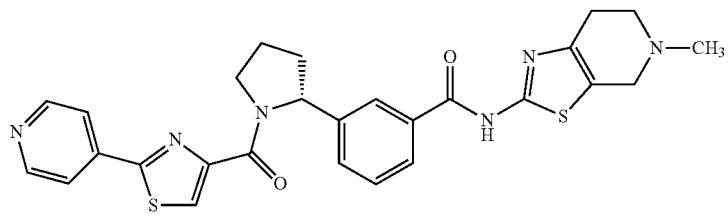 [SMILES: CN1CCc2nc(NC(=O)c3cccc([C@H]4CCCN4C(=O)c4csc(-c5ccncc5)n4)c3)sc2C1]
59
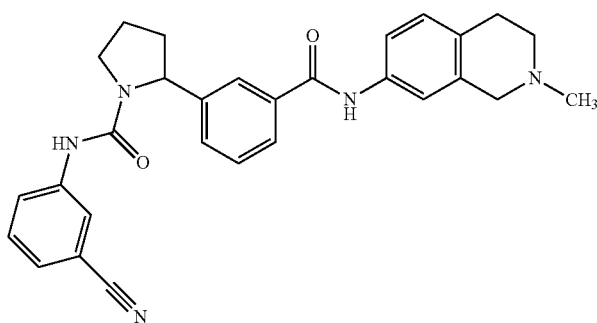 [SMILES: CN1CCc2ccc(NC(=O)c3cccc(C4CCCN4C(=O)Nc4cccc(C#N)c4)c3)cc2C1]
60
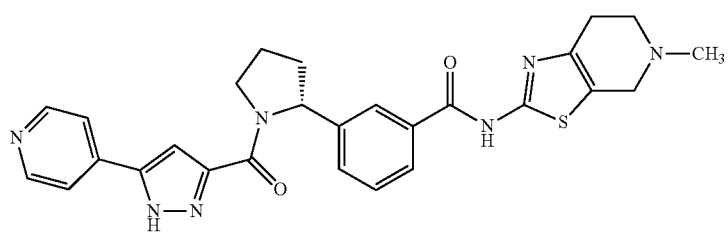 [SMILES: CN1CCc2nc(NC(=O)c3cccc([C@H]4CCCN4C(=O)c4cc(-c5ccncc5)[nH]n4)c3)sc2C1]

TABLE 1-continued

| Cpd # |
| --- |
| 61 |
| 62 |
| 63 |
| 64 |
| 65 |

TABLE 1-continued

| Cpd # |
| --- |
| 66 |
| 67 |
| 68 |
| 69 |
| 70 |
| 71 |

TABLE 1-continued
Cpd #
72
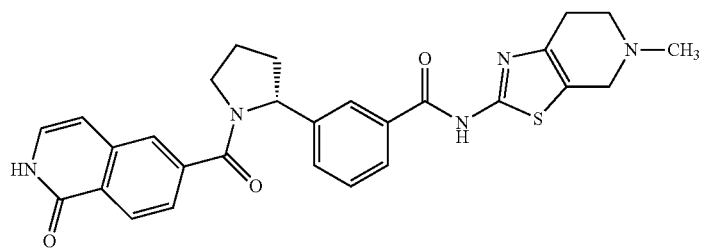 [SMILES: CN1CCc2nc(NC(=O)c3cccc([C@H]4CCCN4C(=O)c4ccc5c(=O)[nH]ccc5c4)c3)sc2C1]
73
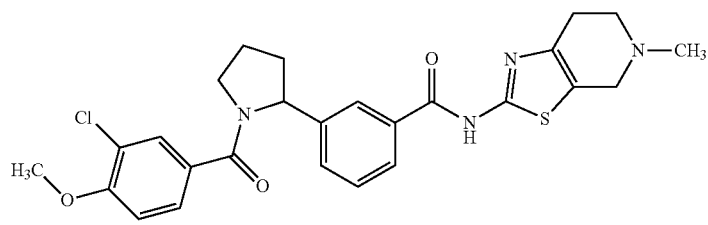
74
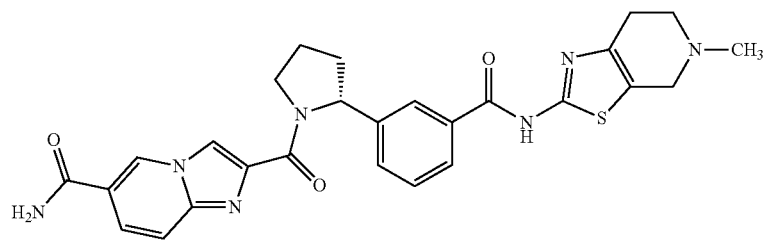 [SMILES: CN1CCc2nc(NC(=O)c3cccc([C@H]4CCCN4C(=O)c4cn5cc(C(N)=O)ccc5n4)c3)sc2C1]
75
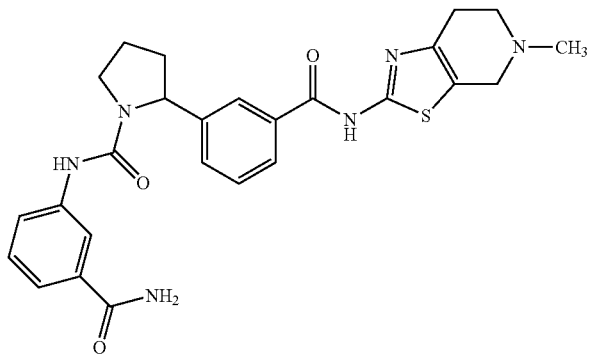
76
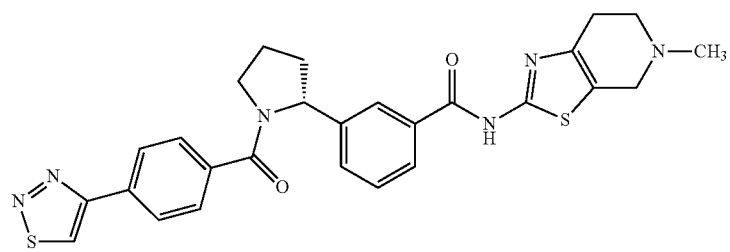 [SMILES: CN1CCc2nc(NC(=O)c3cccc([C@H]4CCCN4C(=O)c4ccc(-c5csnn5)cc4)c3)sc2C1]

TABLE 1-continued
| Cpd # | |
|---|---|
| 77 | 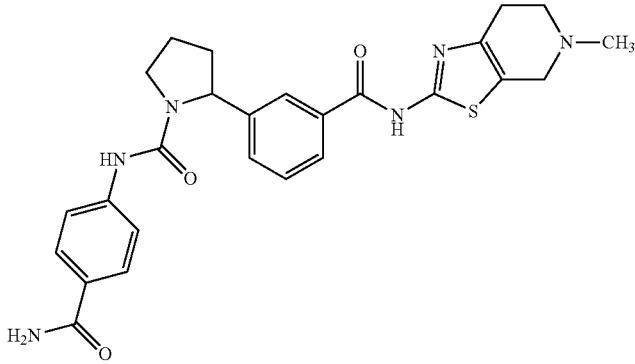 |
| 78 | 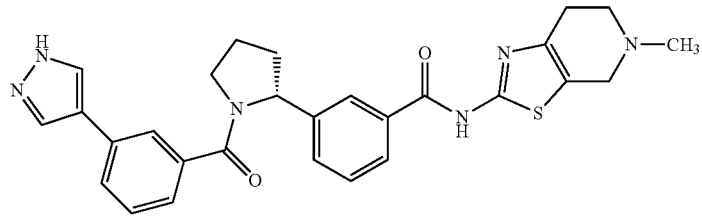 [SMILES: CN1CCc2nc(NC(=O)c3cccc([C@H]4CCCN4C(=O)c4cccc(-c5cn[nH]c5)c4)c3)sc2C1] |
| 79 | 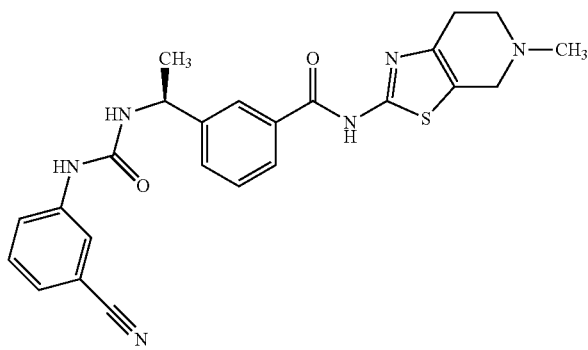 [SMILES: C[C@H](NC(=O)Nc1cccc(C#N)c1)c1cccc(C(=O)Nc2nc3c(s2)CN(C)CC3)c1] |
| 80 | 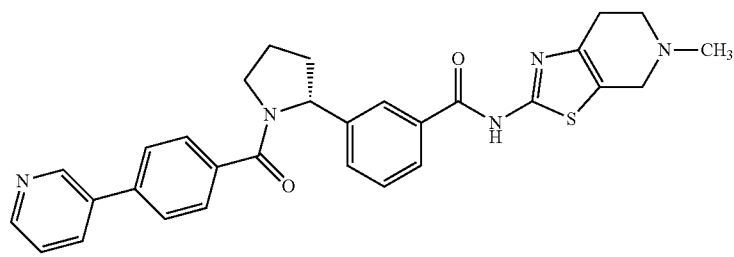 [SMILES: CN1CCc2nc(NC(=O)c3cccc([C@H]4CCCN4C(=O)c4ccc(-c5cccnc5)cc4)c3)sc2C1] |
| 81 | 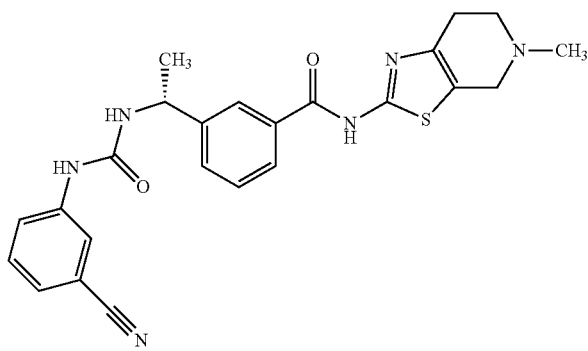 [SMILES: C[C@@H](NC(=O)Nc1cccc(C#N)c1)c1cccc(C(=O)Nc2nc3c(s2)CN(C)CC3)c1] |

TABLE 1-continued

| Cpd # |
| --- |
| 82 |
| 83 |
| 84 |
| 85 |

TABLE 1-continued

| Cpd # |
|---|
| 86 |
| 87 |
| 88 |
| 89 |
| 90 |
| 91 |

TABLE 1-continued

| Cpd # |
|---|
| 92 |
| 93 |
| 94 |
| 95 |
| 96 |
| 97 |

TABLE 1-continued
| Cpd # | |
|---|---|
| 98 | 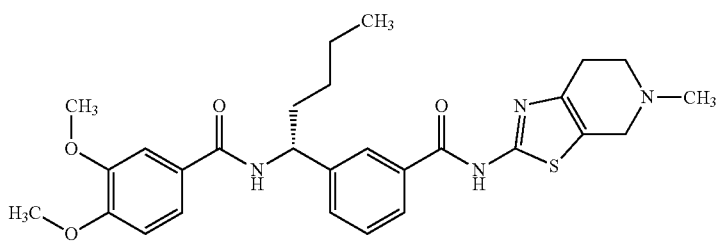 |
| 99 | 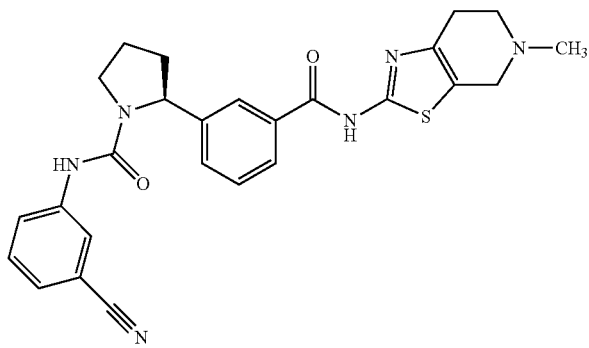 [SMILES: CN1CCc2nc(NC(=O)c3cccc([C@@H]4CCCN4C(=O)Nc4cccc(C#N)c4)c3)sc2C1] |
| 100 | 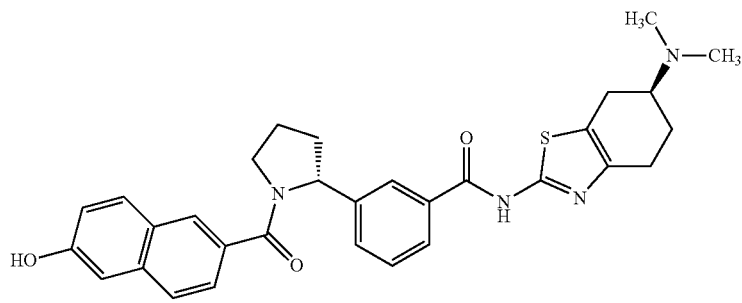 [SMILES: CN(C)[C@H]1CCc2nc(NC(=O)c3cccc([C@H]4CCCN4C(=O)c4ccc5cc(O)ccc5c4)c3)sc2C1] |
| 101 | 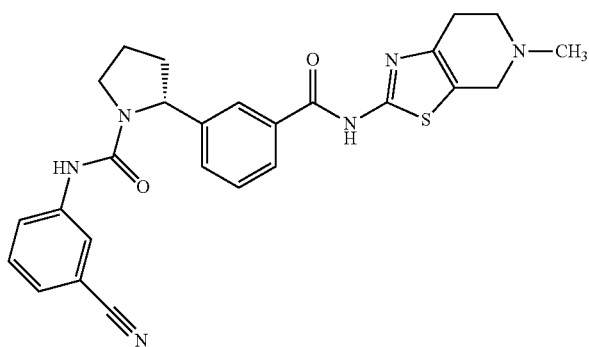 [SMILES: CN1CCc2nc(NC(=O)c3cccc([C@H]4CCCN4C(=O)Nc4cccc(C#N)c4)c3)sc2C1] |
| 102 | 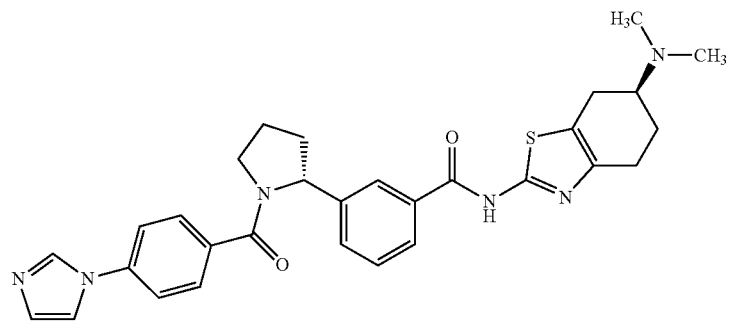 [SMILES: CN(C)[C@H]1CCc2nc(NC(=O)c3cccc([C@H]4CCCN4C(=O)c4ccc(-n5ccnc5)cc4)c3)sc2C1] |

TABLE 1-continued

Cpd #

103

104

105

106

TABLE 1-continued
| Cpd # | |
|---|---|
| 107 | 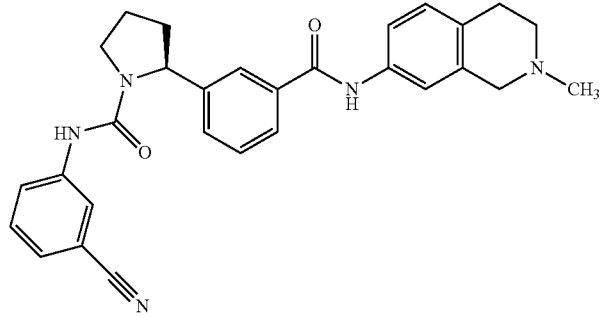 [SMILES: CN1CCc2ccc(NC(=O)c3cccc([C@@H]4CCCN4C(=O)Nc4cccc(C#N)c4)c3)cc2C1] |
| 108 | 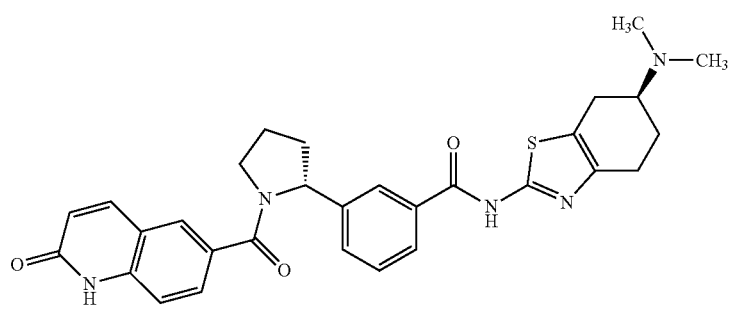 [SMILES: CN(C)[C@H]1CCc2nc(NC(=O)c3cccc([C@H]4CCCN4C(=O)c4ccc5[nH]c(=O)ccc5c4)c3)sc2C1] |
| 109 | 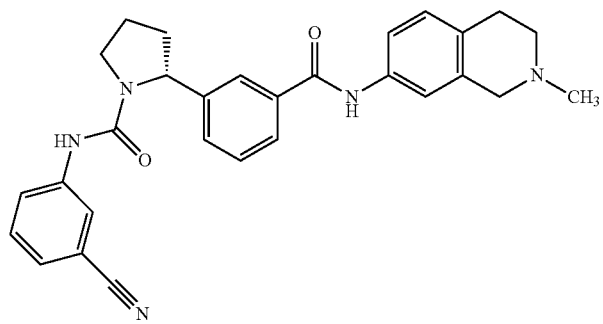 [SMILES: CN1CCc2ccc(NC(=O)c3cccc([C@H]4CCCN4C(=O)Nc4cccc(C#N)c4)c3)cc2C1] |
| 110 | 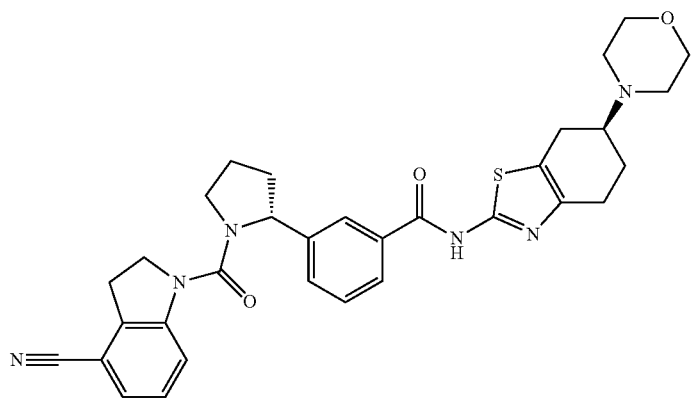 [SMILES: N#Cc1cccc2c1CCN2C(=O)N1CCC[C@@H]1c1cccc(C(=O)Nc2nc3c(s2)C[C@@H](N2CCOCC2)CC3)c1] |
| 111 | 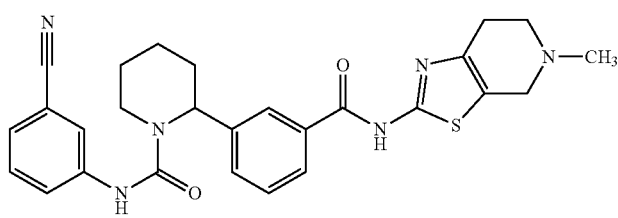 [SMILES: CN1CCc2nc(NC(=O)c3cccc(C4CCCCN4C(=O)Nc4cccc(C#N)c4)c3)sc2C1] |

TABLE 1-continued
| Cpd # |
|---|
| 112 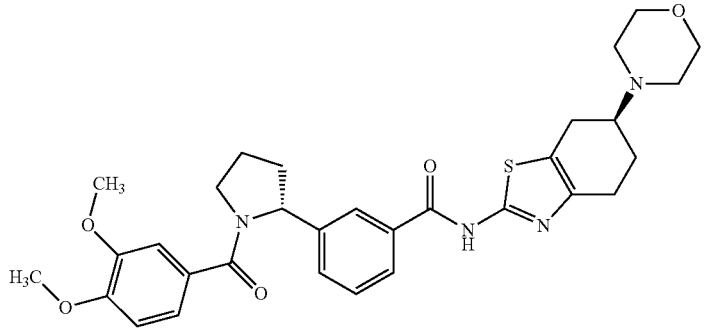 [SMILES: COc1ccc(C(=O)N2CCC[C@@H]2c2cccc(C(=O)Nc3nc4c(s3)C[C@@H](N3CCOCC3)CC4)c2)cc1OC] |
| 113 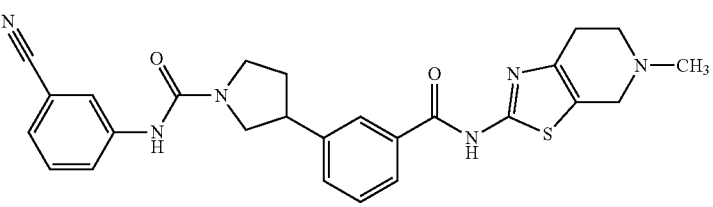 [SMILES: CN1CCc2nc(NC(=O)c3cccc(C4CCN(C(=O)Nc5cccc(C#N)c5)C4)c3)sc2C1] |
| 114 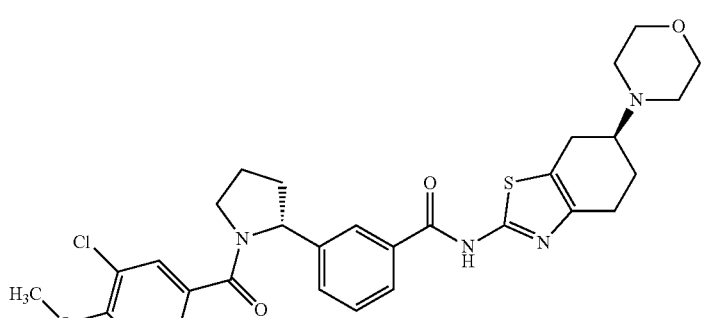 |
| 115 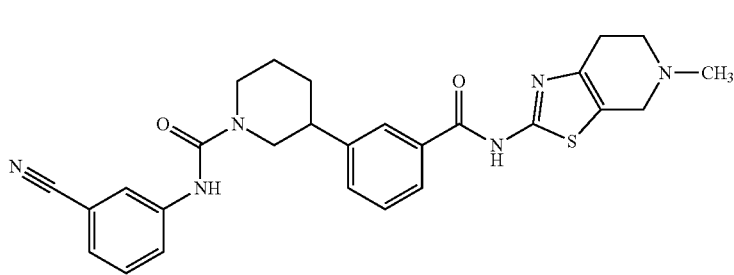 |
| 116 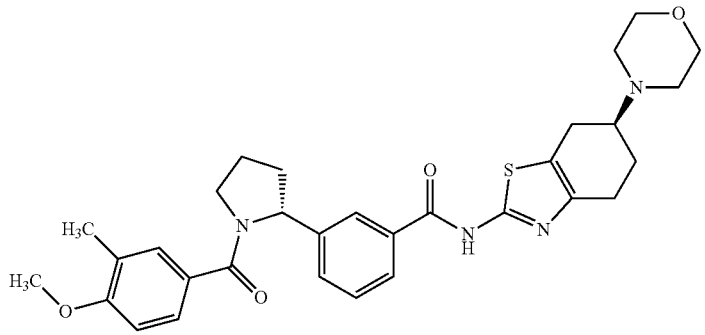 [SMILES: COc1ccc(C(=O)N2CCC[C@@H]2c2cccc(C(=O)Nc3nc4c(s3)C[C@@H](N3CCOCC3)CC4)c2)cc1Cl] |

TABLE 1-continued

| Cpd # |
|---|
| 117 |
| 118 |
| 119 |
| 120 |
| 121 |

татtable
TABLE 1-continued
| Cpd # | |
|---|---|
| 122 | 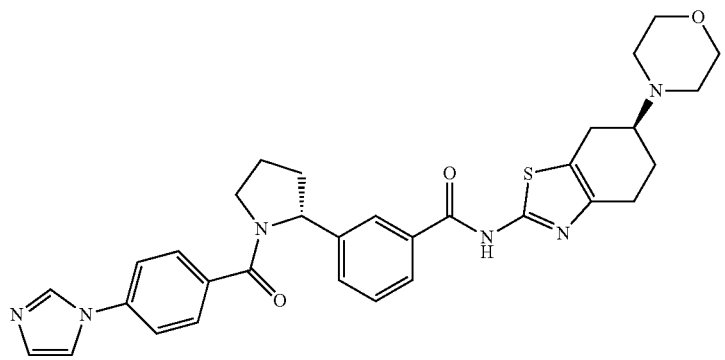 [SMILES: O=C(Nc1nc2c(s1)C[C@@H](N1CCOCC1)CC2)c1cccc([C@H]2CCCN2C(=O)c2ccc(-n3ccnc3)cc2)c1] |
| 123 | 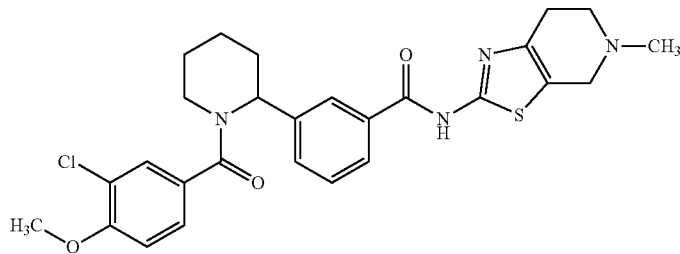 |
| 124 | 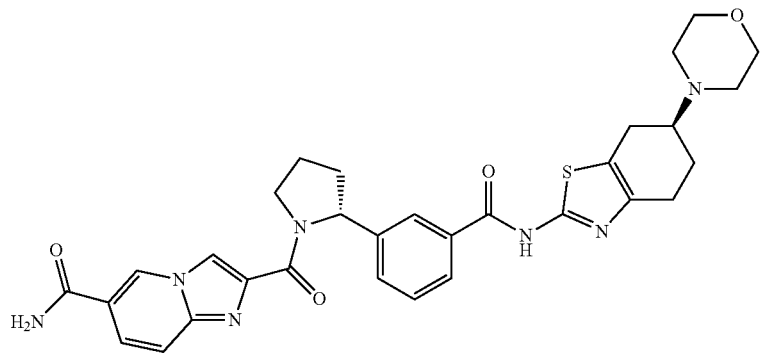 [SMILES: NC(=O)c1ccc2nc(C(=O)N3CCC[C@@H]3c3cccc(C(=O)Nc4nc5c(s4)C[C@@H](N4CCOCC4)CC5)c3)cn2c1] |
| 125 | 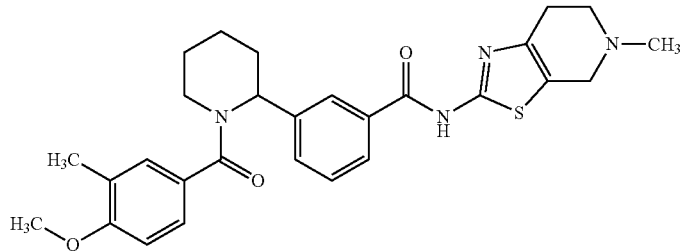 |
| 126 | 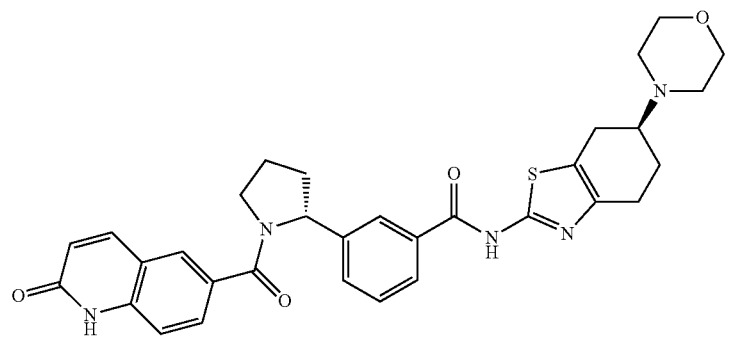 [SMILES: O=C(Nc1nc2c(s1)C[C@@H](N1CCOCC1)CC2)c1cccc([C@H]2CCCN2C(=O)c2ccc3[nH]c(=O)ccc3c2)c1] |

TABLE 1-continued

| Cpd # |
| --- |
| 127 |
| 128 |
| 129 |
| 130 |
| 131 |

TABLE 1-continued

| Cpd # |
|---|
| 132 |
| 133 |
| 134 |
| 135 |

TABLE 1-continued
Cpd #
136
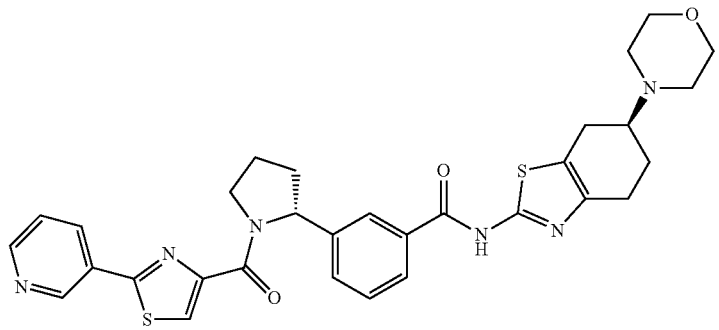 [SMILES: O=C(Nc1nc2c(s1)C[C@@H](N1CCOCC1)CC2)c1cccc([C@H]2CCCN2C(=O)c2csc(-c3cccnc3)n2)c1]
137
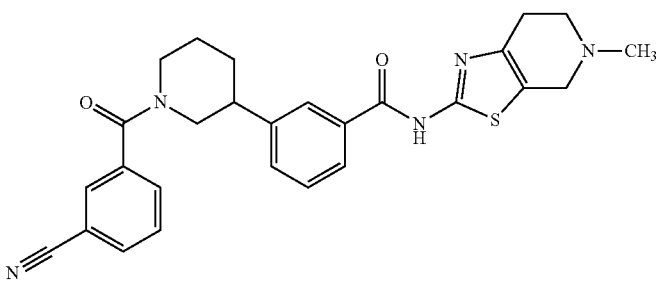 [SMILES: CN1CCc2nc(NC(=O)c3cccc(C4CCCN(C(=O)c5cccc(C#N)c5)C4)c3)sc2C1]
138
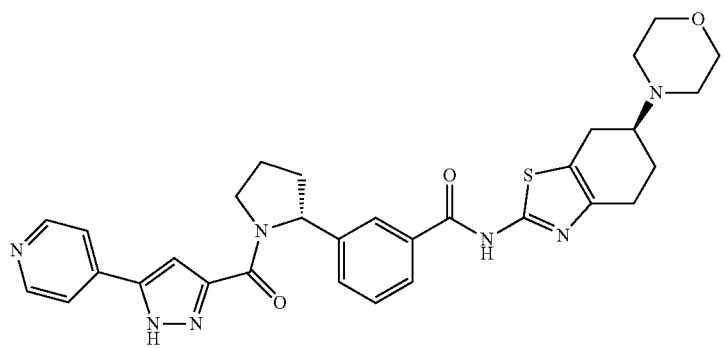 [SMILES: O=C(Nc1nc2c(s1)C[C@@H](N1CCOCC1)CC2)c1cccc([C@H]2CCCN2C(=O)c2cc(-c3ccncc3)[nH]n2)c1]
139
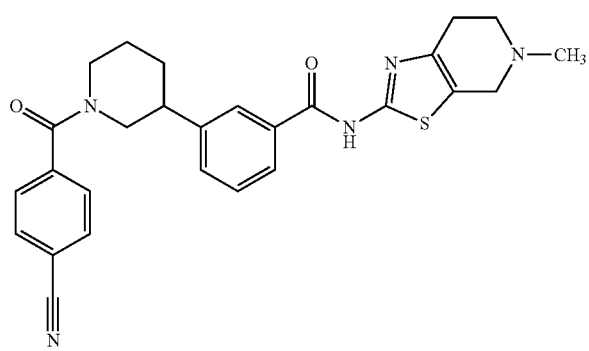 [SMILES: CN1CCc2nc(NC(=O)c3cccc(C4CCCN(C(=O)c5ccc(C#N)cc5)C4)c3)sc2C1]

TABLE 1-continued
| Cpd # | |
|---|---|
| 140 | 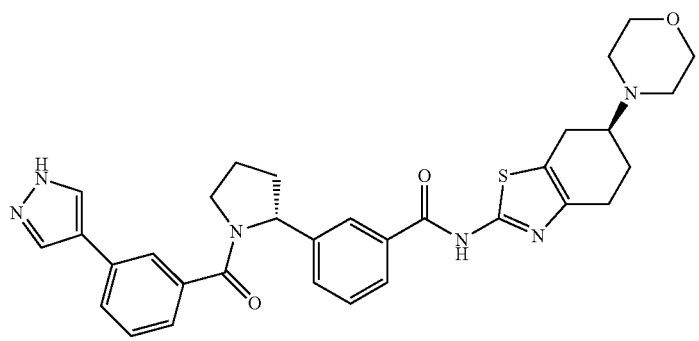 [SMILES: O=C(Nc1nc2c(s1)C[C@@H](N1CCOCC1)CC2)c1cccc([C@H]2CCCN2C(=O)c2cccc(-c3cn[nH]c3)c2)c1] |
| 141 | 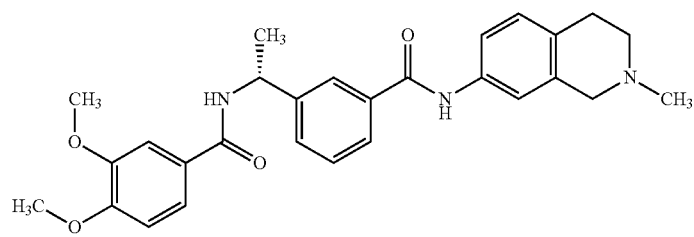 |
| 142 | 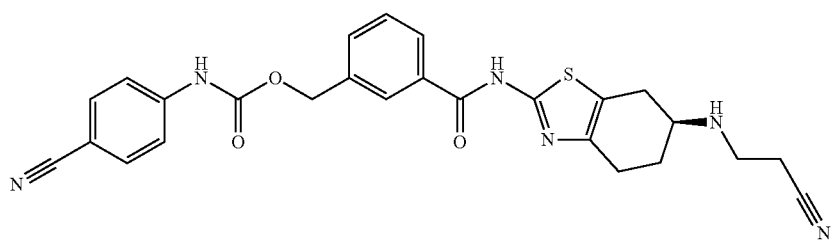 [SMILES: N#CCCN[C@H]1CCc2nc(NC(=O)c3cccc(COC(=O)Nc4ccc(C#N)cc4)c3)sc2C1] |
| 143 | 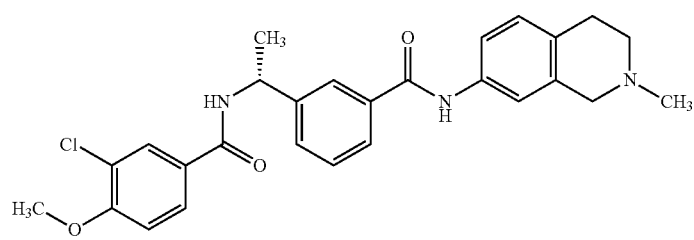 |
| 144 | 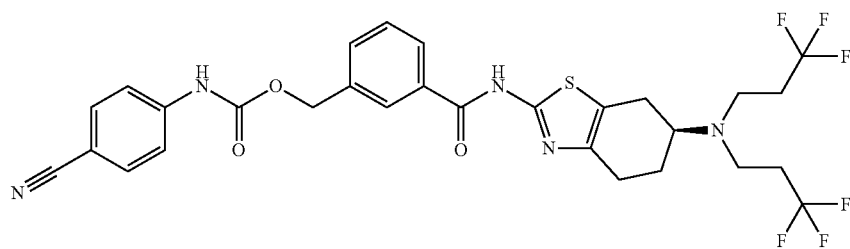 [SMILES: N#Cc1ccc(NC(=O)OCc2cccc(C(=O)Nc3nc4c(s3)C[C@@H](N(CCC(F)(F)F)CCC(F)(F)F)CC4)c2)cc1] |
| 145 | 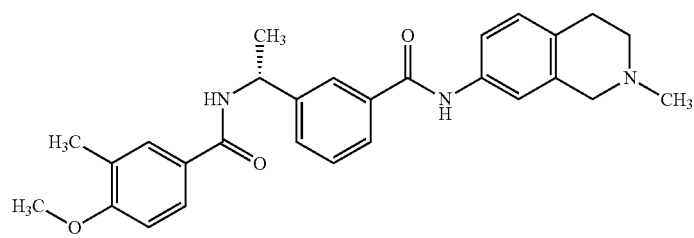 |

TABLE 1-continued
Cpd #
146
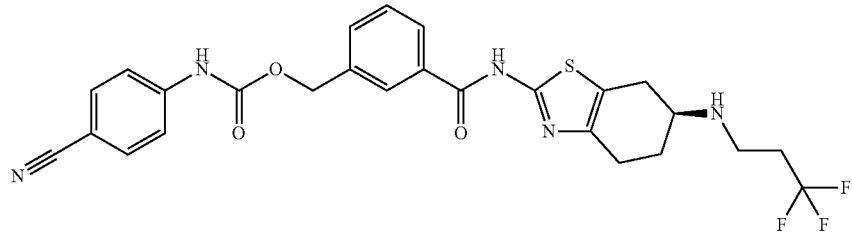 [SMILES: N#Cc1ccc(NC(=O)OCc2cccc(C(=O)Nc3nc4c(s3)C[C@@H](NCCC(F)(F)F)CC4)c2)cc1]
147
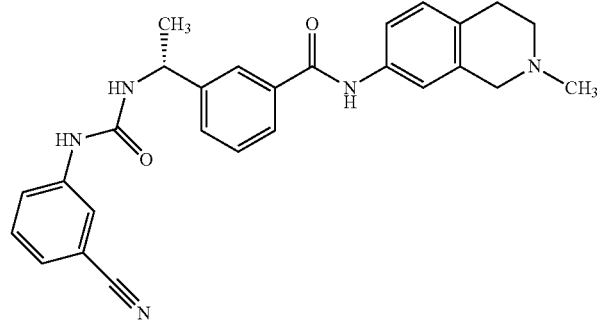 [SMILES: C[C@@H](NC(=O)Nc1cccc(C#N)c1)c1cccc(C(=O)Nc2ccc3c(c2)CN(C)CC3)c1]
148
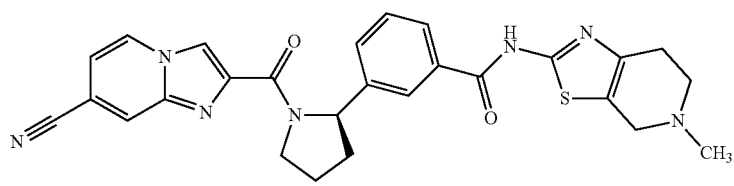 [SMILES: CN1CCc2nc(NC(=O)c3cccc([C@H]4CCCN4C(=O)c4cn5ccc(C#N)cc5n4)c3)sc2C1]
149
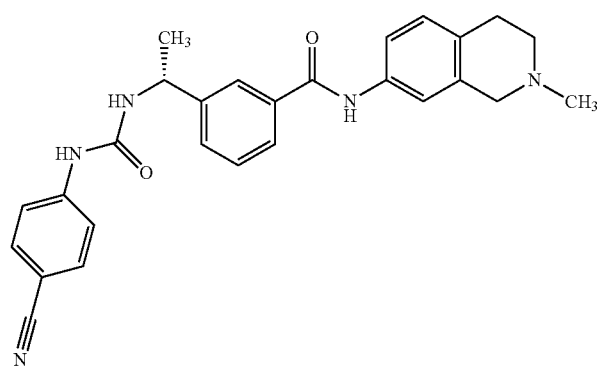 [SMILES: C[C@@H](NC(=O)Nc1ccc(C#N)cc1)c1cccc(C(=O)Nc2ccc3c(c2)CN(C)CC3)c1]
150

TABLE 1-continued
| Cpd # | |
|---|---|
| 151 | 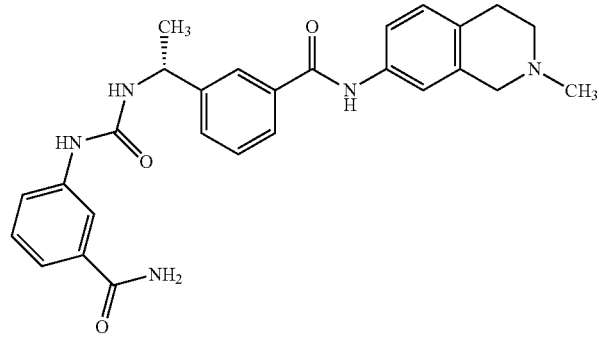 [SMILES: C[C@@H](NC(=O)Nc1cccc(C(N)=O)c1)c1cccc(C(=O)Nc2ccc3c(c2)CN(C)CC3)c1] |
| 152 | 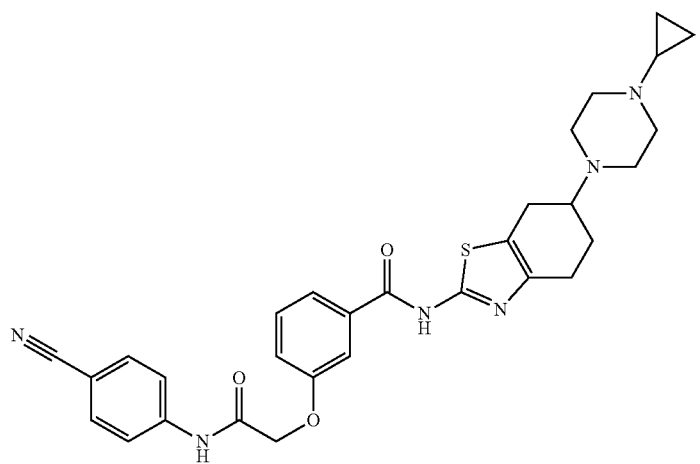 [SMILES: N#Cc1ccc(NC(=O)COc2cccc(C(=O)Nc3nc4c(s3)CC(N3CCN(C5CC5)CC3)CC4)c2)cc1] |
| 153 | 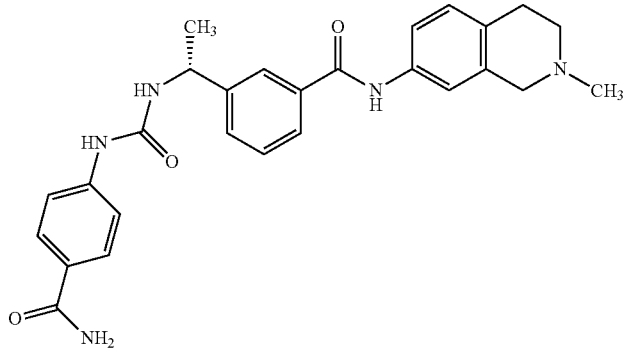 [SMILES: C[C@@H](NC(=O)Nc1ccc(C(N)=O)cc1)c1cccc(C(=O)Nc2ccc3c(c2)CN(C)CC3)c1] |
| 154 | 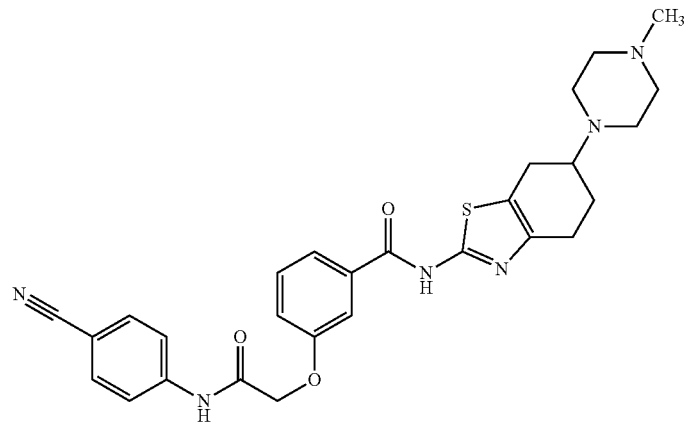 [SMILES: CN1CCN(C2CCc3nc(NC(=O)c4cccc(OCC(=O)Nc5ccc(C#N)cc5)c4)sc3C2)CC1] |

TABLE 1-continued

| Cpd # | |
|---|---|
| 155 | 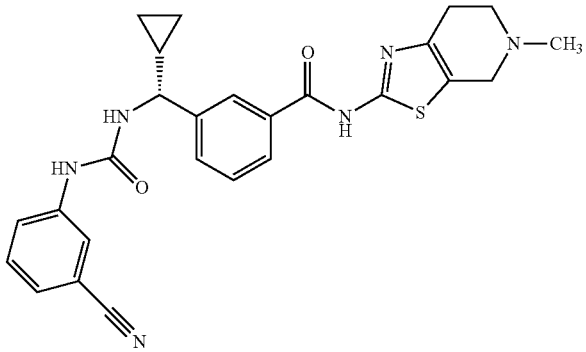 [SMILES: CN1CCc2nc(NC(=O)c3cccc([C@H](NC(=O)Nc4cccc(C#N)c4)C4CC4)c3)sc2C1] |
| 156 | 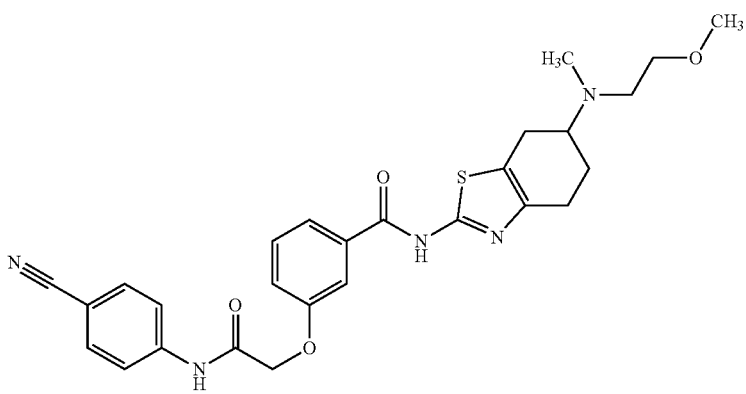 [SMILES: COCCN(C)C1CCc2nc(NC(=O)c3cccc(OCC(=O)Nc4ccc(C#N)cc4)c3)sc2C1] |
| 157 | 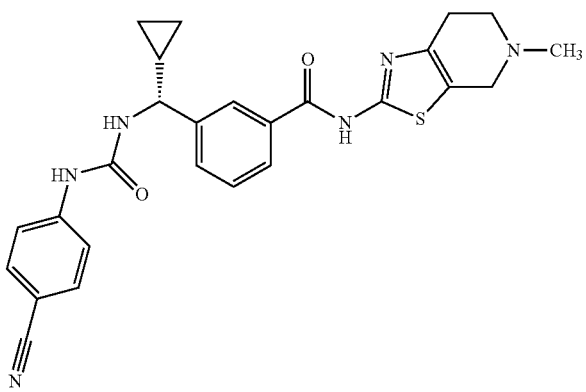 [SMILES: CN1CCc2nc(NC(=O)c3cccc([C@H](NC(=O)Nc4ccc(C#N)cc4)C4CC4)c3)sc2C1] |

In one embodiment, the invention relates to any of the compounds depicted in Table 1 above and the pharmaceutically acceptable salts thereof.

In another embodiment, the invention relates to a compound selected from compounds 1, 2, 4, 5, 8-16, 18-24, 26, 28-40, 42, 44, 46-48, 50, 52-61, 64, 66, 70, 74, 77, 78, 81-86, 88-90, 92-94, 96-98, 100-102, 104-106, 108-112, 114-118, 120, 122, 124, 126, 128, 130, 132, 134, 136, 138, 140-143, 145-150 and 152-157 in Table 1, and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—R$_a$ may be represented as phenyl-S(O)$_m$— when R$_a$ is phenyl and where m is 0, 1 or 2.

General Synthetic Methods

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carbocylic acid and an amine in the presence of 1-(3-dimethylaminopropyl)-3-ethylcarbodiimide (EDC) and 1-hydroxybenzotriazole. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of formula I.

Compounds of formula I having X=

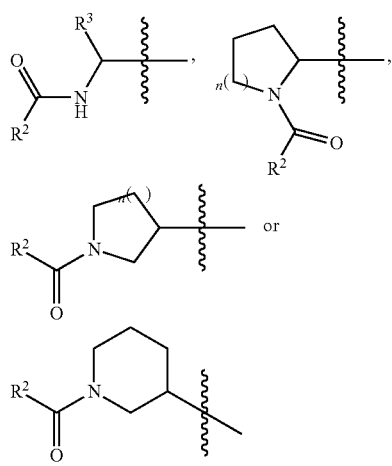

may be prepared as described in Scheme 1 for

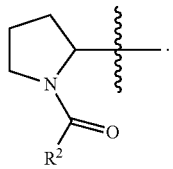

As shown in Scheme 1, a benzoic acid ester, where R'=alkyl such as methyl or ethyl, bearing the amine portion of X lacking the amide forming $R^2C(O)$— group is reacted with $R^2CO_2H$ under standard coupling conditions such as stifling in the presence of a suitable coupling agent such as 1,1'-carbonyldiimidazole (CDI) in a suitable solvent such as DMF to provide the amide intermediate III. Hydrolysis of the ester, for example by treatment with aqueous base, followed by coupling with $R^1NH_2$ provides the desired compound of formula I. Alternatively, the coupling reactions may be performed in the reverse order beginning with intermediate IV, where PG is a suitable amine protecting group such as a t-butoxycarbonyl (t-Boc) group, and coupling with $R^1NH_2$. This is followed by deprotection of the amine, for example by treatment with HCl for a t-Boc protecting group, and coupling with $R^2CO_2H$.

Scheme 2 illustrates a method for synthesis of compounds of formula I having X=

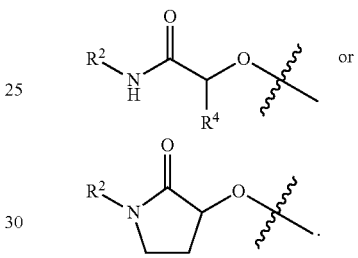

As illustrated below, the phenol ester VI (R' defined as above) is reacted with intermediate V (or the analogous intermediate for X=the pyrrolidone) where LG is a suitable group such as Br or OH and PG is an acid protecting group such as a t-Boc group, either under basic conditions if LG is Br, such as $K_2CO_3$ in DMF for a displacement reaction or, if LG is OH, the reaction is run in the presence of diethyl azodicarboxylate (DEAD) and triphenylphosphine, in a suitable solvent such as THF to provide the ether intermediate VII. Selective deprotection of the PG bearing ester, for example by treatment with

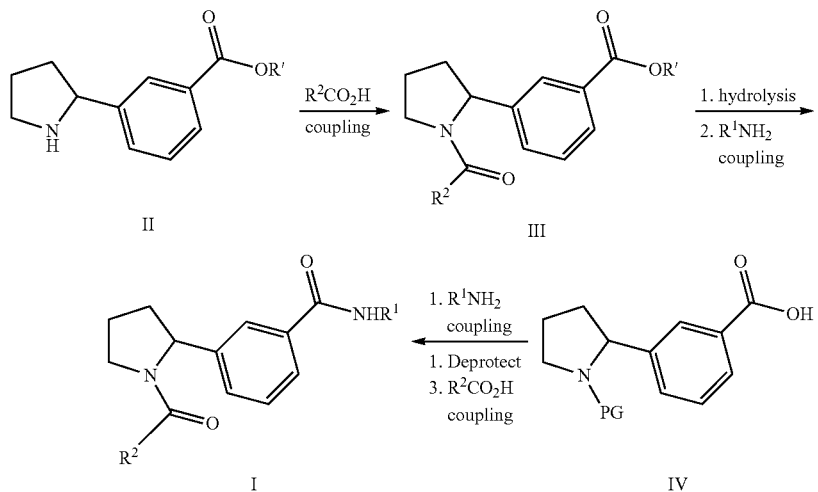

HCl if PG is a t-Boc group, followed by coupling with the desired $R^2NH_2$ and then hydrolysis of the remaining ester followed by coupling with $R^1NH_2$ provides the desired compound of formula I.

Scheme 2

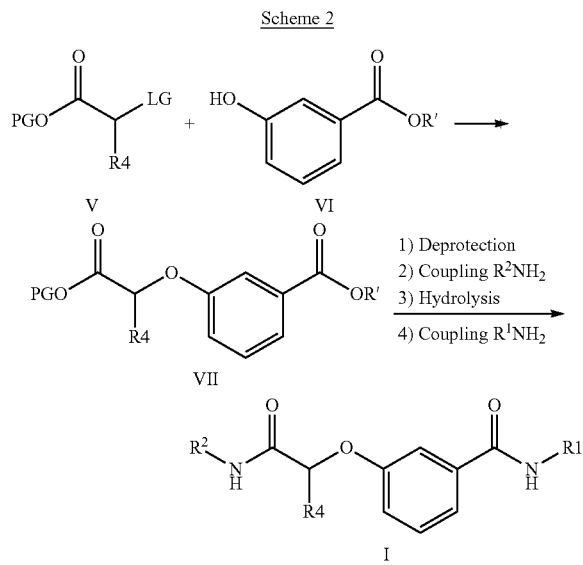

Compounds of formula I having X=

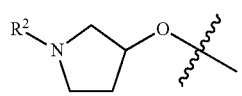

may be prepared as illustrated in Scheme 3.

Scheme 3

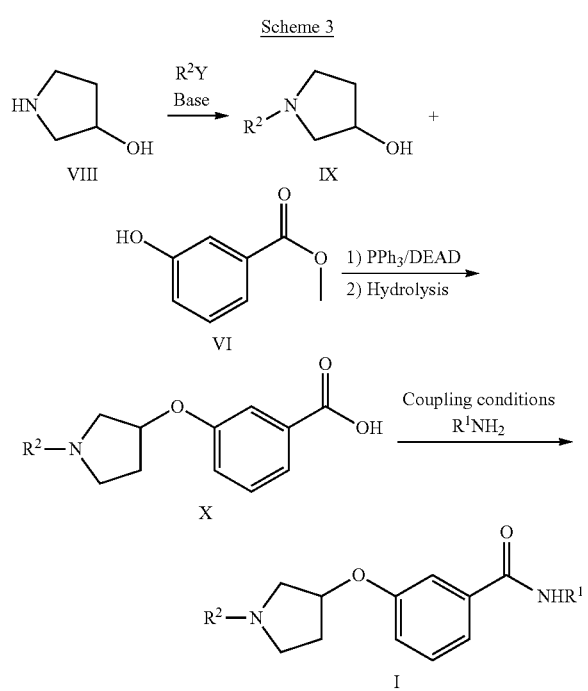

As illustrated above, 3-hydroxypyrrolidine VIII is reacted with $R^2Y$, where Y is a halogen such as Cl, Br or I, in the presence of a suitable base such as $K_2CO_3$ in a suitable solvent such as DMSO to provide IX. Intermediate IX is reacted with VI in the presence of DEAD and $PPh_3$, followed by hydrolysis of the ester, for example by treatment with aqueous base, to provide X. Reaction of intermediate X with $R^1NH_2$ under standard coupling conditions provides the desired compound of formula I.

The synthesis of compounds having X=

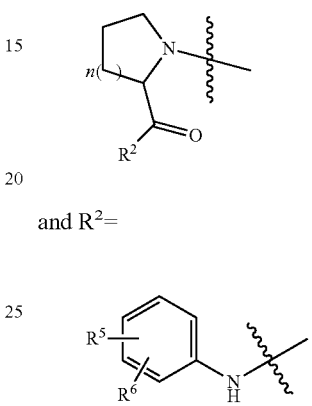

and $R^2=$

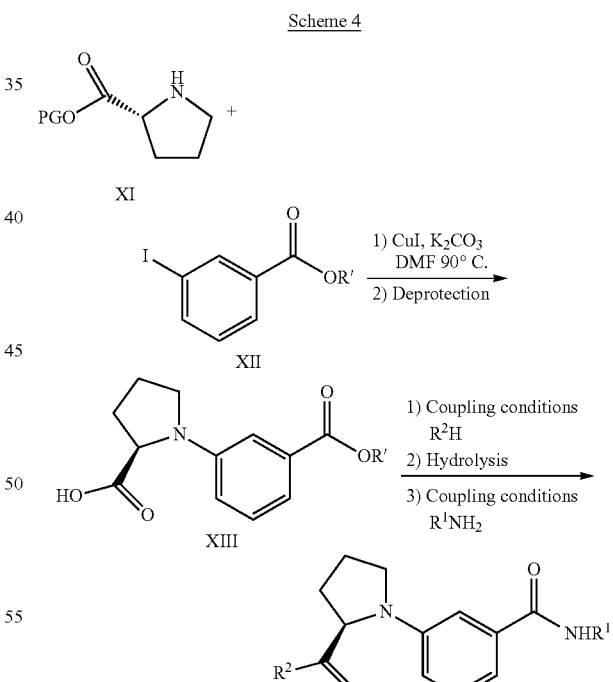

is illustrated in Scheme 4 for the n=1 intermediate XI.

As illustrated above, intermediate XI, where PG is a suitable protecting group, such as a t-Boc group, is coupled with intermediate XII (R' is as defined above) by treatment with CuI the presence of a suitable base such as $K_2CO_3$ in DMF at about 90° C. This is followed by deprotection of the carboxylic acid to provide XIII. Intermediate XIII is then coupled with the amine R²H. Hydrolysis of the ester is followed by coupling with R¹NH₂ to provide the desired compound of formula I.

Compounds of formula I having X=

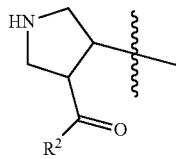

and R²=

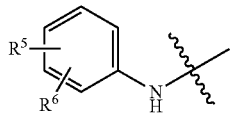

may be prepared as illustrated in Scheme 5.

Scheme 5

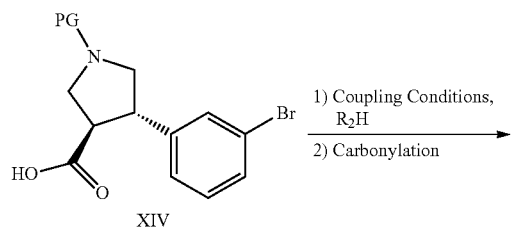

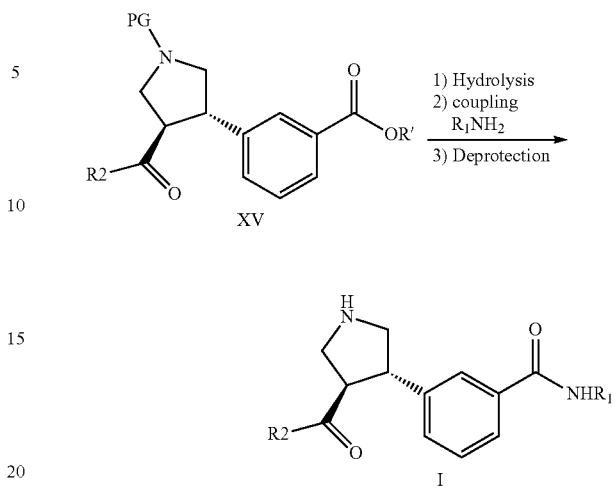

As illustrated above, intermediate XIV, where PG is an amine protecting group, such as a t-Boc group, is coupled with the amine R₂H followed by a carbonylation reaction, for example by reaction with molybedinum hexacarbonyl in the presence of a suitable base such as N,N-diisoproylethyl amine and Herrmann's palladacycle, in a suitable solvent such as MeOH/THF, in a microwave reactor to provide XV. Hydrolysis of the ester, followed by coupling with R₁NH₂ and then deprotection of the amine, for example by treatment with HCl for a t-Boc protecting group, provides the desired compound of formula I.

All of the compounds in Table I were prepared by the methods illustrated above and in the Synthetic Examples section below.

Retention times (RT) reported for compounds in the Synthetic Examples section were obtained using one of the following methods:

| HPLC Method | Time (min) | Mobile Phase | | Flow (mL/min) | Column |
|---|---|---|---|---|---|
| | | H₂O (0.1% FA) | CH₃CN (0.1% FA) | | |
| A1 | 0 | 95 | 5 | 2.5 | Agilent Zorbax C18 SB |
| | 1.7 | 5 | 95 | 2.5 | 3.5 um 4.6 × 30 mm cartridge |
| | 2 | 5 | 95 | 2.5 | |
| | 2.1 | 95 | 5 | 2.5 | |
| | 2.3 | 95 | 5 | 2.5 | |
| B1 | 0 | 70 | 30 | 2.5 | Agilent Zorbax C18 SB |
| | 1.7 | 5 | 95 | 2.5 | 3.5 um 4.6 × 30 mm cartridge |
| | 2 | 5 | 95 | 2.5 | |
| | 2.1 | 70 | 30 | 2.5 | |
| | 2.3 | 70 | 30 | 2.5 | |
| C1 | 0 | 99 | 1 | 2.5 | Agilent Zorbax C18 SB |
| | 1.7 | 50 | 50 | 2.5 | 3.5 um 4.6 × 30 mm cartridge |
| | 2 | 5 | 95 | 2.5 | |
| | 2.1 | 5 | 95 | 2.5 | |
| | 2.3 | 99 | 1 | 2.5 | |
| D1 | 0 | 95 | 5 | 1.5 | Agilent Zorbax Eclipse |
| | 7 | 5 | 95 | 1.5 | XDB-C8 5 um 4.6 × 150 mm |
| | 9 | 5 | 95 | 1.5 | |
| | 9.3 | 95 | 5 | 1.5 | |
| | 10 | 95 | 5 | 1.5 | |

| HPLC Method | Time (min) | 95% H₂O + 5% CH₃CN (0.05% Formic Acid) | CH₃CN (0.05% Formic Acid) | Flow (mL/min) | Column |
|---|---|---|---|---|---|
| C2 | 0 | 99 | 1 | 2.5 | Agilent Zorbax C18 SB |
|    | 1.6 | 80 | 20 | 2.5 | 3.5 um 4.6 × 30 mm cartridge |
|    | 1.7 | 5 | 95 | 2.5 | |
|    | 2 | 5 | 95 | 2.5 | |
|    | 2.1 | 99 | 1 | 2.5 | |
|    | 2.3 | 99 | 1 | 2.5 | |
| D2 | 0 | 99 | 1 | 1.5 | Agilent Zorbax Eclipse |
|    | 2 | 80 | 20 | 1.5 | XDB-C8 5 um 4.6 × 150 mm column |
|    | 7 | 5 | 95 | 1.5 | |
|    | 9 | 5 | 95 | 1.5 | |
|    | 9.3 | 99 | 1 | 1.5 | |
|    | 10 | 99 | 1 | 1.5 | |
| A3 | 0 | 88 | 12 | 1.5 | Agilent SB-C18 1.8 um |
|    | 0.25 | 70 | 30 | 1.5 | 3 × 50 mm column |
|    | 0.3 | 60 | 40 | 1.5 | |
|    | 1.19 | 5 | 95 | 1.5 | |
|    | 1.75 | 0 | 100 | 1.5 | |
| B3 | 0 | 60 | 40 | 1.5 | Agilent Eclipse C8 |
|    | 1.19 | 15 | 85 | 1.5 | 1.8 um 3 × 50 mm column |
|    | 1.75 | 0 | 100 | 1.5 | |
| C3 | 0 | 95 | 5 | 1.5 | Agilent SB-AQ 1.8 um |
|    | 0.25 | 50 | 50 | 1.5 | 3 × 50 mm column |
|    | 0.3 | 70 | 30 | 1.5 | |
|    | 1.3 | 10 | 90 | 1.5 | |
|    | 1.7 | 0 | 100 | 1.5 | |
| D3 | 0 | 95 | 5 | 1.5 | Agilent SB-C18 1.8 um |
|    | 3.8 | 10 | 90 | 1.5 | 3 × 50 mm column |
|    | 4.5 | 0 | 100 | 1.5 | |
| E  | 0 | 90 | 10 | 0.8 | BEH 2.1 × 50 mm C18, |
|    | 1.19 | 5 | 95 | 0.8 | 1.7 um particle diameter |
|    | 1.7 | 5 | 95 | 0.8 | |

SYNTHETIC EXAMPLES

Compound numbers in the following Examples refer to the compound numbers in Table 1.

Example 1

Synthesis of (R)-2-[3-((S)-6-propylamino-4,5,6,7-tetrahydro-benzothiazol-2-ylcarbamoyl)-phenyl]-pyrrolidine-1-carboxylic acid (3-cyano-phenyl)-amide (Compound 29)

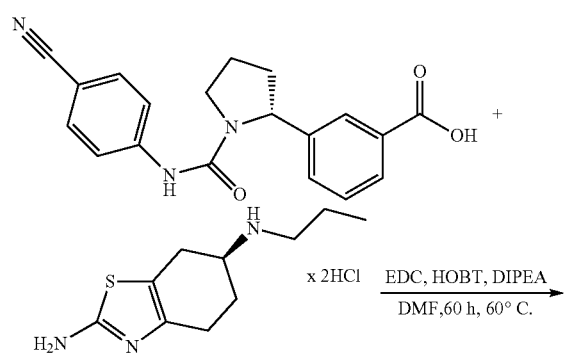

x 2HCl  EDC, HOBT, DIPEA
―――――――――――
DMF, 60 h, 60° C.

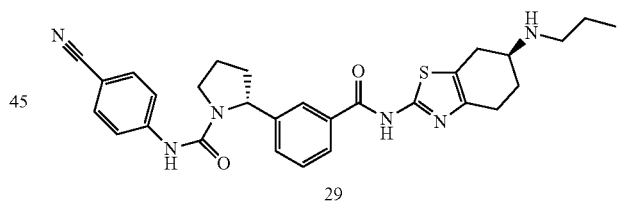

29

Dissolve 3-[(R)-1-(4-cyano-phenylcarbamoyl)-pyrrolidin-2-yl]-benzoic acid (158 mg, 0.47 mmol), EDC (165 mg, 0.86 mmol) and HOBT (125 mg, 0.82 mmol) into 3 mL of DMF. Stir mixture for 1 h. Add (S)—N-6-propyl-4,5,6,7-tetrahydro-benzothiazole-2,6-diamine dihydrochloride (150 mg, 0.52 mmol) to the mixture and place in a 60° C. bath with an Ar stream blowing over it. Stir mixture for 14 h resulting in a concentrated residue. LC-MS analysis indicates the desired product. Dissolve into 5 mL of DMF and purify via the Gilson Prep HPLC system (5%-70% CH₃CN/H₂O) to give a mixture of products. Apply to a SiO₂ prep plate. Elute with (10% MeOH/1% NH₃/CH₂Cl₂) to give 47.3 mg of the title compound. MS, electrospray 529.57 (M+H), rt 4.33 min.

The following compounds are prepared according to the procedure described in Example 1, using the appropriate starting materials:

Compound 37: MS, electrospray 515.81 (M+H), rt 7.12 min.

Compound 39: MS, electrospray 558.01 (M+H), rt 1.33 min.

Example 2

Synthesis of 3,4-dimethoxy-N-{(R)-1-[3-((S)-6-propylamino-4,5,6,7-tetrahydro-benzothiazol-2-ylcarbamoyl)-phenyl]-ethyl}-benzamide (Compound 31)

Synthesis of 3-[(S)-1-(4-Cyano-phenyl)-pyrrolidin-3-yloxy]-N-(5-methyl-4,5,6,7-tetrahydro-thiazolo[5,4-c]pyridin-2-yl)-benzamide (Compound 41)

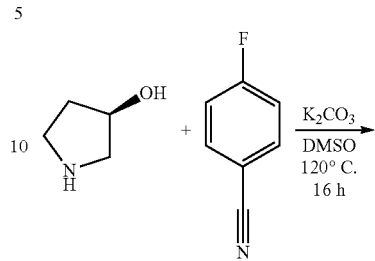

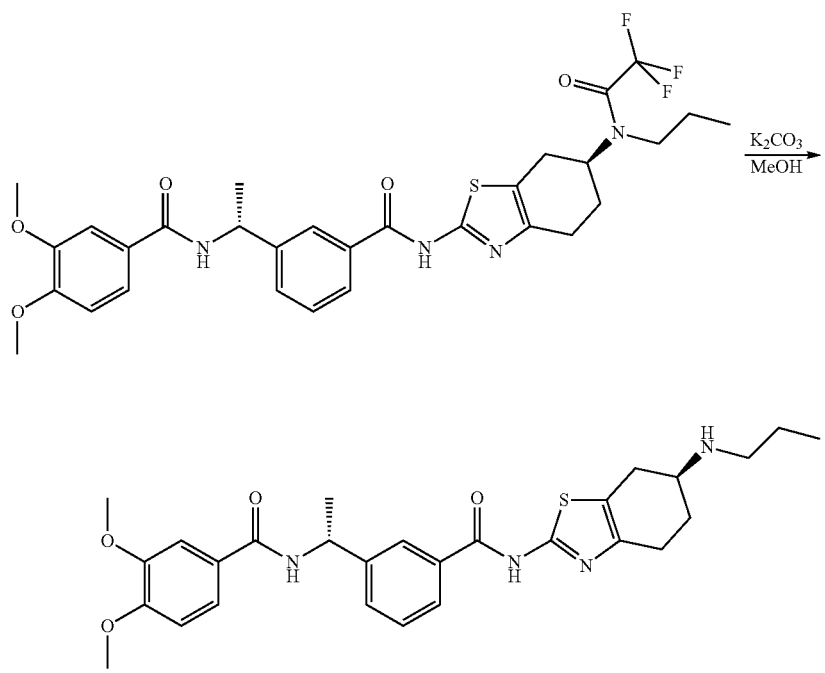

Dissolve 3,4-dimethoxy-N—[(R)-1-(3-{(S)-6-[propyl-(2,2,2-trifluoro-acetyl)-amino]-4,5,6,7-tetrahydro-benzothiazol-2-ylcarbamoyl}-phenyl)-ethyl]-benzamide (109 mg, 0.18 mmol) into 10 mL of MeOH and add 5 mL of H$_2$O. To this add K$_2$CO$_3$ (200 mg, 1.50 mmol) and heat the mixture overnight at 55° C. LC-MS analysis indicates the desired material. Add trifluoroacetic acid, dissolve into MeOH and purify via the Gilson Prep HPLC system (5%-70% CH$_3$CN/H$_2$O) to give 62.6 mg of the title compound. MS, electrospray 523.67 (M+H), rt 1.14 min.

The following compounds are prepared according to the procedure in Example 2, using the appropriate starting materials:

Compound 33: MS, electrospray 527.61 (M+H), rt 1.27 min.

Compound 35: MS, electrospray 507.67 (M+H), rt 1.24 min.

-continued

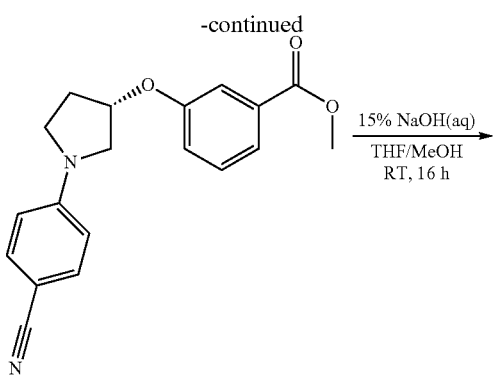

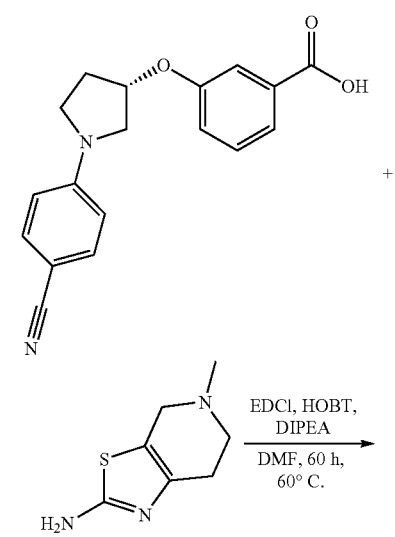

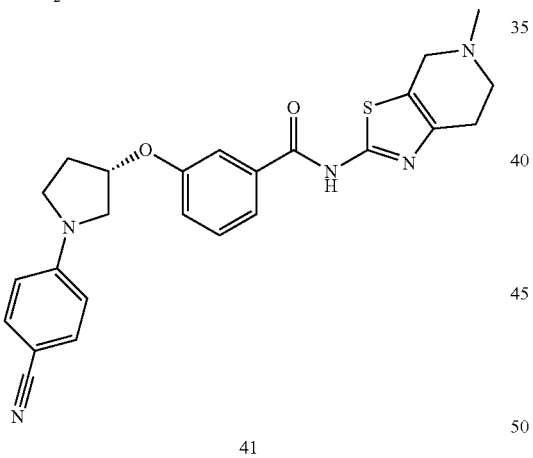

the mixture to dryness. Dissolve residue into CH₂Cl₂ and apply to a 2 mm SiO₂ prep plate. Elute with 50% EtOAc/hexanes to give 113 mg of slightly impure 3-[(S)-1-(4-cyano-phenyl)-pyrrolidin-3-yloxy]-benzoic acid methyl ester.

Dissolve to 3-[(S)-1-(4-cyano-phenyl)-pyrrolidin-3-yloxy]-benzoic acid methyl ester (113 mg, 0.35 mmol) into 1:1 mixture of THF/MeOH (4 mL). Add 15% NaOH solution. and stir mixture overnight at room temperature. LC-MS analysis indicates the desired product. Concentrate the mixture to dryness. Suspend the residue in 5 mL of H₂O and make the mixture acidic by the addition of 5% HCl. Filter the precipitate and dry to give 82.6 mg of 3-[(S)-1-(4-cyano-phenyl)-pyrrolidin-3-yloxy]-benzoic acid.

Dissolve 3-[(S)-1-(4-cyano-phenyl)-pyrrolidin-3-yloxy]-benzoic acid (80.2 mg, 0.26 mmol), EDC (99.2 mg, 0.52 mmol) and HOBT (79.6 mg, 0.52 mmol) into 2 mL of DMF. The mixture is stirred for 1 h. Add 5-methyl-4,5,6,7-tetrahydro-thiazolo[5,4-c]pyridin-2-ylamine (46.5 mg, 0.28 mmol) to the mixture and place in a 60° C. bath with an Ar stream blowing over it. Stir mixture for 14 h resulting in a concentrated residue. LC-MS analysis indicates the desired product. Dissolve into 5 mL of DMF and purify via the Gilson Prep HPLC system (5%-80% CH₃CN/H₂O) to give 59.4 mg of the title compound, MS, electrospray 560.58 (M+H), rt 6.01 min.

The following compound is prepared according to the procedure in Example 3, using the appropriate starting materials:

Compound 43: MS, electrospray 560.51 (M+H), rt 5.96 min.

Example 4

Synthesis of 3-[(3-cyano-phenylcarbamoyl)-methoxy]-N-(5-methyl-4,5,6,7-tetrahydro-thiazolo[5,4-c]pyridin-2-yl)-benzamide (Compound 3)

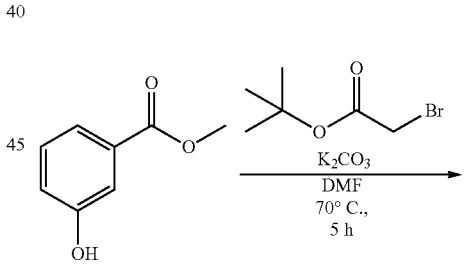

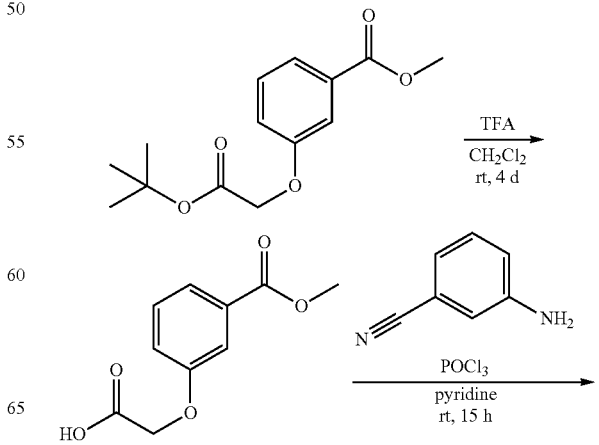

Dissolve (R)-pyrrolidin-3-ol (0.08 mL, 1.00 mmol) and 4-fluorobenzonitrile (121 mg, 1.00 mmol) into 1 mL of DMSO. Add K₂CO₃ (276 mg, 2.00 mmol) and heat the mixture at 120° C. for 16 h. LC-MS analysis indicates the desired intermediate. Add 10 mL of H₂O. Filter the precipitate and dry in a Buchner funnel for 1 h to give 188 mg of 4-((R)-3-hydroxy-pyrrolidin-1-yl)-benzonitrile.

Dissolve 4-((R)-3-hydroxy-pyrrolidin-1-yl)-benzonitrile (188 mg, 1.00 mmol), triphenylphosphine (393 mg, 1.50 mmol) and 3-hydroxy-benzoic acid methyl ester (228 mg, 1.5 mmol) into 10 mL of dry THF under Ar. Cooled to 4° C. Add DEAD (0.26 mL, 1.50 mmol) in a drop-wise fashion. Stir mixture with warming to room temperature overnight. LC-MS analysis indicates the desired intermediate. Concentrate -continued

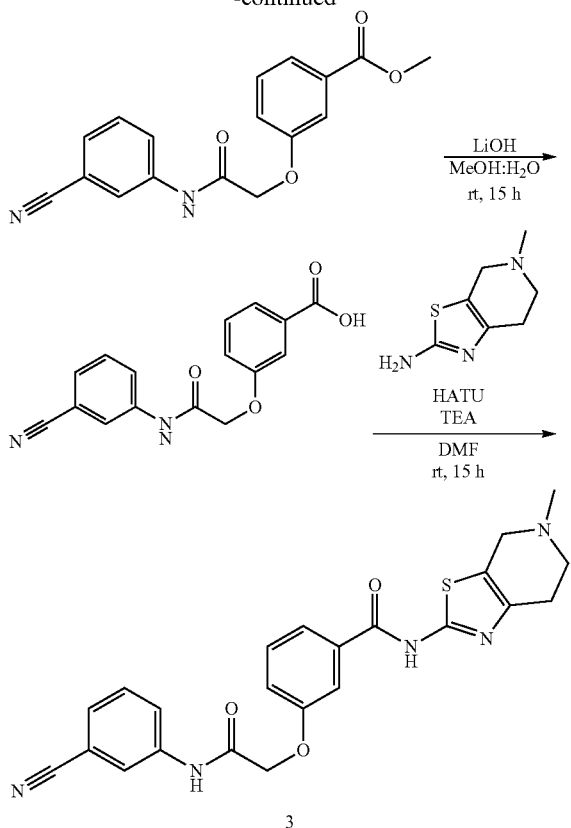

To a solution of methyl 3-hydroxybenzoate (1.00 g, 6.57 mmol) in N,N-dimethylformamide (60 mL) add tert-butyl bromoacetate (1.10 mL, 7.44 mmol) followed by potassium carbonate (4.0 g, 29 mmol) of. Heat the mixture at 70° C. for 5 hours, Cool to room temperature and pour over ice. Allow the mixture to sit until all of the ice melts during which time a solid precipitates from solution. Collect the white solid by filtration, wash with water and dry on the filter pad to provide 1.49 g of 3-tert-butoxycarbonylmethoxy-benzoic acid methyl ester.

To a solution of 3-tert-butoxycarbonylmethoxy-benzoic acid methyl ester (1.00 g, 3.75 mmol) in methylene chloride (4 mL), add trifluoroacetic acid (0.50 mL, 6.6 mmol). Stir the mixture overnight at room temperature in an open vial to allow the solvent to escape. Add an additional portion of trifluoroacetic acid (0.50 mL, 6.6 mmol) and stir the reaction mixture for an additional 24 hours. Add an additional portion of trifluoroacetic acid (1.50 mL, 19.8 mmol) and stir the reaction at room temperature for 3 days. Concentrate under reduced pressure to provide 0.750 g (95.0%) of 3-carboxymethoxy-benzoic acid methyl ester as a light brown solid.

Cool a solution of 3-aminobenzonitrile (0.35 g, 2.96 mmol) in pyridine (6 mL), to 0° C., and add 3-carboxymethoxy-benzoic acid methyl ester (0.75 g, 3.57 mmol) followed by phosphorous oxychloride (0.34 mL, 3.6 mmol). Warm the mixture to room temperature and stir for 15 hours. Dilute the mixture with water causing a material to oil out of solution. Add MeOH and stir the mixture vigorously causing a solid to slowly form. Collect the solid by filtration, wash with water and dry on the filter pad to provide 0.940 g of 3-[(3-cyano-phenylcarbamoyl)-methoxy]-benzoic acid methyl ester.

Add lithium hydroxide (0.15 g, 6.3 mmol) to a suspension of 3-[(3-cyano-phenylcarbamoyl)-methoxy]-benzoic acid methyl ester (0.94 g, 3.1 mmol) in a 1:1 mixture of MeOH:water (30 mL). Stir the mixture at room temperature for 15 h then adjust the pH of the reaction to slightly acidic by the addition of a 2 N solution of hydrochloric acid. A solid precipitates from solution. Collect by filtration, wash with water, and dry on the filter pad to provide 0.650 g of 3-[(3-cyano-phenylcarbamoyl)-methoxy]-benzoic acid as a solid.

Add 5-methyl-4,5,6,7-tetrahydro-thiazolo[5,4-c]pyridin-2-ylamine (0.03 g, 0.18 mmol) followed by O-(7-azabenzotriazole-1-yl)-N,N,N',N'-tetramethyl uranium hexafluorophosphate (0.07 g, 0.18 mmol) and N,N-diisopropylethyl amine (0.10 mL, 0.54 mmol) to a solution of 3-[(3-cyano-phenylcarbamoyl)-methoxy]-benzoic acid (0.05 g, 0.17 mmol) in N,N-dimethylformamide (2 mL). Sir the mixture at room temperature for 15 h then dilute with water causing a solid to precipitate from solution. Collect the solid by filtration, wash with water and dry on the filter pad. Triturate the crude product with methylene chloride and dry on the filter pad to provide 0.020 g of the title compound as a powder. MS, electrospray 448.96 (M+H), rt. 1.13 min.

The following compounds are prepared according to the procedure in Example 4, using the appropriate starting materials:

Compound 1. MS, electrospray 448.96 (M+H), rt. 1.23 min.

Compound 9. MS, electrospray 476.74 (M+H), rt. 1.19 min.

Compound 13. MS, electrospray 518.73 (M+H), rt. 1.25 min.

Compound 23. MS, electrospray 463.73 (M+H), rt 1.14 min.

Example 5

Synthesis of N—((S)-6-amino-4,5,6,7-tetrahydro-benzothiazol-2-yl)-3-[(4-cyano-phenylcarbamoyl)-methoxy]-benzamide (Compound 11)

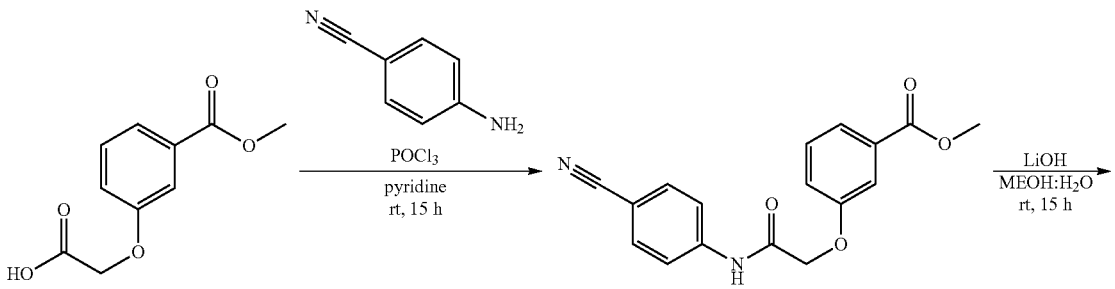

-continued

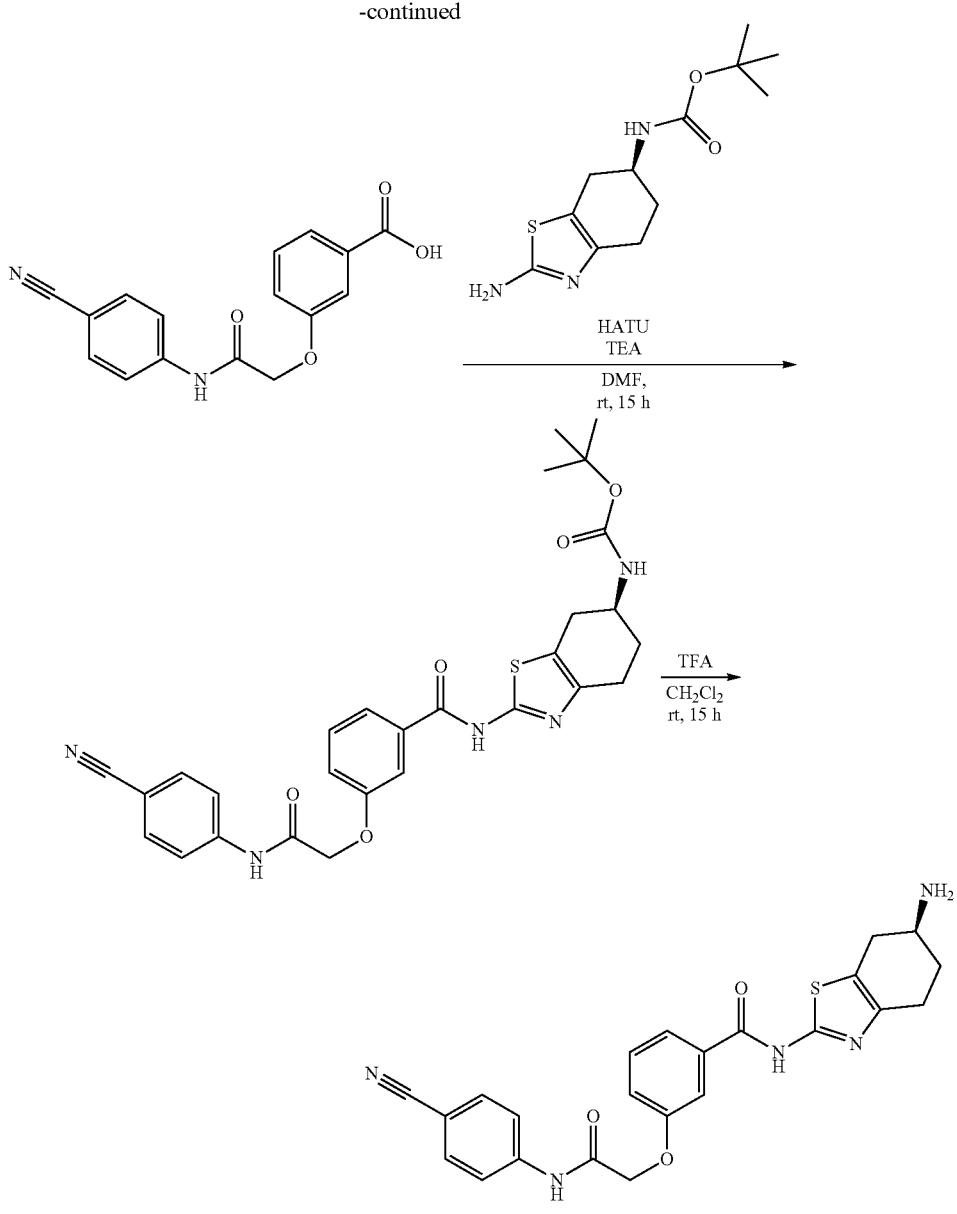

Cool a solution of 4-aminobenzonitrile (0.48 g, 4.02 mmol) in pyridine (30 mL), to 0° C., and add 3-carboxymethoxy-benzoic acid methyl ester (0.79 g, 3.76 mmol) followed by phosphorous oxychloride (0.38 mL, 4.02 mmol). Stir the mixture at 0° C. for 2 h then dilute with water causing a solid to precipitate from solution. Collect the solid by filtration, wash with water, and dry on the filter pad to provide 1.01 g (81.0%) of 3-[(4-cyano-phenylcarbamoyl)-methoxy]-benzoic acid methyl ester.

Add lithium hydroxide (0.10 g, 4.18 mmol) to a suspension of 3-[(4-cyano-phenylcarbamoyl)-methoxy]-benzoic acid methyl ester (0.50 g, 1.61 mmol) in a 1:1:1 mixture of water:MeOH: tetrahydrofuran. Stir the mixture at room temperature for 36 h then dilute with water and wash with EtOAc. Adjust the pH of the aqueous phase by the addition of a 1 N solution of hydrochloric acid. Extract the mixture with EtOAc and dry the combined organic phase over anhydrous sodium sulfate. Concentrate under reduced pressure to provide 0.290 g of 3-[(4-cyano-phenylcarbamoyl)-methoxy]-benzoic acid as a solid.

Add ((S)-2-amino-4,5,6,7-tetrahydro-benzothiazol-6-yl)-carbamic acid tert-butyl ester (0.10 g, 0.37 mmol) followed by O-(7-aza-benzotriazole-1-yl)-N,N,N'N'-tetramethyluronium hexafluorophosphate (0.13 g, 0.34 mmol) and N,N-diisopropylethyl (0.13 mL, 0.70 mmol) amine to a solution of 3-[(4-cyano-phenylcarbamoyl)-methoxy]-benzoic acid (0.10 g, 0.34 mmol) in N,N-dimethylacetamide (3 mL). Heat the mixture to 50° C. for 2 h then cool to room temperature and dilute with water causing a solid to precipitate from solution. Collect the light yellow solid by filtration, wash with water, and dry on the filter pad to provide 0.14 g of ((S)-2-{3-[(4-cyano-phenylcarbamoyl)-methoxy]-benzoylamino}-4,5,6,7-tetrahydro-benzothiazol-6-yl)-carbamic acid tert-butyl ester.

Add trifluoroacetic acid (1.0 mL, 14 mmol) to a solution of ((S)-2-{3-[(4-cyano-phenylcarbamoyl)-methoxy]-benzoylamino}-4,5,6,7-tetrahydro-benzothiazol-6-yl)-carbamic acid tert-butyl ester (0.14 g, 0.26 mmol) in methylene chloride (10 mL). Stir the mixture at room temperature for 15 h then concentrate under reduced pressure. Purify the residue by preparative reverse phase HPLC using acetonitrile/water with 0.1% trifluoroacetic acid additive as the eluent to provide 0.07 g of the title compound as a white powder. MS, electrospray 448.75 (M+H), rt. 1.21 min.

Example 6

Synthesis of (R)-1-[3-(5-methyl-4,5,6,7-tetrahydro-thiazolo[5,4-c]pyridin-2-ylcarbamoyl)-phenyl]-pyrrolidine-2-carboxylic acid (4-cyano-phenyl)-amide (Compound 5)

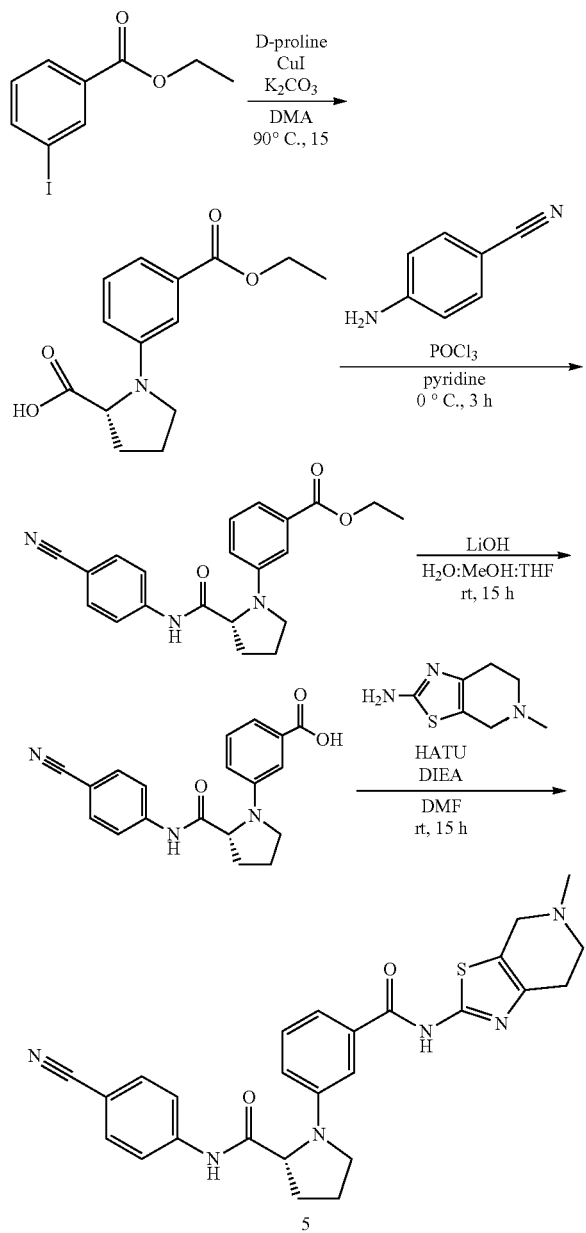

Add ethyl 3-iodobenzoate (1.5 mL, 8.9 mmol), potassium carbonate (1.3 g, 9.4 mmol) and copper (I) iodide (0.17 g, 0.89 mmol) to a solution of D-proline (1.00 g, 8.69 mmol) in N,N-dimethylacetamide (20 mL). Bubble Argon through the mixture for 30 min then heat the reaction to 90° C. for 15 hours. Cool the mixture to room temperature, dilute with water, and filter to remove insoluble material. Wash the filtrate with diethyl ether and adjust the pH of the aqueous phase to slightly acidic by the addition of a 2 N solution of hydrochloric acid. Extract the mixture with methylene chloride and wash the combined organic phase with brine. Dry over anhydrous sodium sulfate and concentrate under reduced pressure to provide an oil. Re-dissolve the material in methylene chloride and concentrate under a stream of nitrogen to provide 0.44 g (19.2%) of (R)-1-(3-ethoxycarbonyl-phenyl)-pyrrolidine-2-carboxylic acid as an oil.

Cool a solution of 4-aminobenzonitrile (0.05 g, 0.42 mmol) in pyridine (2 mL) to 0° C., and add (R)-1-(3-ethoxycarbonyl-phenyl)-pyrrolidine-2-carboxylic acid (0.10 g, 0.38 mmol), followed by phosphorous oxychloride (0.04 mL, 0.43 mmol). Stir the mixture at 0° C. for 2 h followed by addition of a second portion of phosphrous oxychloride (0.04 mL, 0.43 mmol). Stir the mixture at 0° C. for an additional 1 hour. Dilute the mixture with water and extract with EtOAc. Wash the combined organic phase with a saturated aqueous solution of sodium bicarbonate followed by a saturated aqueous solution of ammonium chloride and then brine. Dry the mixture over anhydrous sodium sulfate and concentrated under reduced pressure to provide 0.052 g of 3-[(R)-2-(4-cyano-phenylcarbamoyl)-pyrrolidin-1-yl]-benzoic acid ethyl ester as a solid.

Add lithium hydroxide (0.03 g, 1.3 mmol) to the crude 3-[(R)-2-(4-cyano-phenylcarbamoyl)-pyrrolidin-1-yl]-benzoic acid ethyl ester (0.05 g, 0.14 mmol) in a 1:1:1 mixture of water:MeOH/tetrahydrofuran (3 mL). Stir the mixture at room temperature for 15 h then wash with EtOAc. Adjust the pH of the aqueous phase to slightly acidic by the addition of a 2 N solution of hydrochloric acid. Extract the mixture with methylene chloride, dry the combined organic phase over anhydrous sodium sulfate and concentrate under a stream of nitrogen to provide 0.020 g of 3-[(R)-2-(4-cyano-phenylcarbamoyl)-pyrrolidin-1-yl]-benzoic acid as a yellow oil.

Add 5-methyl-4,5,6,7-tetrahydro-thiazolo[5,4-c]pyridin-2-ylamine (0.012 g, 0.071 mmol) followed by O-(7-azabenzotriazole-1-yl)-N,N,N',N'-tetramethyl uranium hexafluorophosphate (0.025 g, 0.066 mmol) and N,N-diisopropylethyl amine (0.04 mL, 0.20 mmol) to a solution of 3-[(R)-2-(4-cyano-phenylcarbamoyl)-pyrrolidin-1-yl]-benzoic acid (0.02 g, 0.06 mmol) in N,N-dimethylformamide (2 mL). Stir the mixture at room temperature for 15 h then dilute with water and purify by preparative reverse phase HPLC using an eluent of acetonitrile:water with 0.1% trifluoroacetic acid additive to provide 0.002 g of (R)-1-[3-(5-methyl-4,5,6,7-tetrahydro-thiazolo[5,4-c]pyridin-2-ylcarbamoyl)-phenyl]-pyrrolidine-2-carboxylic acid (4-cyano-phenyl)-amide as a solid. MS, electrospray 487.80 (M+H), rt. 1.51 min.

The following compounds are prepared according to the procedure in Example 6, using the appropriate starting materials:

Compound 7. MS, electrospray 487.80 (M+H), rt. 1.27 min.

Compound 21. MS, electrospray 487.74 (M+H), rt. 1.31 min.

Example 7

Synthesis of 3-[(R)-1-(4-cyano-phenylcarbamoyl)-ethoxy]-N-(5-methyl-4,5,6,7-tetrahydro-thiazolo[5,4-c]pyridin-2-yl)-benzamide (Compound 19)

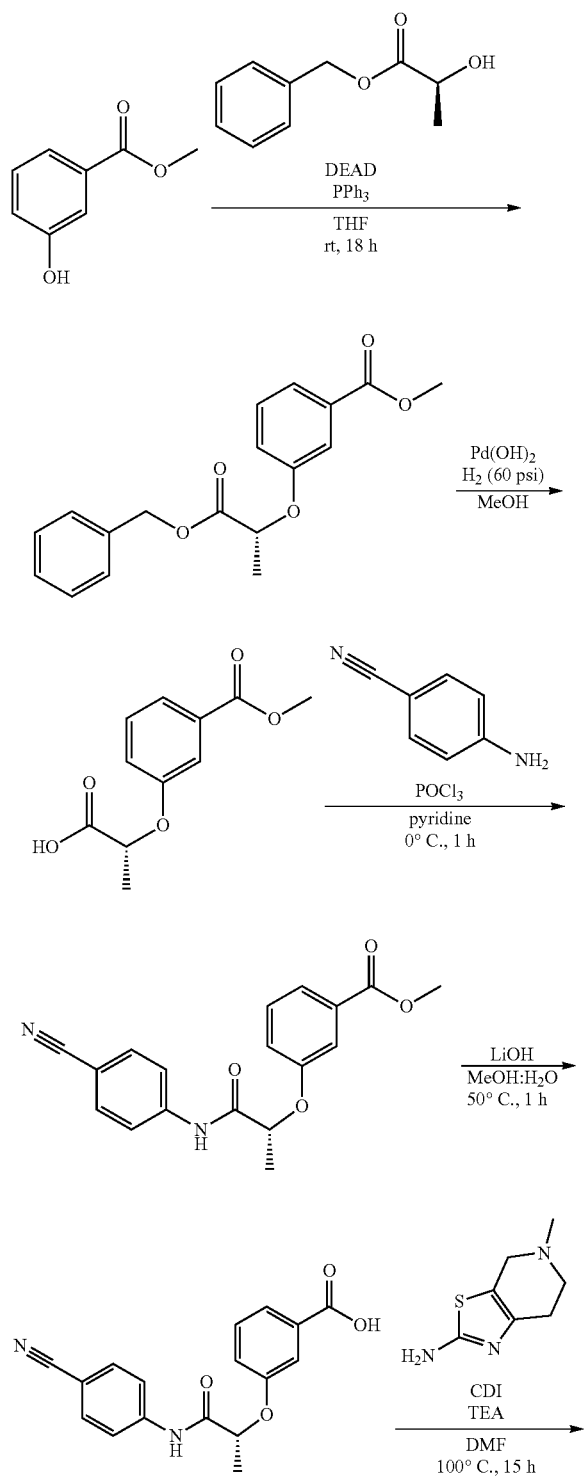

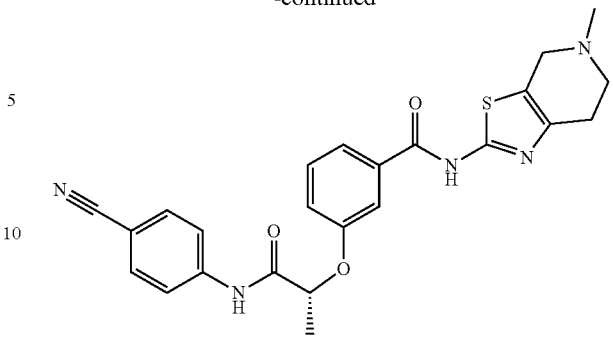

To a solution of (10.0 g, 55.5 mmol) of 3-hydroxy-benzoic acid methyl ester in tetrahydrofuran (125 mL), cooled to 0° C., is added (8.44 g, 55.5 mmol) of (S)-2-hydroxy-propionic acid benzyl ester, and (14.5 g, 55.5 mmol) of triphenyl phosphine. To this mixture is added a solution of (11.3 mL, 72.2 mmol) of diethylazodicarboxylate in tetrahydrofuran (25 mL) via a syringe pump over a 1 hour period. The reaction mixture is warmed to room temperature and stirred for 18 h then concentrated under reduced pressure. The residue is purified by flash silica gel chromatography to provide 13 g of 3-((R)-1-benzyloxycarbonyl-ethoxy)-benzoic acid methyl ester as an oil.

Add palladium hydroxide (3.0 g, 21 mmol) to a solution of 3-((R)-1-benzyloxycarbonyl-ethoxy)-benzoic acid methyl ester (14 g, 45 mmol) in MeOH (400 mL). De-gas the mixture with Argon for 10 minutes then place under 60 psi of hydrogen. Shake the vessel for 2 hours. Filter the mixture through a pad of diatomaceous earth and concentrate under reduced pressure. Triturate the residue with a mixture of hexanes and methylene chloride to provide 7.5 g of 3-((R)-1-carboxy-ethoxy)-benzoic acid methyl ester as a solid.

Cool a solution 3-((R)-1-carboxy-ethoxy)-benzoic acid methyl ester (0.50 g, 1.90 mmol) in pyridine (5 mL), to 0° C., and add 4-aminobenzonitrile (0.28 g, 2.33 mmol) followed by phosphorous oxychloride (0.22 mL, 2.4 mmol). Stir the mixture at 0° C. for 1 h then dilute with water and concentrate under reduced pressure. Purify the residue by flash silica gel chromatography to provide 0.59 g of 3-[(R)-1-(4-cyano-phenylcarbamoyl)-ethoxyl]-benzoic acid methyl ester as an oil.

Add 10% aqueous solution of sodium hydroxide (2.5 mL, 6.2 mmol) to a suspension of 3-[(R)-1-(4-cyano-phenylcarbamoyl)-ethoxy]-benzoic acid methyl ester (0.59 g, 0.81 mmol) in a 1:1 mixture of water: MeOH (20 mL). Heat the mixture at 50° C. for 1 h then cool to room temperature and adjust the pH of the mixture to approximately pH 5 by the addition of a 2 N solution of hydrochloric acid. Extract the mixture with EtOAc and wash the combined organic phase with brine, dry over anhydrous sodium sulfate and concentrate under reduced pressure to provide 0.55 g of 3-[(R)-1-(4-cyano-phenylcarbamoyl)-ethoxy]-benzoic acid as a foam.

Add 1,1-carbonyldiimdazole (0.10 g, 0.62 mmol) followed by N,N-diisopropylethylamine (0.27 mL, 1.5 mmol) to a solution of 3-[(R)-1-(4-cyano-phenylcarbamoyl)-ethoxy]-benzoic acid (0.18 g, 0.58 mmol) in dimethylacetamide (4 mL). Stir the mixture at room temperature for 1 h then add 5-methyl-4,5,6,7-tetrahydro-thiazolo[5,4-c]pyridin-2-ylamine (0.11 g, 0.65 mmol) and heat the reaction at 100° C. for 15 h. Cool the mixture to room temperature, dilute with water and extract with methylene chloride. Wash the combined organic phase with a saturated aqueous solution of sodium bicarbonate, dry over anhydrous sodium sulfate and concentrate under reduced pressure. Purify the residue by

Example 8

Synthesis of 3-[(S)-1-(4-cyano-phenylcarbamoyl)-ethoxy]-N-(5-methyl-4,5,6,7-tetrahydro-thiazolo[5,4-c]pyridin-2-yl)-benzamide (Compound 25)

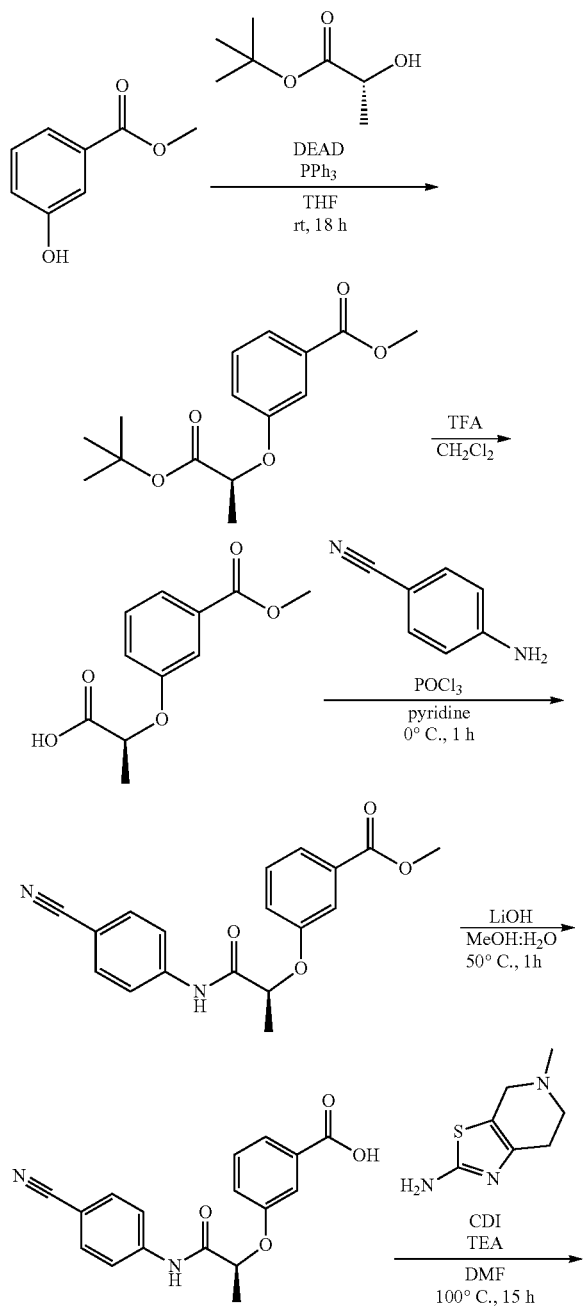

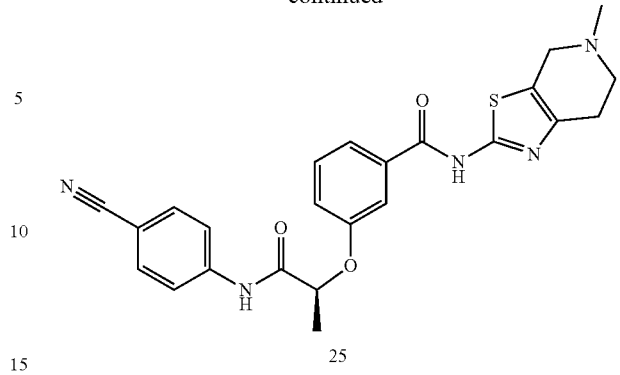

Cool a solution of 3-hydroxy-benzoic acid methyl ester (0.50 g, 3.42 mmol) in tetrahydrofuran (8 mL) to 0° C., and add (R)-2-hydroxy-propionic acid tert-butyl ester (0.52 g, 3.42 mmol) and triphenyl phosphine (0.90 g, 3.42 mmol). Add diethylazodicarboxylate (0.70 mL, 4.4 mmol) to this mixture via a syringe pump over a 1 hour period. Concentrate the reaction mixture under reduced pressure and purify the residue by flash silica gel chromatography to provide 0.80 g of 3-((S)-1-tert-butoxycarbonyl-ethoxy)-benzoic acid methyl ester as an oil.

Cool a solution of 3-((S)-1-tert-butoxycarbonyl-ethoxy)-benzoic acid methyl ester (0.80 g, 2.85 mmol) in methylene chloride (10 mL) to 0° C. and add trifluoroacetic acid (0.98 g 8.60 mmol). Warm the mixture to room temperature and stir overnight. Dilute the mixture with water and extract with methylene chloride. Concentrate the combined organic phase under reduced pressure and purify the residue by trituration with hexanes and methylene chloride to provide 0.40 g of 3-((S)-1-carboxy-ethoxy)-benzoic acid methyl ester as a solid.

Cool a solution of 3-((S)-1-carboxy-ethoxy)-benzoic acid methyl ester (0.32 g, 1.43 mmol) in pyridine (5 mL) to 0° C. and add 4-aminobenzonitrile (0.20 g 1.69 mmol) followed by phosphorous oxychloride (0.15 mL, 1.60 mmol). Stir the mixture at 0° C. for 1 hour then dilute with water and extract with EtOAc. Wash the combined organic portion with a 2N solution of hydrochloric acid then dry over anhydrous sodium sulfate and concentrate under reduced pressure to provide 0.42 g of 3-[(S)-1-(4-cyano-phenylcarbamoyl)-ethoxy]-benzoic acid methyl ester as a foam.

Heat a suspension of 3-[(S)-1-(4-cyano-phenylcarbamoyl)-ethoxy]-benzoic acid methyl ester (0.42 g, 1.30 mmol) in a 1:1 mixture of MeOH:water (10 mL) to 50° C. and add sodium hydroxide (1.0 mL, 2.5 mmol) as a 10% aqueous solution. Stir the mixture at 50° C. for 1 h during which time all of the solids dissolve. Cool the reaction mixture to room temperature and adjust the pH of the mixture to approximately pH 5 by the addition of a 2 N solution of hydrochloric acid. Dilute the mixture with water and extract with methylene chloride. Dry the combined organic phase over anhydrous sodium sulfate and concentrate under reduced pressure to provide 0.38 g of 3-[(S)-1-(4-cyano-phenylcarbamoyl)-ethoxy]-benzoic acid as a foam.

Add 1,1-carbonyldiimdazole (0.05 g 0.31 mmol) followed by N,N-diisopropylethylamine (0.80 mL, 0.45 mmol) to a solution of 3-[(S)-1-(4-cyano-phenylcarbamoyl)-ethoxy]-benzoic acid (0.05 g, 0.16 mmol) in dimethylacetamide (4 mL). Stir the mixture at room temperature for 1 h then add 5-methyl-4,5,6,7-tetrahydro-thiazolo[5,4-c]pyridin-2-ylamine (0.08 g 0.44 mmol) and heat the reaction at 100° C.

for 3 days. Cool the mixture to room temperature, dilute with water and concentrate under reduced pressure. Purify the residue by preparative reverse phase HPLC using acetonitrile:water with 0.1% trifluoroacetic acid additive as the eluent to provide, after concentration under reduced pressure, 0.04 g of the title compound as a solid. MS, electrospray 462.74 (M+H), rt. 1.24 min.

Example 9

Synthesis of 3-[(R)-1-(4-cyano-phenyl)-2-oxo-pyrrolidin-3-yloxy]-N-(5-methyl-4,5,6,7-tetrahydro-thiazolo[5,4-c]pyridin-2-yl)-benzamide trifluoroacetic acid salt (Compound 27)

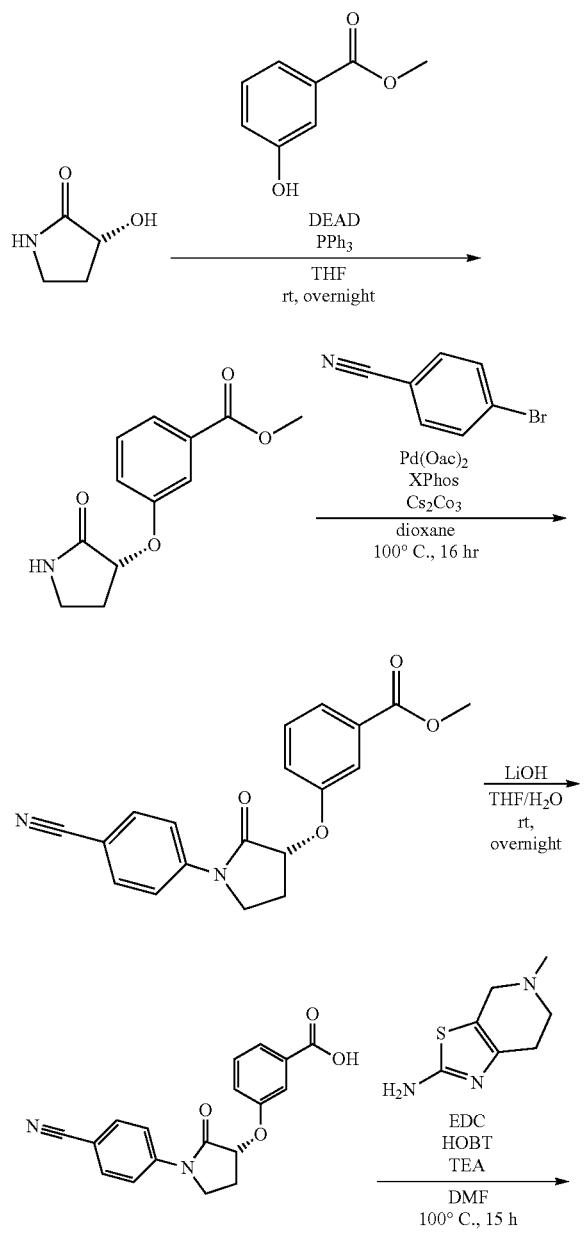

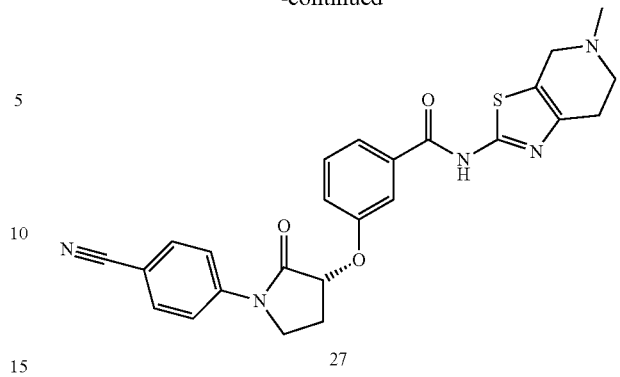

Cool a solution of 3-hydroxy-benzoic acid methyl ester (9.03 g, 59.4 mmol) in tetrahydrofuran (125 mL) to 0° C. and add (R)-3-hydroxy-pyrrolidin-2-one (5.00 g, 49.5 mmol) and triphenyl phosphine (15.6 g, 59.4 mmol). Slowly add to this mixture diethylazodicarboxylate (10.2 mL, 64.3 mmol). Warm the reaction mixture to room temperature and stir overnight. Concentrate the mixture under reduced pressure and purify the residue by flash silica gel chromatography to provide 11.2 g of 3-((R)-2-oxo-pyrrolidin-3-yloxy)-benzoic acid methyl ester as an oil.

Add 4-bromo-benzonitrile (7.0 g, 38 mmol) followed by cesium carbonate (17.5 g, 54.0 mmol) to a solution of 3-(R)-2-oxo-pyrrolidin-3-yloxy)-benzoic acid methyl ester (10.8 g, 46.1 mmol) in 1,4-dioxane (42 mL). Bubble Argon gas through the mixture for 15 minutes then add xanthphos (1.67 g, 2.88 mmol) followed by palladium acetate (0.43 g, 1.92 mmol). Bubble Argon gas through the mixture for an additional 30 minutes. Heat the mixture at 100° C. for 16 h then cool to room temperature, dilute with water, and extract with methylene chloride. Concentrate the combined organic phase under reduced pressure and purify the residue by trituration with diethyl ether, hexanes, and methylene chloride to provide 8.5 g of 3-[(R)-1-(4-cyano-phenyl)-2-oxo-pyrrolidin-3-yloxy]-benzoic acid methyl ester as a solid.

Add water (2 mL) followed by lithium hydroxide (0.62 g, 14.9 mmol) to a solution of 3-[(R)-1-(4-cyano-phenyl)-2-oxo-pyrrolidin-3-yloxy]-benzoic acid methyl ester (1.00 g, 2.98 mmol) of in tetrahydrofuran (4 mL). Stir the mixture overnight at room temperature then concentrate under reduced pressure to remove volatile organics. Wash the concentrated aqueous mixture with EtOAc and then acidify to pH 4 using a 0.5 M solution of citric acid. Extract the mixture with EtOAc and concentrate under reduced pressure to provide 0.74 g of 3-[(R)-1-(4-cyano-phenyl)-2-oxo-pyrrolidin-3-yloxy]-benzoic acid as a solid.

Add N-(-3-dimethylaminopropyl)-N'-ethylcarbodiimide hydrochloride (0.04 g, 0.21 mmol) followed by 7-azahydroxytriazole (0.03 g, 0.22 mmol) of and N,N-diisopropylethylamine (0.08 mL, 0.45 mmol) to a solution of 3-[(R)-1-(4-cyano-phenyl)-2-oxo-pyrrolidin-3-yloxy]-benzoic acid (0.05 g, 0.15 mmol) in dimethylacetamide (1 mL). Stir the mixture at room temperature for 1 h then add 5-methyl-4,5,6,7-tetrahydro-thiazolo[5,4-c]pyridin-2-ylamine (0.03 g, 0.18 mmol) and heat the reaction with stifling to 50° C. overnight. Cool the mixture to room temperature, dilute with water and concentrate under reduced pressure. Purify the residue by preparative reverse phase HPLC using acetonitrile:water with 0.1% trifluoroacetic acid additive as the eluent to provide, after concentration under reduced pressure, 0.02 g of the title compound as a powder. MS, electrospray 474.71 (M+H), rt 1.20 min.

Example 10
Synthesis of trans-4-[3-(5-Methyl-4,5,6,7-tetrahydro-thiazolo[5,4-c]pyridin-2-ylcarbamoyl)-phenyl]-pyrrolidine-3-carboxylic acid (3-cyano-phenyl)-amide bis-trifluoroacetic acid salt (Compound 17)
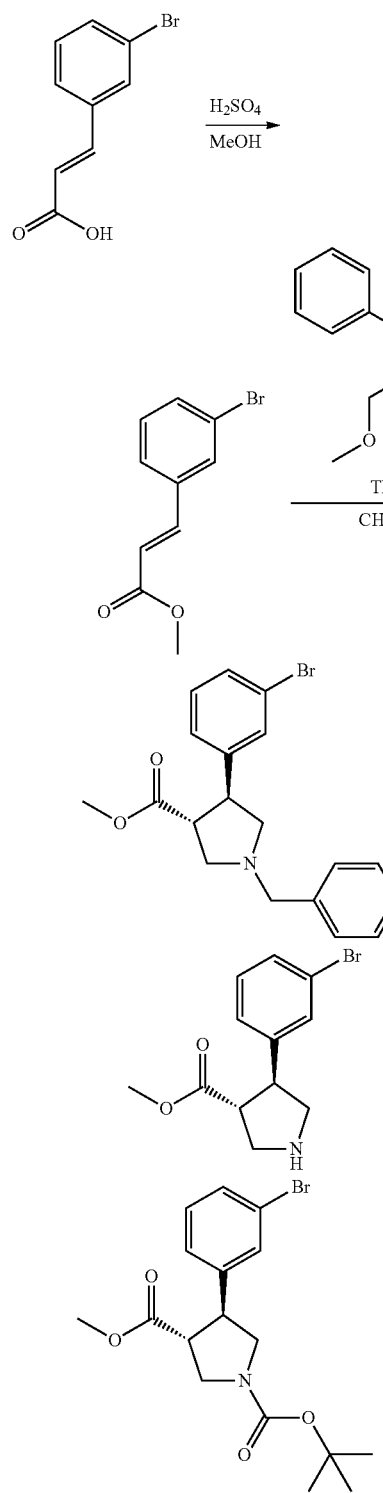
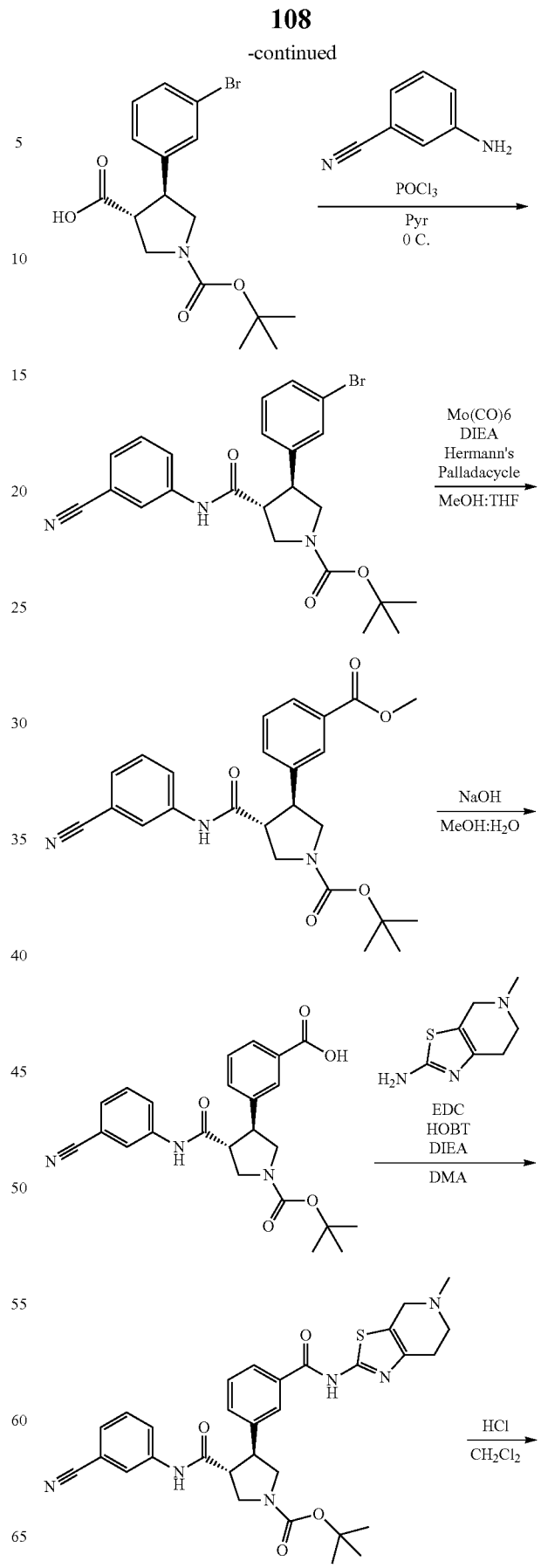

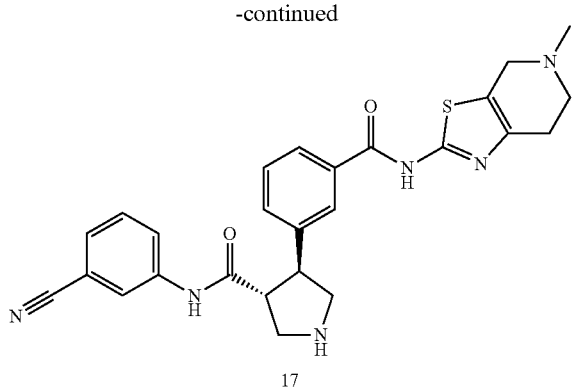

17

Add concentrated sulfuric acid (5.0 mL, 90 mmol) to a solution of 3-bromocinnamic acid (25.0 g, 110 mmol) in MeOH (250 mL). Heat the mixture to reflux for 5 h then cool to room temperature and concentrate under reduced pressure. Dilute the residue with water and extract with EtOAc. Concentrate the combined organic phase under reduced pressure and purify the residue by silica gel chromatography to provide 26 g of trans-3-(3-bromo-phenyl)-acrylic acid methyl ester.

Add benzyl-methoxymethyl-trimethylsilanyl-amine (14.7 g, 2.20 mmol) to a solution of trans-3-(3-bromo-phenyl)-acrylic acid methyl ester (10.0 g, 41.4 mmol) in methylene chloride (80 mL). Cool the mixture to 0° C. and stir for 10 min then add trifluoroacetic acid (0.92 mL, 12.4 mmol) and stir the mixture at 0° C. for an additional 4 h. Dilute the reaction mixture with water and extract with methylene chloride. Dry the combined organic phase over anhydrous sodium sulfate and concentrate under reduced pressure. Purify the residue by silica gel chromatography to provide 12 g (77%) of trans-1-benzyl-4-(3-bromo-phenyl)-pyrrolidine-3-carboxylic acid methyl ester.

Add palladium hydroxide (3.1 g, 22 mmol) to a solution of trans-1-benzyl-4-(3-bromo-phenyl)-pyrrolidine-3-carboxylic acid methyl ester (15 g, 40 mmol) in MeOH (200 mL). Place the mixture under an atmosphere of hydrogen and stir at room temperature for 12 h. Filter the reaction mixture through a pad of diatomaceous earth and concentrate under reduced pressure to provide 11 g (97%) of trans-4-(3-bromo-phenyl)-pyrrolidine-3-carboxylic acid methyl ester.

Add a saturated aqueous solution of sodium bicarbonate (350 mL) to a solution of trans-4-(3-bromo-phenyl)-pyrrolidine-3-carboxylic acid methyl ester (11 g, 38 mmol) in methylene chloride (350 mL). Cool the mixture to 0° C. and add BOC-anhydride (8.9 g, 41 mmol) dropwise. Slowly warm the mixture to room temperature and stir for 12 h. Extract the reaction mixture with methylene chloride, dry the combined organic phase over anhydrous sodium sulfate and concentrate under reduced pressure. Purify the residue by silica gel chromatography to provide 13 g of trans-4-(3-bromo-phenyl)-pyrrolidine-1,3-dicarboxylic acid 1-tert-butyl ester 3-methyl ester.

Add lithium hydroxide (0.50 g, 12 mmol) to a solution of trans-4-(3-bromo-phenyl)-pyrrolidine-1,3-dicarboxylic acid 1-tert-butyl ester 3-methyl ester (0.80 g, 2.08 mmol) in a 1:2:1 mixture of MeOH:tetrahydrofuran:water (8 mL). Stir the mixture at room temperature for 3 h then concentrate under reduced pressure to remove volatile organics. Wash the concentrated aqueous mixture with EtOAc and then acidify to pH 5 using a 0.5 M solution of citric acid. Extract the mixture with EtOAc, dry over anhydrous sodium sulfate, and concentrate under reduced pressure to provide 0.53 g of trans-4-(3-bromo-phenyl)-pyrrolidine-1,3-dicarboxylic acid 1-tert-butyl ester.

Cool a solution of trans-4-(3-bromo-phenyl)-pyrrolidine-1,3-dicarboxylic acid 1-tert-butyl ester (0.50 g, 1.35 mmol) in pyridine (5 mL), to 0° C., and add 3-aminobenzonitrile (0.18 g, 1.48 mmol) followed by phosphorous oxychloride (0.14 mL, 1.50 mmol). Stir the mixture at 0° C. for 1 h then dilute with water. Extract the mixture with EtOAc and wash the combined organic portion with a 2 N solution of hydrochloric acid until the pH of the aqueous washings is strongly acidic. Wash the organic phase with brine then dry over anhydrous sodium sulfate and concentrate under reduced pressure. Purify the residue by flash silica gel chromatography to provide 0.53 g of trans-3-(3-bromo-phenyl)-4-(3-cyano-phenylcarbamoyl)-pyrrolidine-1-carboxylic acid tert-butyl ester as a solid.

Split a solution of trans-3-(3-bromo-phenyl)-4-(3-cyano-phenylcarbamoyl)-pyrrolidine-1-carboxylic acid tert-butyl ester (0.53 g, 1.13 mmol) in a 1:1 mixture of MeOH/THF (10 mL) into three microwave pressure tubes. Add to each tube molybedinum hexacarbonyl (0.06 g, 0.23 mmol) followed by N,N-diisoproylethyl amine (0.15 mL, 0.80 mmol) and Herrmann's palladacycle (0.16 g, 0.17 mmol). Heat each mixture in a microwave reactor at 150° C. for 15 minutes then cool to room temperature. Combine the mixtures, dilute with EtOAc and load onto silica gel. Purify the residue by flash silica gel chromatography to provide 0.20 g of trans-3-(3-cyano-phenylcarbamoyl)-4-(3-methoxycarbonyl-phenyl)-pyrrolidine-1-carboxylic acid tert-butyl ester as a foam.

Add to a solution of trans-3-(3-cyano-phenylcarbamoyl)-4-(3-methoxycarbonyl-phenyl)-pyrrolidine-1-carboxylic acid tert-butyl ester (0.20 g, 0.44 mmol) in MeOH (3 mL), sodium hydroxide as a 10% aqueous solution (0.40 mL, 1.00 mmol). Heat the mixture to 50° C. for 30 min then cool to room temperature and remove the MeOH under reduced pressure. Dilute the mixture with water and adjust the pH to approximately pH 5 by the addition of a 2 N solution of hydrochloric acid causing a solid to precipitate from solution. Collect the formed solid by filtration, wash with water and dry on the filter pad to provide 0.17 g of trans-3-(3-carboxy-phenyl)-4-(3-cyano-phenylcarbamoyl)-pyrrolidine-1-carboxylic acid tert-butyl ester as a powder.

Add N-(-3-dimethylaminopropyl)-N'-ethylcarbodiimide (0.10 g, 0.52 mmol), followed by hydroxybenzotriazole (0.07 g, 0.52 mmol) and N,N-diisopropylethyl amine (0.18 mL, 1.00 mmol) to a solution of trans-3-(3-carboxy-phenyl)-4-(3-cyano-phenylcarbamoyl)-pyrrolidine-1-carboxylic acid tert-butyl ester (0.17 g, 0.39 mmol) in dimethylacetamide (5 mL). Stir the mixture at room temperature for 1 h then add 5-methyl-4,5,6,7-tetrahydro-thiazolo[5,4-c]pyridin-2-ylamine (0.08 g, 0.50 mmol) and heat the mixture to 50° C. with stifling overnight. Cool the reaction to room temperature and dilute with water causing a solid to precipitate from solution. Collect the formed solid by filtration, wash with water and dry on the filter pad to provide 0.23 g (quant.) of trans-3-(3-cyano-phenylcarbamoyl)-4-[3-(5-methyl-4,5,6,7-tetrahydro-thiazolo[5,4-c]pyridin-2-ylcarbamoyl)-phenyl]-pyrrolidine-1-carboxylic acid tert-butyl ester as a powder.

Add HCl as a 4.0 M solution in 1,4-dioxane (0.40 mL, 1.6 mmol) to a solution trans-3-(3-cyano-phenylcarbamoyl)-4-[3-(5-methyl-4,5,6,7-tetrahydro-thiazolo[5,4-c]pyridin-2-ylcarbamoyl)-phenyl]-pyrrolidine-1-carboxylic acid tert-butyl ester (0.23 g, 0.39 mmol) in methylene chloride (10 mL). Stir the mixture at room temperature for 1 h then concentrate under a stream of nitrogen. Purify the residue by preparative reverse phase HPLC using acetonitrile/water with 0.1% trifluoroacetic acid additive as the eluent to provide, after concentration under reduced pressure, 0.07 g (25%) of the title compound as a solid. MS, electrospray 487.77 (M+H), rt. 0.92 min.

The following compound is prepared according to the procedure in Example 10, using the appropriate starting materials:
Compound 15: MS, electrospray 487.71 (M+H), rt. 0.90 min.
Example 11
Synthesis of 3-[1-(3,4-dimethoxy-benzoyl)-pyrrolidin-2-yl]-N-(1,2,3,4-tetrahydro-isoquinolin-7-yl)-benzamide trifluoroacetic acid (Compound 45)
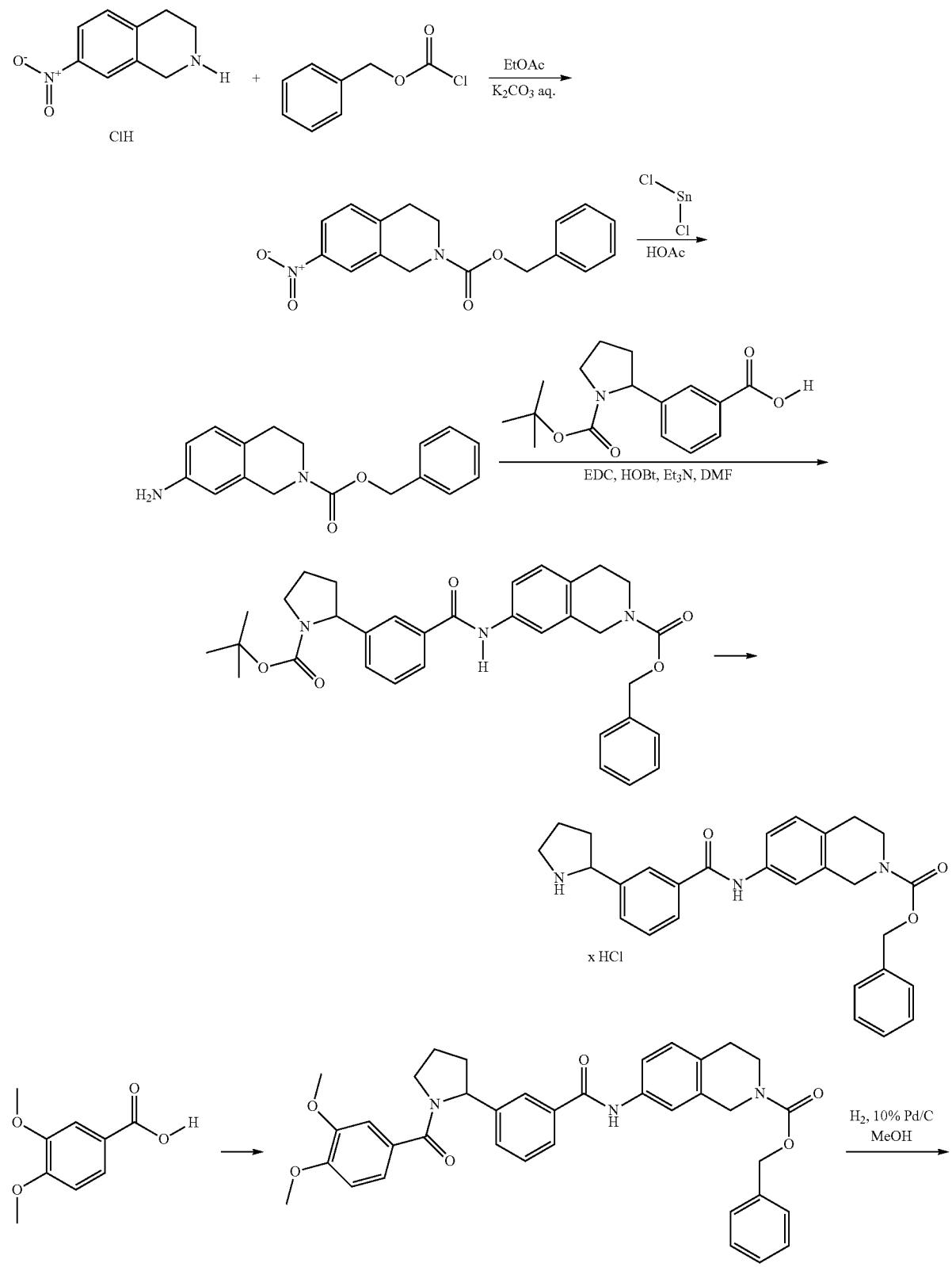

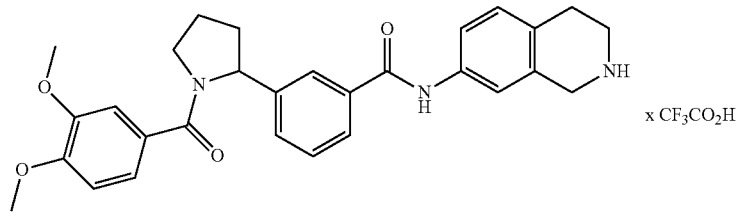

45

To a solution of 7-nitro-1,2,3,4-tetrahydroisoquinoline hydrochloride (11.0 g, 51.25 mmol) in EtOAc (150 mL) at 0° C. in an ice bath add a solution of K$_2$CO$_3$ (15.65 g, 113.25 mmol) in water (150 mL) followed by benzyl chloroformate (8.37 mL, 56.37 mmol) and vigorously stir the reaction at room temperature for 24 h. Separate the layers and extract the aqeuous with more EtOAc (150 mL). Wash the organics with sat. NaHCO$_3$ (200 mL), sat. NH$_4$Cl (200 mL) and water (200 mL), then dry (Na$_2$SO$_4$). Concentrate in vacuo to give 14.70 g of 7-nitro-3,4-dihydro-1H-isoquinoline-2-carboxylic acid benzyl ester as an oil which partially crystallizes.

To a solution of 7-nitro-3,4-dihydro-1H-isoquinoline-2-carboxylic acid benzyl ester (14.70 g, 42.36 mmol) in glacial acetic acid (180 mL), add a solution of tin(II) chloride (25.0 g, 129.21 mmol) and tin(II) chloride dihydrate (19.5 g, 84.72 mmol) as a solution in 10% HCl (71 mL). Stir the resulting solution at room temperature for 24 h. TLC indicates an incomplete reaction. Add more tin(II) chloride dihydrate (49.3 g, 213.95 mmol) followed by 6M HCl (20 mL) and stir the reaction 24 h more at room temperature. TLC now shows complete reaction. Pour the reaction into a vigorously stirring solution of NaOH (135.4 g) in water (250 mL) with ice (500 mL) and EtOAc (600 mL). Stir the suspension vigorously for 10 min (pH=5) then add more NaOH (72 g) as a solution in water (100 mL). The suspension clears up on vigorous stifling for 1 h. Partition the layers (pH aq=9-10) and extract the aqueous with more EtOAc (2×600 mL). Dry the combined organics (K$_2$CO$_3$ and Na$_2$SO$_4$) and concentrate in vacuo. Dissolve the residue in methylene chloride and filter to remove residual inorganics. Remove the solvent in vacuo to give 13.38 g of 7-amino-3,4-dihydro-1H-isoquinoline-2-carboxylic acid benzyl ester as an oil.

To a solution of 2-(3-carboxy-phenyl)-pyrrolidine-1-carboxylic acid tert-butyl ester (500 mg, 1.682 mmol), EDC (346 mg, 1.766 mmol), and HOBt (240 mg, 1.682 mmol) in DMF (5 mL) add Et$_3$N (0.355 mL, 2.523 mmol) and stir the solution at room temperature for 15 min. To this add a solution of the 7-amino-3,4-dihydro-1H-isoquinoline-2-carboxylic acid benzyl ester (500 mg, 1.682 mmol) as a solution in DMF (5 mL) and stir the solution at 65° C. for 24 h. Dilute the reaction with EtOAc (250 mL) and wash with sat. NH$_4$Cl (250 mL), sat. NaHCO$_3$ (250 mL), then water (250 mL). Extract the aqueous layers with more EtOAc (250 mL) and dry the combined organics (Na$_2$SO$_4$), and concentrate in vacuo to give 902 mg of 7-[3-(1-tert-butoxycarbonyl-pyrrolidin-2-yl)-benzoylamino]-3,4-dihydro-1H-isoquinoline-2-carboxylic acid benzyl ester as a solid.

To a solution of 7-[3-(1-tert-butoxycarbonyl-pyrrolidin-2-yl)-benzoylamino]-3,4-dihydro-1H-isoquinoline-2-carboxylic acid benzyl ester (900 mg, 1.62 mmol) in methylene chloride (50 mL) add 4M HCl in dioxane (8.1 mL, (32.4 mmol)) and stir the reaction at room temperature for 24 h. Remove the solvents in vacuo at 40° C., dissolve the residue in EtOAc, and concentrate again concentrate to dryness. Dry the residue in vacuo then triturate in EtOAc and hexane to afford 2.63 g of 7-(3-pyrrolidin-2-yl-benzoylamino)-3,4-dihydro-1H-isoquinoline-2-carboxylic acid benzyl ester HCl as a solid.

Stir a solution of 3,4-dimethoxybenzoic acid (85 mg, 0.461 mmol), EDC (91 mg, 0.461 mmol), HOBt (66 mg, 0.461 mmol), and Et$_3$N (0.195 mL, 1.383 mmol) in DMF (7 mL) at room temperature for 30 min. To this add 7-(3-pyrrolidin-2-ylbenzoylamino)-3,4-dihydro-1H-isoquinoline-2-carboxylic acid benzyl ester HCl salt (236 mg, 0.384 mmol) as a solution in DMF and stir the reaction at room temperature for 48 h. Quench the reaction with sat. NH$_4$Cl (100 mL) and extract with EtOAc (2×150 mL). Wash the organic layers with water (100 mL) then dry (Na$_2$SO$_4$) and concentrate to an oil. Purify by silica gel chromatography eluting with 10% EtOAc/hexane to 100% EtOAc. Concentrate the fractions containing product in vacuo to afford 137 mg of 7-{1-[1-(3,4-dimethoxy-benzoyl)-pyrrolidin-2-yl]-benzoylamino}-3,4-dihydro-1H-isoquinoline-2-carboxylic acid benzyl ester as a solid foam.

To a solution of 7-{3-[1-(3,4-dimethoxy-benzoyl)-pyrrolidin-2-yl]-benzoylamino}-3,4-dihydro-1H-isoquinoline-2-carboxylic acid benzyl ester (131 mg, 0.211 mmol) in MeOH (20 mL) add 10% Pd/C (60 mg) and hydrogenate at 1 atm for 24 h. Remove the Pd/C on a diatomaceous earth pad (1×4 cm) washing with MeOH (5×25 mL). Remove the solvent in vacuo to give a clear residue and purify by reverse-phase prep-HPLC (10% to 90% ACN/water). Concentrate fractions containing product in vacuo to give 106 mg of product 3-[1-(3,4-Dimethoxy-benzoyl)-pyrrolidin-2-yl]-N-(1,2,3,4-tetrahydro-isoquinolin-7-yl)-benzamide trifluoroacetic acid as a glassy solid residue. MS, electrospray 486.7 (M+H), rt 1.12 min.

Example 12

Synthesis of 2-[3-(1,2,3,4-tetrahydro-isoquinolin-7-ylcarbamoyl)-phenyl]-pyrrolidine-1-carboxylic acid (3-cyano-phenyl)-amide trifluoroacetic acid (Compound 47)

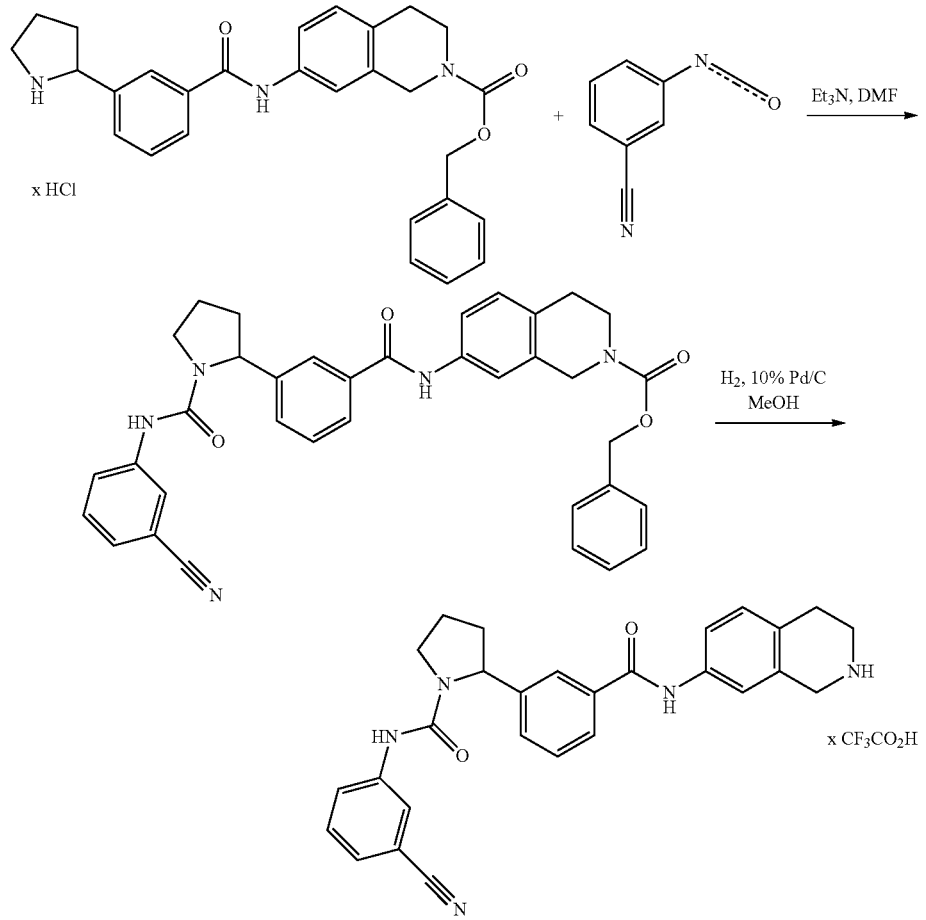

To a solution of 7-(3-pyrrolidin-2-yl-benzoylamino)-3,4-dihydro-1H-isoquinoline-2-carboxylic acid benzyl ester HCl (238 mg, 0.387 mmol) in DMF (5 mL) add Et$_3$N (0.082 mL, 0.581 mmol) followed by 3-cyanophenyl isocyanate (69 mg, 0.464 mmol). Stir the solution at room temperature for 48 h. LCMS analysis indicates the presence of starting material. Add more isocyanate (69 mg, 0.464 mmol) and stir the reaction at room temperature 24 h more. Quench the reaction with sat. NH$_4$Cl (100 mL) and extract with EtOAc (2×150 mL). Wash the organic layers with water (100 mL), dry (Na$_2$SO$_4$) and concentrate to an oil. Purify the crude product by silica gel chromatography eluting with 10% to 75% EtOAc/hexane to afford 186 mg 7-{3-[1-(3-cyanophenylcarbamoyl)-pyrrolidin-2-yl]-benzoylamino}-3,4-dihydro-1H-isoquinoline-2-carboxylic acid benzyl ester as a solid foam.

To a solution of 7-{3-[1-(3-cyano-phenylcarbamoyl)-pyrrolidin-2-yl]-benzoylamino}-3,4-dihydro-1H-isoquinoline-2-carboxylic acid benzyl ester (163 mg, 0.272 mmol) in MeOH (20 mL) add 10% Pd/C (60 mg) and hydrogenate at 1 atm for 24 h. LCMS analysis indicates the presence of starting material (34%). Add more 10% Pd/C (70 mg) in 5 mL MeOH and hydrogenate 24 h more. The Pd/C was removed on a diatomaceous earth pad (1×4 cm) washing with MeOH (5×25 mL). Remove the solvent in vacuo to give a clear residue. Purify by reverse-phase prep-HPLC (10% to 90% ACN/water), concentrate fractions containing product to afford 91 mg product 2-[4-(1,2,3,4-tetrahydro-isoquinolin-7-ylcarbamoyl)-phenyl]-pyrrolidine-1-carboxylic acid (3-cyano-phenyl)-amide trifluoroacetic acid as a solid.

The following compounds are prepared according to the procedure in Example 11 or 12 using the appropriate starting materials:

Compound 49: MS, electrospray 466.6 (M+H), rt 1.17 min.
Compound 55: MS, electrospray 487.6 (M+H), rt 1.21 min.
Compound 57: MS, electrospray 563.5 (M+H), rt 1.40 min.
Compound 59: MS, electrospray 480.6 (M+H), rt 1.26 min.
Compound 61: MS, electrospray 487.4 (M+H), rt 1.17 min.
Compound 63: MS, electrospray 487.4 (M+H), rt 1.13 min.
Compound 65: MS, electrospray 563.5 (M+H), rt 1.35 min.
Compound 67: MS, electrospray 563.5 (M+H), rt 1.31 min.
Compound 111: MS, electrospray 501.0 (M+H), rt 1.38 min.
Compound 113: MS, electrospray 487.0 (M+H), rt 1.29 min.
Compound 115: MS, electrospray 501.1 (M+H), rt 1.36 min.
Compound 117: MS, electrospray 501.0 (M+H), rt 1.37 min.
Compound 119: MS, electrospray 487.1 (M+H), rt 1.29 min.
Compound 121: MS, electrospray 501.1 (M+H), rt 1.37 min.
Compound 147: MS, electrospray 454.7 (M+H), rt 1.21 min.

Compound 149: MS, electrospray 454.8 (M+H), rt 1.21 min.
Compound 155: MS, electrospray 487.4 (M+H), rt 1.26 min.
Compound 157: MS, electrospray 487.5 (M+H), rt 1.21 min.
Compound 4: MS, electrospray 503.6 (M+H), rt 1.34 min.
Compound 6: MS, electrospray 503.6 (M+H), rt 1.33 min.

Example 13

Synthesis of (S)-2-[3-(5-methyl-4,5,6,7-tetrahydro-thiazolo[5,4-c]pyridin-2-ylcarbamoyl)-phenyl]-pyrrolidine-1-carboxylic acid (3-cyano-phenyl)-amide trifluoroacetic acid (Compound 99) and (R)-2-[3-(5-Methyl-4,5,6,7-tetrahydro-thiazolo[5,4-c]pyridin-2-ylcarbamoyl)-phenyl]-pyrrolidine-1-carboxylic acid (3-cyano-phenyl)-amide trifluoroacetic acid (Compound 101)

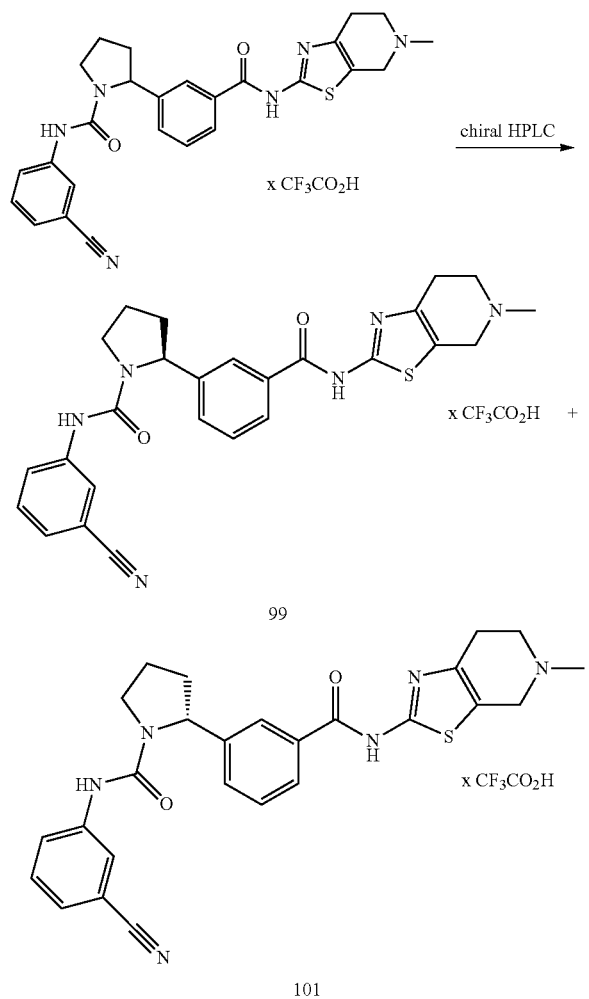

Resolve racemic 2-[3-(5-methyl-4,5,6,7-tetrahydro-thiazolo[5,4-c]pyridin-2-ylcarbamoyl)-phenyl]-pyrrolidine-1-carboxylic acid (3-cyano-phenyl)-amide trifluoroacetic acid (128 mg, 0.207 mmol) by Chiral AD-H column eluting with EtOH/hexane gradient. Concentrate fractions containing each enantiomer and re-purify each residue by reverse-phase prep-HPLC (10% to 90% ACN/water). Concentrate fractions containing product and triturate each residue in EtOAc and hexane to afford the products as solids: chiral HPLC first eluting peak 99% ee (37 mg) Compound 99: MS, electrospray 487.3 (M+H), rt 1.24 min; and chiral HPLC $2^{nd}$ eluting peak 91% ee (27 mg)
Compound 101:MS, electrospray 487.3 (M+H), rt 1.24 min.

The following compounds are prepared according to the procedures in Example 11-13 using the appropriate starting materials:
Compound 51: MS, electrospray 466.4 (M+H), rt 1.22 min.
Compound 53: MS, electrospray 466.4 (M+H), rt 1.22 min.
Compound 103: MS, electrospray 563.5 (M+H), rt 1.47 min.
Compound 105: MS, electrospray 563.5 (M+H), rt 1.46 min.
Compound 107: MS, electrospray 480.2 (M+H), rt 1.30 min.
Compound 109: MS, electrospray 480.2 (M+H), rt 1.29 min.

Example 14

Synthesis of 3-[1-(3,4-dimethoxy-benzoyl)-pyrrolidin-2-yl]-N-(5-methyl-4,5,6,7-tetrahydro-thiazolo[5,4-c]pyridin-2-yl)-benzamide (Compound 69)

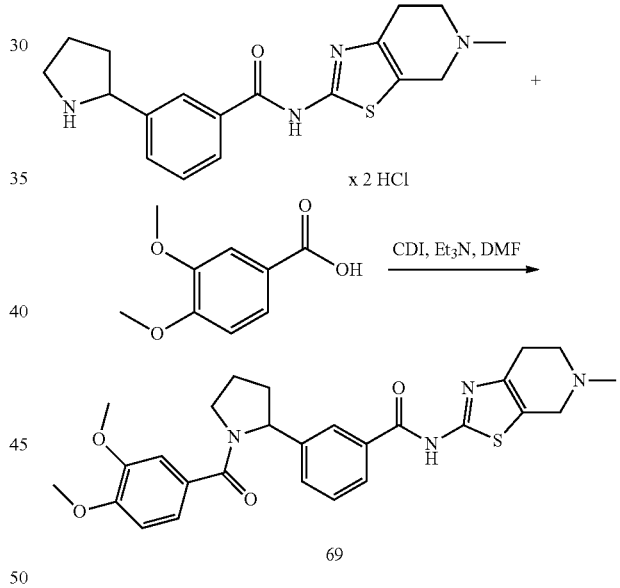

Stir a solution of 3,4-dimethoxybenzoic acid (49 mg, 0.265 mmol) and CDI (44 mg, 0.265 mmol) in DMF (2.5 mL) for 10 min at room temperature. Add the N-(5-Methyl-4,5,6,7-tetrahydro-thiazolo[5,4-c]pyridin-2-yl)-3-pyrrolidin-2-yl-benzamide di-HCl (100 mg, 0.241 mmol) followed by Et₃N (0.118 mL, 0.844 mmol), and stir the solution at room temperature for 24 h. Purify the crude reaction by reverse-phase prep-HPLC (10% to 90% CH₃CN/water). Concentrate the fractions containing product to give the title compound as a solid (100 mg). MS, electrospray 507.5 (M+H), rt 1.13 min.

The following compounds are prepared according to the procedures in Example 11 and 14 using the appropriate starting materials:
Compound 71: MS, electrospray 507.5 (M+H), rt 1.13 min.
Compound 73: MS, electrospray 511.4 (M+H), rt 1.23 min.
Compound 123: MS, electrospray 525.4 (M+H), rt 1.29 min.

Compound 125: MS, electrospray 505.6 (M+H), rt 1.31 min.
Compound 127: MS, electrospray 521.5 (M+H), rt 1.19 min.
Compound 129: MS, electrospray 511.0 (M+H), rt 1.34 min.
Compound 131: MS, electrospray 472.0 (M+H), rt 1.20 min.
Compound 133: MS, electrospray 472.1 (M+H), rt 1.22 min.
Compound 135: MS, electrospray 525.0 (M+H), rt 1.38 min.
Compound 137: MS, electrospray 486.1 (M+H), rt 1.28 min.
Compound 139: MS, electrospray 486.0 (M+H), rt 1.28 min.
Compound 141: MS, electrospray 474.6 (M+H), rt 1.12 min.
Compound 143: MS, electrospray 478.5 (M+H), rt 1.23 min.
Compound 145: MS, electrospray 458.6 (M+H), rt 1.22 min.
Compound 2: MS, electrospray 511.5 (M+H), rt 1.27 min.
Compound 8: MS, electrospray 527.5 (M+H), rt 1.41 min.
Compound 98: MS, electrospray 523.8 (M+H), rt 1.36 min.

Example 15

Synthesis of 2-[3-(5-Methyl-4,5,6,7-tetrahydro-thiazolo[5,4-c]pyridin-2-ylcarbamoyl)-phenyl]-pyrrolidine-1-carboxylic acid (3-carbamoyl-phenyl)-amide trifluoroacetic acid (Compound 75)

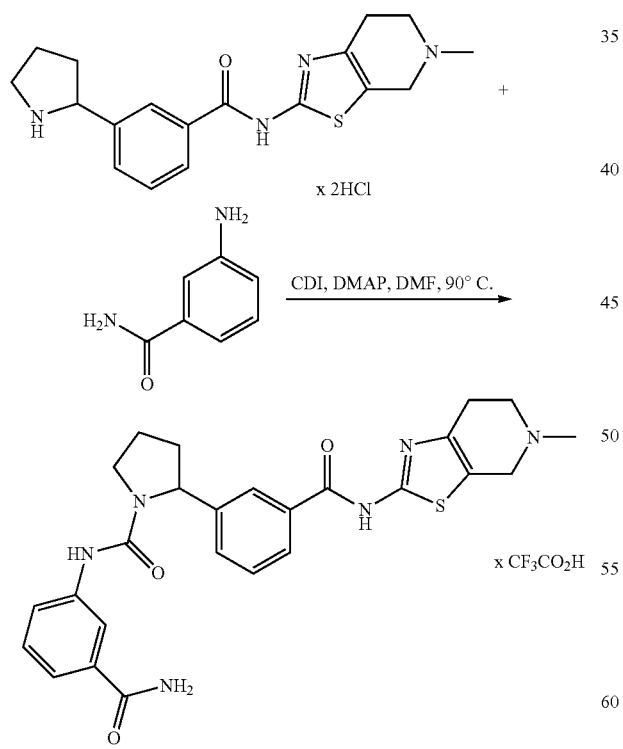

Stir a solution of 3-aminobenzamide (51 mg, 0.362 mmol), CDI (60 mg, 0.362 mmol), and DMAP (45 mg, 0.362 mmol) in DMF (1.5 mL) at 90° C. for 30 min. A precipitate forms from the initial homogenous solution. Add N-(5-methyl-4,5,6,7-tetrahydro-thiazolo[5,4-c]pyridin-2-yl)-3-pyrrolidin-2-yl-benzamide di-HCl (100 mg, 0.241 mmol) to the hot reaction followed by more DMF (1 mL) and continue heating at 90° C. for 20 min. Cool the reaction to room temperature, dilute with water (1 mL), acidify with TFA (0.2 mL), and purify directly by reverse phase prep HPLC. Concentrate the fractions containing product to a solid which contains symmetric benzamide urea (30%). Suspend the solid in MeOH (4 mL) and sonicate—filter off the solid side product washing with MeOH (1 mL). Concentrate the filtrate, dry the residue in vacuo and triturate in EtOAc and hexane to give the title compound as a solid (97 mg). MS, electrospray 505.4 (M+H), rt 1.05 min.

The following compounds are prepared according to the procedures in Example 11 and 15 using the appropriate starting materials:

Compound 77: MS, electrospray 505.4 (M+H), rt 1.04 min.
Compound 151: MS, electrospray 472.6 (M+H), rt 1.03 min.
Compound 153: MS, electrospray 472.6 (M+H), rt 1.02 min.

Example 16

Synthesis of 3-((S)-1-tert-Butoxycarbonylamino-ethyl)-benzoic acid

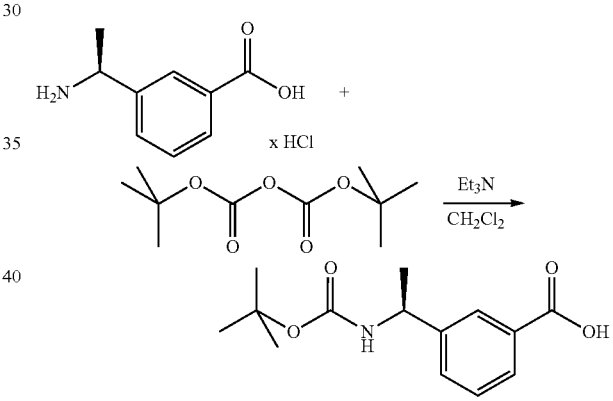

To a suspension of (S)-3-(1-aminoethyl)benzoic acid HCl (734 mg, 3.64 mmol) in methylene chloride (5 mL) at room temperature add Et₃N (1.02 mL, 7.28 mmol) followed by di-tert-butyl-dicarbonate (883 mg, 4.004 mmol) as a solution in methylene chloride (5 mL). Stir the reaction at room temperature for 24 h adding DMF (5 mL) to help solubilization. Partition the reaction between EtOAc (200 mL) and water (200 mL) acidified with 1 mL glacial HOAc. Extract the aqueous layer with more EtOAc (200 mL) and wash the combined organics with water (200 mL) and brine (50 mL). Dry the organics (Na₂SO₄) and concentrate. Triturate the residue in Et₂O and hexane, and filter the solid to afford the title compound as a white solid (550 mg) white solid.

The intermediate synthesized in Example 16 is used to prepare the compounds listed below using appropriate intermediates and procedures analogous to those described in Examples 11 and 12

Compound 79: MS, electrospray 461.3 (M+H), rt 1.16 min.
Compound 81: MS, electrospray 461.3 (M+H), rt 1.15 min.
Compound 83: MS, electrospray 461.4 (M+H), rt 1.22 min.
Compound 85: MS, electrospray 461.5 (M+H), rt 1.22 min.

The intermediate synthesized in Example 16 is used to prepare the compounds listed below using appropriate intermediates and procedures analogous to those described in Examples 11 and 14

Compound 87: MS, electrospray 485.0 (M+H), rt 1.27 min.
Compound 89: MS, electrospray 485.1 (M+H), rt 1.28 min.
Compound 91: MS, electrospray 465.5 (M+H), rt 1.24 min.
Compound 93: MS, electrospray 465.6 (M+H), rt 1.22 min.
Compound 95: MS, electrospray 481.3 (M+H), rt 1.15 min.
Compound 97: MS, electrospray 481.2 (M+H), rt 1.16 min.

Example 17

Synthesis of 3-((R)-1-tert-butoxycarbonylamino-propyl)-benzoic acid

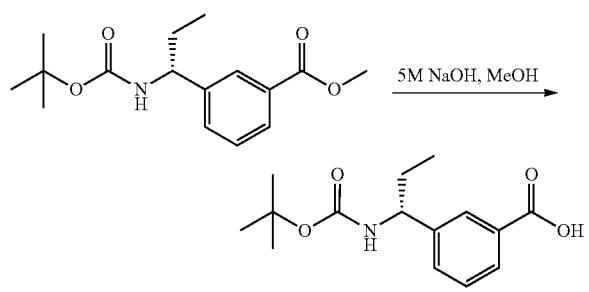

To a stifling solution of N-Boc methyl 3-((1R)-aminopropyl)benzoate (500 mg, 1.704 mmol) in MeOH (5 mL) at room temperature add 5M NaOH aqueous solution (3.41 mL, 17.04 mmol) and stir the reaction at ambient temp for 4 h. Cool the reaction to 0° C. in ice and quench by addition of glacial HOAc (1 mL, 17.5 mmol) to pH 5 then dilute with saturated sodium hydrogen tartrate (50 mL) to pH 2. Extract this with EtOAc (3×75 mL), dry the organics (Na$_2$SO$_4$) and concentrate to a clear oil which solidifies in vacuo to afford the title compound as a solid (486 mg). MS, electrospray 559.7 (M+H, dimer), rt 1.50 min.

The intermediate synthesized in Example 17 is used to prepare the compounds listed below using appropriate intermediates and procedures analogous to those described in Examples 11 and 14

Compound 10: MS, electrospray 475.5 (M+H), rt 1.35 min.
Compound 12: MS, electrospray 475.4 (M+H), rt 1.33 min.
Compound 14: MS, electrospray 499.4 (M+H), rt 1.43 min.

Example 18

Synthesis of (R)-2-{3-[4-(2-morpholin-4-yl-ethyl)-phenylcarbamoyl]-phenyl}-pyrrolidine-1-carboxylic acid (3-cyano-phenyl)-amide trifluoro acetic acid (Compound 16)

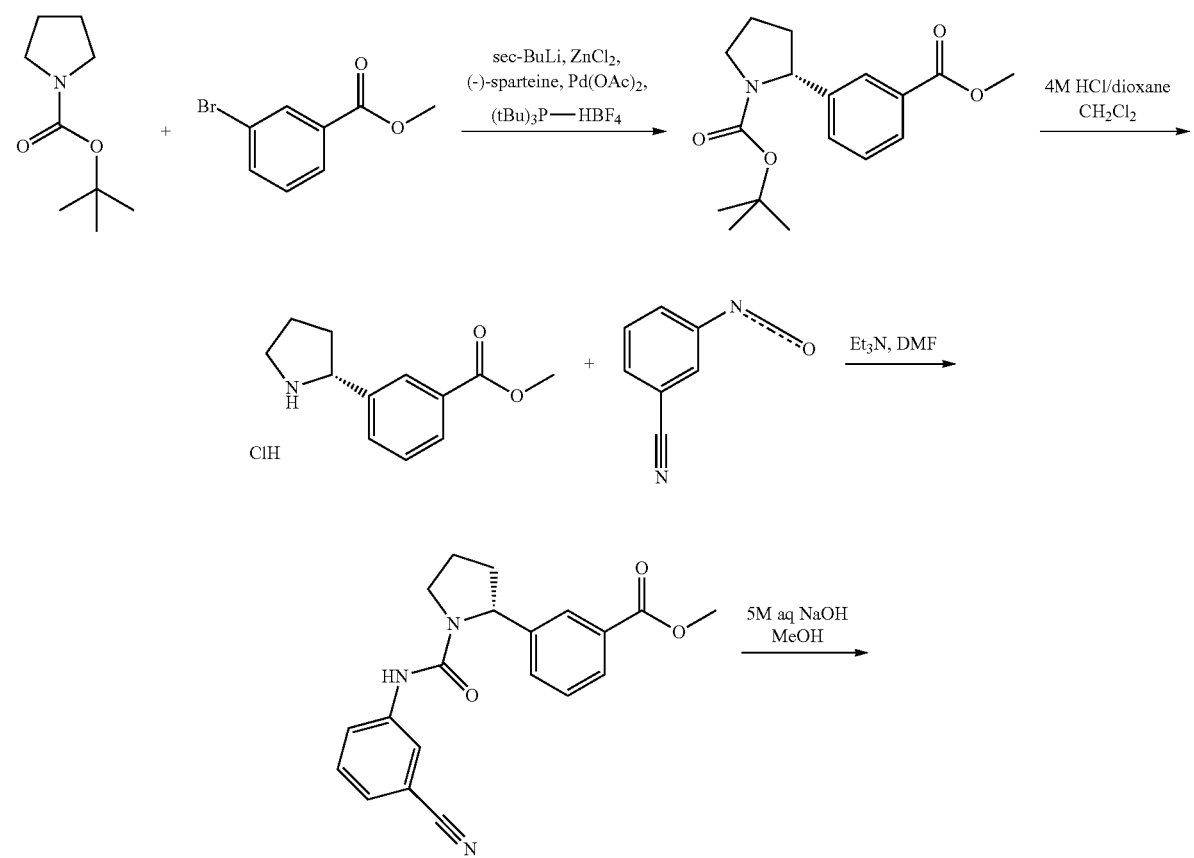

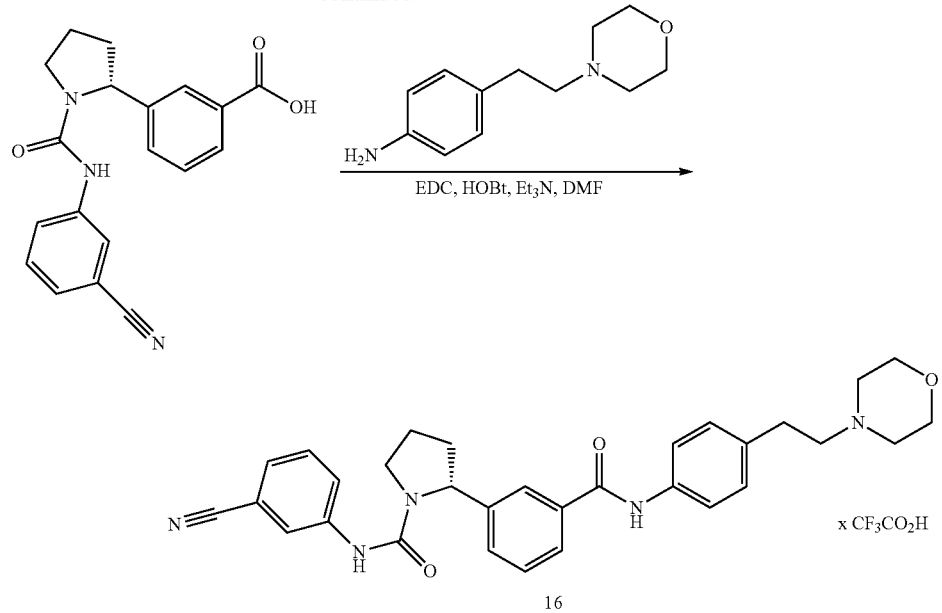

In a 1 L 3-neck flask fitted with thermocouple, addition funnel, and mechanical stirrer, stir a solution of tert-butyl 1-pyrrolidinecarboxylate (42.0 mL, 232.5 mmol) and (−)-sparteine (54.0 mL, 232.7 mmol) in anhydrous MTBE (350 mL) for 10 min at room temperature then cool to −78° C. To this add sec-BuLi (170 mL of a 1.4 M solution in cyclohexane, 238.0 mmol) dropwise via addition funnel directly into the solution over 90 min keeping the temperature <−73° C. Stir the resulting solution at −78° C. for 3 h. Add a solution of $ZnCl_2$ (235.0 mL of a 1M solution in $Et_2O$, 235.0 mmol) to the solution dropwise with rapid stirring keeping the temperature <−70° C. over 1 h. Stir the resulting light suspension at −75° C. for 20 min, warm to 0° C. over 1 h, then to 20° C. over 15 min. Stir the reaction at room temperature for 40 min. Charge the reaction, in the room temperature water bath, with methyl 3-bromobenzoate (43.4 g, 197.8 mmol), palladium(II) acetate (2.61 g, 11.62 mmol) and tri-tert-butyl-phosphonium tetrafluoroborate (4.172 g, 13.95 mmol) all homogenized and in one portion. A thick suspension develops within 5 min accompanied by a mild exotherm. Stir the suspension 24 h at room temperature. Add MTBE (400 mL) to the reaction to facilitate filtration. Add ammonium hydroxide (16 mL) to the reaction and stir at room temperature 2 h. Filter the slurry over a pad of diatomaceous earth (4×10 cm) washing with $Et_2O$ (5×300 mL). Concentrate the organic at room temperature to a volume of 1 L then chill to 5° C. Wash the cold filtrate with cold 1M HCl (1 L) then water (2×μL) and brine (300 mL). Extract the aqueous layers with EtOAc (400 mL) and dry the combined organics ($Na_2SO_4$) and concentrate at 35° C. The crude product was purified by silica gel chromatography eluting with 100% hexane to 20% EtOAc/hexane. Pool and concentrate fractions containing product in vacuo at 40° C. to give (R)-2-(3-methoxycarbonyl-phenyl)-pyrrolidine-1-carboxylic acid tert-butyl ester as an oil (49.62 g).

To a stifling solution of (R)-2-(3-methoxycarbonyl-phenyl)-pyrrolidine-1-carboxylic acid tert-butyl ester (830 mg, 2.582 mmol) in methylene chloride (30 mL) at room temperature add 4 M HCl in dioxane solution (12.91 mL, 51.64 mmol) and stir the reaction at ambient temp for 18 h. Concentrate the solution in vacuo at 35° C. to remove most solvent. Dilute and stir the dioxane suspension of solids with $Et_2O$ (50 mL) and hexane (50 mL). Filter the solid washing with $Et_2O$ then hexane and dry in vacuo under $P_2O_5$ to give (R)-3-pyrrolidin-2-yl-benzoic acid methyl ester HCl as a solid (577 mg).

To a solution of (R)-3-pyrrolidin-2-yl-benzoic acid methyl ester HCl (550 mg, 2.230 mmol) in DMF (10 mL) add dry $Et_3N$ (1.1 mL, 7.81 mmol) followed by 3-cyanophenyl isocyanate (663 mg, 4.46 mmol). Stir the solution at room temperature for 72 h. Quench the reaction with sat. $NH_4Cl$ (150 mL) and extract with EtOAc (2×150 mL). Wash the organic layers with water (150 mL), dry ($Na_2SO_4$), and concentrate at 40° C. Purify the residue by silica gel chromatography eluting with 10% to 50% EtOAc/hexane.

Concentrate fractions containing product to afford 1.086 g solid 3-[(R)-1-(3-cyano-phenylcarbamoyl)-pyrrolidin-2-yl]-benzoic acid methyl ester.

To a stifling solution of 3-[(R)-1-(3-cyano-phenylcarbamoyl)-pyrrolidin-2-yl]-benzoic acid methyl ester (1.086 g, 2.487 mmol) in MeOH (30 mL) at room temperature add 5 M NaOH aqueous solution (10 mL, 49.74 mmol) and stir the reaction at ambient temp for 18 h. Cool the reaction to 0° C. in ice and quench with slow addition of conc. HCl (5 mL) over 15 min, maintaining internal temp at 5° C., to a final pH of 1. Extract the cold suspension with EtOAc (2×100 mL), and wash the organics with water (2×100 mL). Dry the organic layer ($Na_2SO_4$), concentrate to a residue in vacuo. Purify this by silica gel chromatography eluting with a gradient of 50% EtOAc/hexane to 100% EtOAc. Pool and concentrate fractions containing product, and triturate the residue in $Et_2O$ and hexane to afford 3-[(R)-1-(3-cyano-phenylcarbamoyl)-pyrrolidin-2-yl]-benzoic acid as a solid (347 mg).

To a solution of 3-[(R)-1-(3-cyano-phenylcarbamoyl)-pyrrolidin-2-yl]-benzoic acid (68 mg, 0.197 mmol), EDC (41 mg, 0.207 mmol), and HOBt (28 mg, 0.197 mmol) in DMF (2.5 mL) add $Et_3N$ (0.042 mL, 0.296 mmol) and stir the solution at room temperature for 30 min. To this add 4-(2-morpholin-4-yl-ethyl)aniline (42 mg, 0.197 mmol) and stir the solution at room temperature for 24 h. Dilute the reaction with water (1 mL), quench with TFA (0.3 mL), and purify directly by reverse phase prep HPLC (10% to 90% $CH_3CN$/water). Concentrate fractions containing product and transfer the residue in EtOAc (3 mL). Precipitation with added hexane affords the title compound as a solid (105 mg). MS, electrospray 524.8 (M+H), rt 1.36 min.

The following compound is prepared according to the procedure in Example 18 using the appropriate starting materials:

Compound 18: MS, electrospray 508.8 (M+H), rt 1.39 min.

Example 19

Synthesis of (R)-2-[3-((S)-6-Amino-4,5,6,7-tetrahydro-benzothiazol-2-ylcarbamoyl)-phenyl]-pyrrolidine-1-carboxylic acid (3-cyano-phenyl)-amide trifluoroacetic acid (Compound 20)

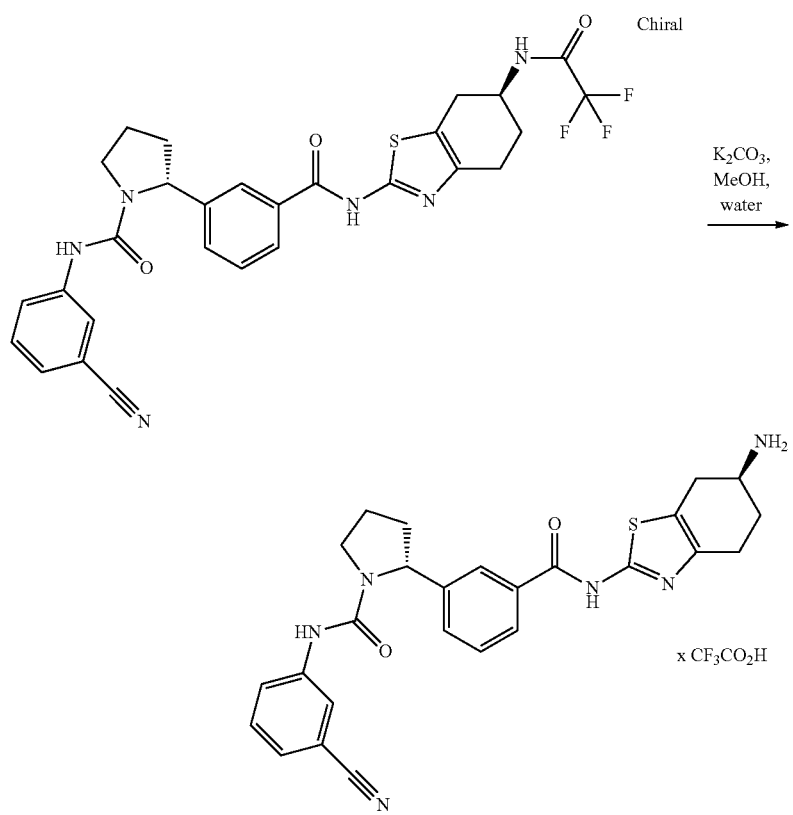

To a stifling solution of crude (R)-2-{3-[(S)-6-(2,2,2-trifluoro-acetylamino)-4,5,6,7-tetrahydro-benzothiazol-2-ylcarbamoyl]-phenyl}-pyrrolidine-1-carboxylic acid (3-cyano-phenyl)-amide (87 mg, 0.149 mmol) in MeOH (5 mL) and water (1 mL) at room temperature add anhydrous $K_2CO_3$ (200 mg, 1.447 mmol) and stir the reaction at 65° C. for 18 h. Remove the solvent in vacuo and dry the solid residue in vacuo. Suspend in DMF and filter off the $K_2CO_3$. Dilute with water and quench with TFA (0.5 mL). Purify the solution by reverse phase prep HPLC (10% to 90% $CH_3CN$/water). Pool and concentrate fractions containing product and dry in vacuo to afford the title compound as a solid (35 mg). MS, electrospray 487.5 (M+H), rt 1.26 min.

The following compound is prepared according to the procedure in Examples 18 and 19 using the appropriate starting materials:

Compound 22: MS, electrospray 487.5 (M+H), rt 1.26 min.

Example 20

Synthesis of (R)-2-(3-Carboxy-phenyl)-pyrrolidine-1-carboxylic acid tert-butyl ester

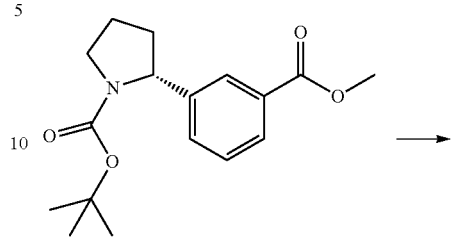

-continued

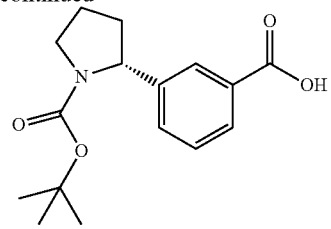

To a stifling solution of (R)-2-(3-methoxycarbonyl-phenyl)-pyrrolidine-1-carboxylic acid tert-butyl ester (98.6 g, 319.7 mmol) in MeOH (1000 mL) in a water bath at 15° C. add 10M NaOH aqueous solution (500 mL) portionwise over 5 min (exotherm to 37° C.) and stir the reaction at ambient temp for 20 h. Concentrate the reaction in vacuo at 35° C. to remove MeOH and give a suspension. Dilute the slurry with water (200 mL), cool to −15° C. in a dry ice/iPrOH bath and quench with addition of concentrated HCl (417 mL) over 1 h with vigorous mechanical stirring maintaining internal temp at −5° C., to a final pH of 1. Extract the cold suspension with EtOAc (2×1500 mL), and wash the organics with water (2×1000 mL) and brine (400 mL). Dry the organic layers (Na$_2$SO$_4$), and concentrate at 40° C. to a solid. Suspend this in hexane (750 mL) and filter to give 91.65 g of the product (R)-2-(3-Carboxy-phenyl)-pyrrolidine-1-carboxylic acid tert-butyl ester as a solid.

The intermediate synthesized in Example 20 is used to prepare the compounds listed below using appropriate intermediates and procedures analogous to those described in Examples 11, 14 and 18

Compound 24: MS, electrospray 545.4 (M+H), rt 1.04 min.
Compound 26: MS, electrospray 524.4 (M+H), rt 0.97 min.
Compound 28: MS, electrospray 587.8 (M+H), rt 1.38 min.
Compound 30: MS, electrospray 535.8 (M+H), rt 1.27 min.
Compound 32: MS, electrospray 508.0 (M+H), rt 1.13 min.
Compound 34: MS, electrospray 492.0 (M+H), rt 1.25 min.
Compound 36: MS, electrospray 512.0 (M+H), rt 1.24 min.
Compound 40: MS, electrospray 514.0 (M+H), rt 1.20 min.
Compound 48: MS, electrospray 573.5 (M+H), rt 1.05 min.
Compound 50: MS, electrospray 625.5 (M+H), rt 1.29 min.
Compound 52: MS, electrospray 530.1 (M+H), rt 1.10 min.
Compound 54: MS, electrospray 532.0 (M+H), rt 1.12 min.
Compound 56: MS, electrospray 525.1 (M+H), rt 1.03 min.
Compound 58: MS, electrospray 532.0 (M+H), rt 1.04 min.
Compound 60: MS, electrospray 515.1 (M+H), rt 0.93 min.
Compound 62: MS, electrospray 525.1 (M+H), rt 0.98 min.
Compound 66: MS, electrospray 514.1 (M+H), rt 0.91 min.
Compound 68: MS, electrospray 514.0 (M+H), rt 1.13 min.
Compound 70: MS, electrospray 515.1 (M+H), rt 1.13 min.
Compound 74: MS, electrospray 531.1 (M+H), rt 0.97 min.
Compound 76: MS, electrospray 532.0 (M+H), rt 1.17 min.
Compound 77: MS, electrospray 514.1 (M+H), rt 1.11 min.
Compound 80: MS, electrospray 525.1 (M+H), rt 1.01 min.
Compound 82: MS, electrospray 582.9 (M+H), rt 1.20 min.
Compound 84: MS, electrospray 514.8 (M+H), rt 1.02 min.
Compound 86: MS, electrospray 513.8 (M+H), rt 1.15 min.
Compound 88: MS, electrospray 552.5 (M+H), rt 1.03 min.
Compound 90: MS, electrospray 542.5 (M+H), rt 1.19 min.
Compound 92: MS, electrospray 559.4 (M+H), rt 1.17 min.
Compound 94: MS, electrospray 559.8 (M+H), rt 1.10 min.
Compound 96: MS, electrospray 542.9 (M+H), rt 0.98 min.
Compound 100: MS, electrospray 541.5 (M+H), rt 1.19 min.
Compound 102: MS, electrospray 541.5 (M+H), rt 0.94 min.
Compound 104: MS, electrospray 558.8 (M+H), rt 1.02 min.
Compound 106: MS, electrospray 541.8 (M+H), rt 1.16 min.
Compound 108: MS, electrospray 542.8 (M+H), rt 1.07 min.
Compound 112: MS, electrospray 577.8 (M+H), rt 1.21 min.
Compound 114: MS, electrospray 581.8 (M+H), rt 1.34 min.
Compound 116: MS, electrospray 561.8 (M+H), rt 1.36 min.
Compound 119: MS, electrospray 584.4 (M+H), rt 1.17 min.
Compound 120: MS, electrospray 601.4 (M+H), rt 1.10 min.
Compound 122: MS, electrospray 583.5 (M+H), rt 0.96 min.
Compound 124: MS, electrospray 600.7 (M+H), rt 1.02 min.
Compound 126: MS, electrospray 584.7 (M+H), rt 1.08 min.
Compound 128: MS, electrospray 615.4 (M+H), rt 1.09 min.
Compound 130: MS, electrospray 583.5 (M+H), rt 1.22 min.
Compound 132: MS, electrospray 594.5 (M+H), rt 1.02 min.
Compound 134: MS, electrospray 667.5 (M+H), rt 1.31 min.
Compound 136: MS, electrospray 601.4 (M+H), rt 1.15 min.
Compound 138: MS, electrospray 584.5 (M+H), rt 0.98 min.
Compound 140: MS, electrospray 583.5 (M+H), rt 1.16 min.

The intermediate synthesized in Example 20 is used to prepare the compound listed below using appropriate intermediates and procedures analogous to those described in Examples 11, 12, and 18

Compound 38: MS, electrospray 487.8 (M+H), rt 1.27 min.

The intermediate synthesized in Example 20 is used to prepare the compounds listed below using appropriate intermediates and procedures analogous to those described in Examples 11, 15 and 18:

Compound 44: MS, electrospray 505.1 (M+H), rt 1.04 min.
Compound 46: MS, electrospray 506.0 (M+H), rt 1.05 min.

Example 21

Synthesis of 3-[(R)-1-(4-Cyano-2,3-dihydro-indole-1-carbonyl)-pyrrolidin-2-yl]-N-(5-methyl-4,5,6,7-tetrahydro-thiazolo[5,4-c]pyridin-2-yl)-benzamide trifluoroacetic acid (Compound 42)

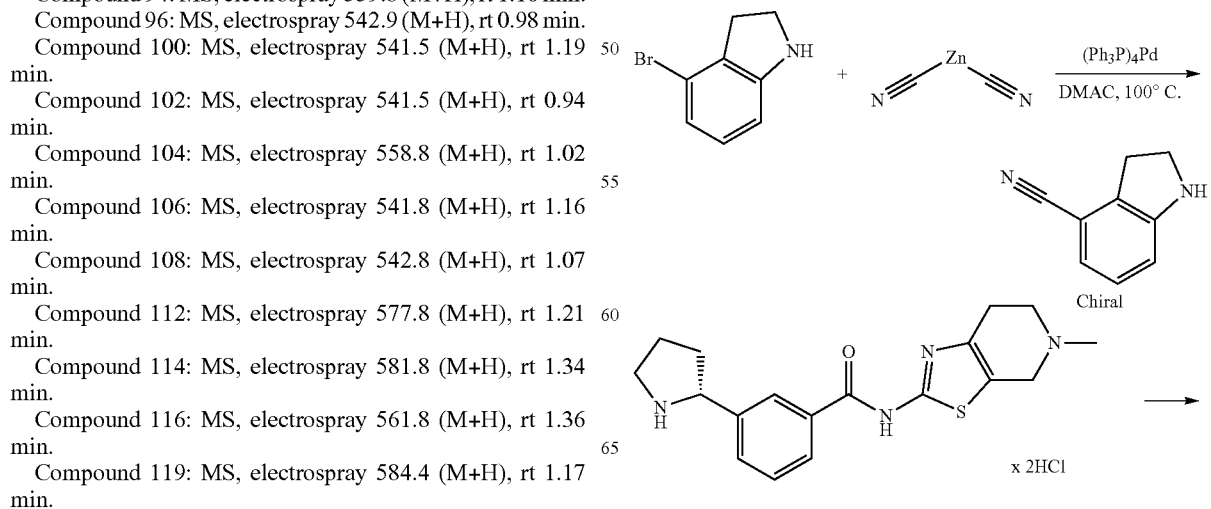

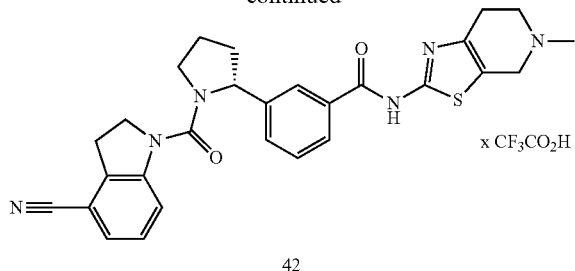

42

Degas a solution of 4-bromo-2,3-dihydro-1H-indole (250 mg, 1.224 mmol) in DMAC (2 mL) under Ar. To this add zinc cyanide (147 mg, 1.224 mmol) followed by tetrakis-(triphenylphosphine) palladium(0) (143 mg, 0.123 mmol) and heat the reaction under argon in a sealed tube at 100° C. for 4 h. Quench the cooled reaction with sat. NH$_4$Cl (50 mL) and extract with EtOAc (3×50 mL). Wash the organics with water (50 mL), dry (Na$_2$SO$_4$), then concentrate in vacuo to give a gum. Purify by silica gel chromatography eluting with 5% to 30% EtOAc/hexane. Pool and concentrate fractions containing product then dissolve the residue in Et$_2$O (5 mL) and hexane (50 mL). Reconcentrate this to a solid. Suspend in hexane and filter washing with hexane to afford 2,3-dihydro-1H-indole-4-carbonitrile as a powder (131 mg). MS, electrospray 145.2 (M+H), rt 1.02 min.

To a solution of 2,3-dihydro-1H-indole-4-carbonitrile (25 mg, 0.168 mmol) in acetonitrile (3 mL) add CDI (28 mg, 0.168 mmol) followed by DMAP (42 mg, 0.340 mmol) and stir the sealed vial at 90° C. for 4 h. Concentrate the reaction to dryness and add a solution of N-(5-methyl-4,5,6,7-tetrahydro-thiazolo[5,4-c]pyridin-2-yl)-3-(R)-pyrrolidin-2-yl-benzamide di-HCl (70 mg, 0.168 mmol) and Et$_3$N (5) (0.081 mL, 0.588 mmol) in DMF (3 mL). Stir the sealed vial at 90° C. for 4 h. Dilute the reaction with water (1 mL) and quench with TFA (0.3 mL). Purify this by reverse phase prep HPLC (10% to 90% CH$_3$CN/water. Pool and concentrate fractions containing product. Suspend the residue in EtOAc (3 mL) and precipitate with hexane (100 mL). Filter the solid, washing with hexane to afford the title compound as a solid (23 mg). MS, electrospray 514.0 (M+H), rt 1.26 min.

The following compound is prepared according to the procedure in Examples 21 using the appropriate starting materials:

Compound 110: MS, electrospray 583.8 (M+H), rt 1.36 min.

Example 22

Synthesis of 1-Oxo-1,2-dihydro-isoquinoline-6-carboxylic acid methyl ester

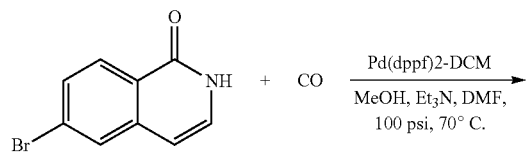

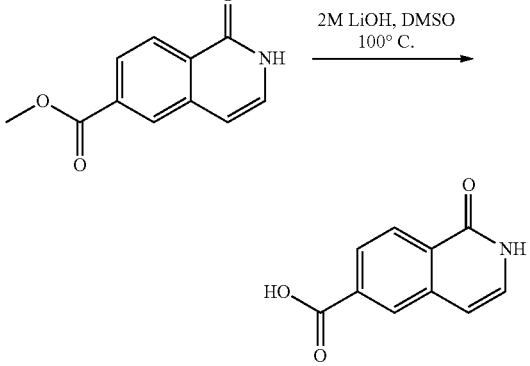

To a mixture of 6-bromo-2H-isoquinolin-1-one (4.00 g, 17.9 mmol), [1,1'-bis(diphenylphosphino)ferrocene]dichloropalladium (II) (750 mg, 0.92 mmol), triethylamine (9.0 mL, 65 mmol) in a Parr bomb add a 1:1 mixture (v/v) of DMF and MeOH. Seal the apparatus and flush with 100 psi of carbon monoxide (3×). Heat the reaction mixture at 70° C. with stifling for 15 h. Remove the solvent in vacuo and wash the residue with MeOH then crystallize from dichloromethane to give 3.11 g of the desired product 1-oxo-1,2-dihydro-isoquinoline-6-carboxylic acid methyl ester as an off white solid in 86% yield.

Heat 1-Oxo-1,2-dihydro-isoquinoline-6-carboxylic acid methyl ester (3.11 g, 15.3 mmol) in a mixture of DMSO and 2 M lithium hydroxide (30 mL) at 100° C. for 16 hours. Treat the reaction mixture with 1M hydrochloric acid, and collect the resulting white precipitate by filtration, rinsing with water and MeOH. Dry under high vacuum in the presence of P$_2$O$_5$ to give 2.87 g of the title compound.

The intermediate synthesized in Example 22 is used to prepare the compound listed below using appropriate intermediates and procedures analogous to those described in Examples 11, 14, 18 and 20:

Compound 72: MS, electrospray 515.1 (M+H), rt 1.04 min.

Example 23

Synthesis of 3,4-dimethoxy-N-{(R)-2-methylcarbamoyl-1-[3-(5-methyl-4,5,6,7-tetrahydro-thiazolo[5,4-c]pyridin-2-ylcarbamoyl)-phenyl]-ethyl}-benzamide trifluoroacetic acid (Compound 64)

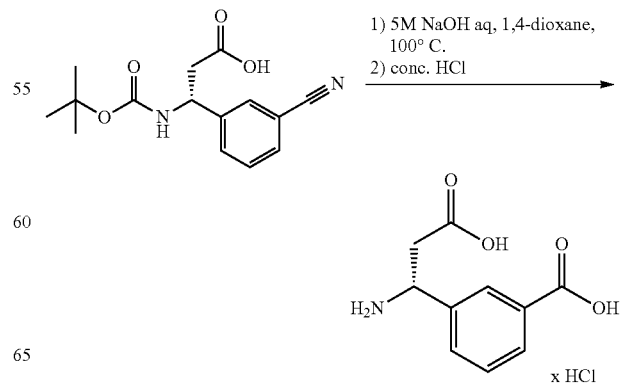

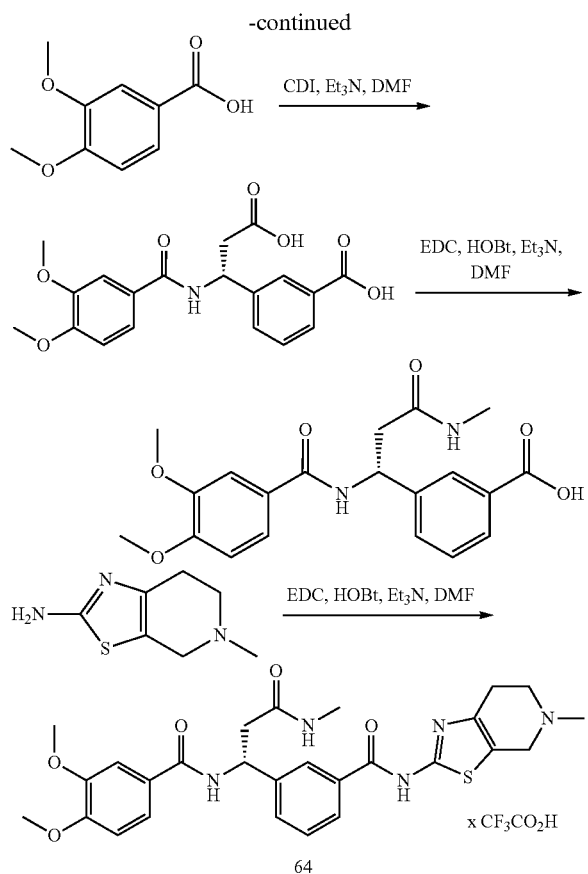

To solution of (R)-3-tert-butoxycarbonylamino-3-(3-cyano-phenyl)-propionic acid (2.0 g, 6.89 mmol) in 1,4-dioxane (30 mL) add 5M NaOH aq. solution (27.6 mL, 137.8 mmol and heat at 100° C. for 2.5 h. Dilute the crude reaction in water (100 mL) and cool to 5° C. in an ice bath. Quench portionwise by addition of glacial HOAc (8 mL), and further acidify by portionwise addition of conc. HCl (15 mL) to a final pH of 1 keeping internal temp <10° C. throughout. Wash the cold solution with EtOAc (2×200 mL). LCMS indicates the de-BOC product is trapped in the acidic aqueous layer. Concentrate the aqueous layer in vacuo at 35° C. to give a solid, containing desired product and organic salts). Dry this thoroughly in vacuo under $P_2O_5$ for 24 h, then pulverize the solid to a powder, triturate/sonicate in DMF (3×25 mL), and extract out the organic zwitterion product. Filter the extracts to remove residual inorganic salts then pool and concentrate in vacuo at 40° C. to give a gummy residue which was dried in vacuo under $P_2O_5$ to give 1.93 g of the semisolid intermediate 3-((R)-1-amino-2-carboxy-ethyl)-benzoic acid N,N-dimethyl-formamide complex as the HCl salt.

Stir a solution of 3,4-dimethoxybenzoic acid (2.318 g, 12.59 mmol) and CDI (2.063 g, 12.59 mmol) in DMF (75 mL) at room temperature for 1 h. To this add 3-((R)-1-amino-2-carboxy-ethyl)-benzoic acid N,N-dimethyl-formamide complex HCl salt (1.606 g, 5.04 mmol) followed by $Et_3N$ (2.47 mL, 17.63 mmol), and stir the solution at room temperature for 24 h. Remove the DMF in vacuo at 40° C. and dry the residue to a gum. Redissolve in EtOAc (200 mL). Wash with 0.5 M HCl (200 mL) then water (200 mL) and brine (100 mL). Extract the aqueous layers with more EtOAc (200 mL), and dry the organics ($Na_2SO_4$) then concentrate to a gummy residue. Purify this by silica gel chromatography eluting with 50% hexane/EtOAc to 100% EtOAc. Pool fractions containing desired product (Rf=0.10 100% EtOAc) and triturate the residue in EtOAc/hexane to afford 693 mg 3-[(R)-2-carboxy-1-(3,4-dimethoxy-benzoylamino)-ethyl]-benzoic acid as a solid.

To a solution of 3-[(R)-2-carboxy-1-(3,4-dimethoxy-benzoylamino)-ethyl]benzoic acid (100 mg, 0.268 mmol), HOBt (42 mg, 0.295 mmol), and EDC (58 mg, 0.295 mmol) in DMF (2 mL) add $Et_3N$ (0.149 mL, 1.072 mmol). Stir this at room temperature for 2 h, then add 2 M methylamine in THF solution (1.34 mL, 2.68 mmol) and stir the solution at room temperature for 24 h. Dilute the reaction with water (1 mL) and quench with conc. HCl (a few drops). Extract with EtOAc (3×50 mL), wash the organics with water (50 mL) and brine (50 mL) and dry ($Na_2SO_4$) and concentrate to a residue in vacuo then dry under $P_2O_5$. Triturate the solid in MeOH/EtOAc and filter off the inorganic salts. Concentrate the filtrate and dry in vacuo to a residue. Triturate this in EtOAc/hexane to give 164 mg of 3-[(R)-1-(3,4-dimethoxy-benzoylamino)-2-methylcarbamoyl-ethyl]-benzoic acid as a hydroscopic solid.

To a solution of 3-[(R)-1-(3,4-dimethoxy-benzoylamino)-2-methylcarbamoyl-ethyl]-benzoic acid (164 mg, 0.424 mmol), HOBt (127 mg, 0.89 mmol), and EDC (174 mg, 0.89 mmol) in DMF (5 mL) add $Et_3N$ (0.295 mL, 2.12 mmol). Stir this at room temperature for 1 h. To this add 5-methyl-4,5,6,7-tetrahydro-thiazolo[5,4-c]pyridin-2-ylamine (179 mg, 1.06 mmol) and stir the solution at room temperature for 24 h. Dilute the reaction with water (2 mL) and TFA (0.3 mL and purify by reverse phase prep HPLC. Pool fractions containing product (impure), concentrate in vacuo at 40° C. and further purify by silica gel chromatography eluting with 100% methylene chloride to 25% MeOH/methylene chloride. Pool and concentrate fractions containing product and triturate in $Et_2O$/hexane to afford 1 mg of the title compound as a solid. MS, electrospray 538.5 (M+H), rt 1.03 min.

Example 24

Synthesis of N—[(S)-6-(2-Cyano-ethylamino)-4,5,6,7-tetrahydro-benzothiazol-2-yl]-3-[(4-cyano-phenylcarbamoyl)-methoxy]-benzamide (Compound 142)

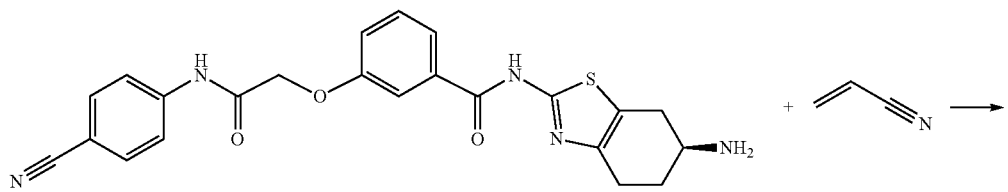

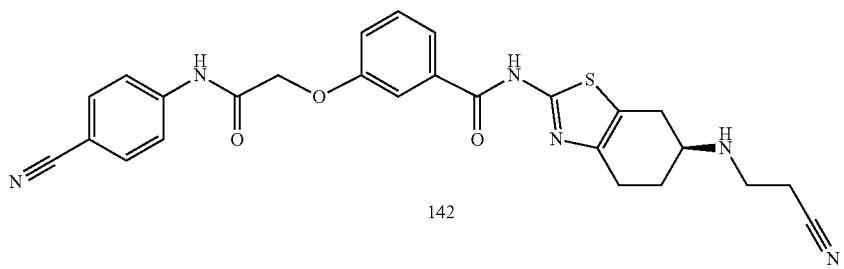

142

Prepare the free base of N—((S)-6-amino-4,5,6,7-tetrahydro-benzothiazol-2-yl)-3-[(4-cyano-phenylcarbamoyl)-methoxy]-benzamide trifluoroacetate salt by adding concentrated aq. Na₂CO₃ to 50 mg and extracting 4× with a MeOH-EtOAc mixture, washing with H₂O, and concentrating in vacuo to dryness to get 45 mg solid. Heat a suspension of the free base (22.8 mg, 0.051 mmol) and acrylonitrile (34 microL, 0.51 mmol) in 1 mL EtOH at 75° C. overnight. Remove the EtOH in vacuo and purify the on a prep plate in 5% MeOH/methylene chloride and the lower of 3 bands is eluted with 25% MeOH/methylene chloride and concentrate in vacuo to provide 4.9 mg impure product. Re-develop twice on a 0.5 mm prep plate in 5% MeOH/methylene chloride and the lower of 2 bands and concentrate to get 2.7 mg of the title compound; MS, electrospray 501.67 (M+H), rt 1.39 min.

Example 25

Synthesis of N-{(S)-6-[bis-(3,3,3-trifluoro-propyl)-amino]-4,5,6,7-tetrahydro-benzothiazol-2-yl}-3-[(4-cyano-phenylcarbamoyl)-methoxy]-benzamide (Compound 144) and 3-[(4-cyano-phenylcarbamoyl)-methoxy]-N—[(S)-6-(3,3,3-trifluoro-propylamino)-4,5,6,7-tetrahydro-benzothiazol-2-yl]-benzamide (Compound 146)

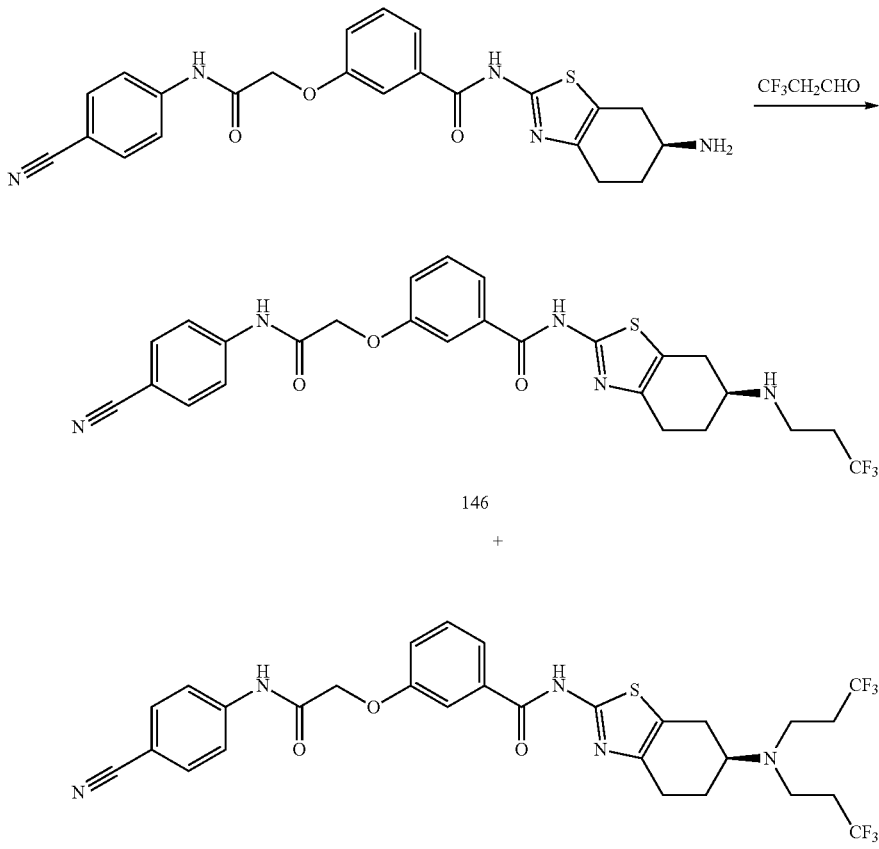

Stir a solution of N—((S)-6-amino-4,5,6,7-tetrahydro-benzothiazol-2-yl)-3-[(4-cyano-phenylcarbamoyl)-methoxy]-benzamide (21.2 mg, 0.047 mmol), 3,3,3-trifluoropropionaldehyde (53 mg, 0.470 mmol) and 20 µL HOAc in 1 mL 30% MeOH/CH$_2$Cl$_2$ for 0.5 hr and then add sodium cyanoborohydride (5 mg, 0.235 mmol) with stifling for another 1.5 h. Remove the solvent in vacuo, add aq. Na$_2$CO$_3$, and extract the solution 4× with EtOAc, wash twice with H$_2$O, dry, and concentrate in vacuo. Purify the residue on a prep plate eluting with 5% MeOH/methylene chloride, and isolate 2 bands. Concentrate in vacuo. The upper band affords 8.6 mg Compound 144; MS, electrospray 640.71 (M+H), rt 2.04 min. The lower band affords 8.8 mg (33%)

Compound 146; MS, electrospray 544.69 (M+H), rt 1.55 min.

Example 26

Synthesis of 6-(4-Cyclopropyl-piperazin-1-yl)-4,5,6,7-tetrahydro-benzothiazol-2-ylamine

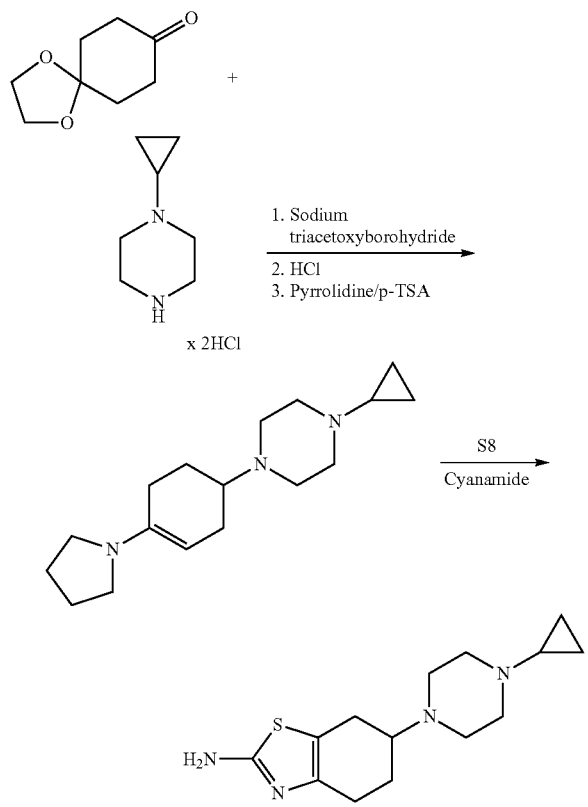

Add AcOH (300 mg, 5.00 mmol) and sodium triacetoxyborohydride (1590 mg, 7.50 mmol) to a solution of 1,4-dioxaspiro[4.5]decan-8-one (781 mg, 5.00 mmol) and 1-cyclopropyl-piperazine dihydrochloride salt (1095 mg, 5.50 mmol) in acetonitrile (40 mL). Stir the reaction mixture at room temperature overnight. Adjust the pH of this mixture to basic with 3M NaOH and extract with EtOAc. Dry the organic layer over Na$_2$SO$_4$ and evaporated to give an oil (1233 mg).

Treat this oil product with aq. HCl solution (6 M, 20 mL) while stirring at room temperature for 6 h. Adjust the pH of this mixture to basic with 3M NaOH and extract with methylene chloride. Dry the organic layer over Na$_2$SO$_4$ and evaporate to give an oil (990 mg).

Dissolve the above oil and pyrrolidine (348 mg, 4.9 mmol) in cyclohexane (30 mL), followed by addition of p-TSA monohydrate (85 mg, 0.45 mmol). Reflux the reaction mixture for 6 h with a Dean-Stark trap. Collect the cyclohexane and mix the orange residue remaining with ether (2×50 mL) with stifling at room temperature for 5 min. Combine all organic layers and concentrate to give crude 1-cyclopropyl-4-(4-pyrrolidin-1-yl-cyclohex-3-enyl)-piperazine intermediate as a colorless oil (1156 mg).

Add sulfur (134 mg, 0.52 mmol), and cyanamide (176 mg, 4.2 mmol) in MeOH (10 mL) to a solution of 1-cyclopropyl-4-(4-pyrrolidin-1-yl-cyclohex-3-enyl)-piperazine in MeOH (20 mL). Stir the mixture at 40° C. for 6 h. Concentrate the mixture and purify the residue in Biotage (MeOH/DCM: 0-10%) to give the title compound as a brown oil (542 mg, 46%). MS, electrospray 279.65 (M+H), rt 0.19 min The following fragments are prepared according to the procedure in Example 26 using the appropriate starting materials:

6-(2-Methoxy-ethyl)-6-methyl-4,5,6,7-tetrahydro-benzothiazole-2,6-diamine MS, electrospray 242.52 (M+H), rt 0.16 min 6-(4-Methyl-piperazin-1-yl)-4,5,6,7-tetrahydro-benzothiazol-2-ylamine MS, electrospray 253.58 (M+H), rt 0.17 min Example 27

Synthesis of 3-[(R)-1-(7-Cyano-imidazo[1,2-a]pyridine-2-carbonyl)-pyrrolidin-2-yl]-N-(5-methyl-4,5,6,7-tetrahydro-thiazolo[5,4-c]pyridin-2-yl)-benzamide (Compound 148)

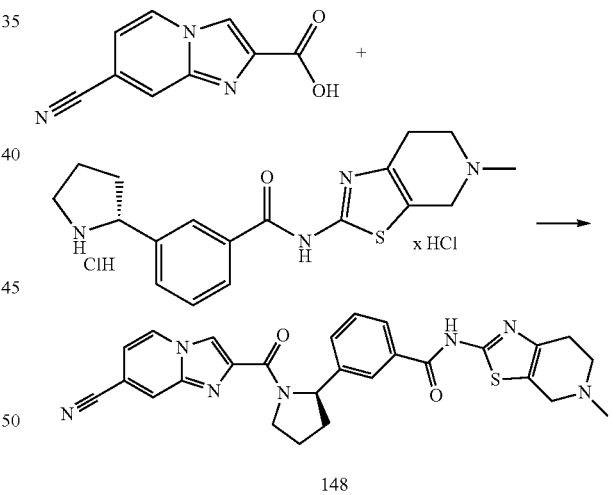

148

Mix 7-cyano-imidazo[1,2-a]pyridine-2-carboxylic acid (40 mg, 0.214 mmol) and TBTU (82 mg, 0.256 mmol) in DMF (4 mL) and stir for 30 min at room temperature. Add N-(5-methyl-4,5,6,7-tetrahydro-thiazolo[5,4-c]pyridin-2-yl)-3-(R)-pyrrolidin-2-yl-benzamide dihydrochloride salt (89 mg, 0.214 mmol) and triethyl amine (108 mg, 1.07 mmol). Stir the mixture overnight. Filter the reaction mixture and purify the filtrate by Prep HPLC system (5%-80% CH$_3$CN/H$_2$O) to give 63 mg (57%) of the title compound. MS, electrospray 512.21 (M+H), rt 0.53 min.

The following compounds are prepared according to the procedure in Example 27 using the appropriate starting materials:

Compound 150: MS, electrospray 512.20 (M+H), rt 0.52 min.
Compound 152: MS, electrospray 557.69 (M+H), rt 1.44 min.
Compound 154: MS, electrospray 531.75 (M+H), rt 1.35 min
Compound 156: MS, electrospray 520.68 (M+H), rt 1.44 min

ASSESSMENT OF BIOLOGICAL ACTIVITY

Molecular Assays

The compounds of the invention may be evaluated in one or both of the following two molecular assays:
1. Luciferin-Luciferase Assay The activity of ROCKII (1-543) kinase was measured utilizing Cambrex PKLight ATP Detection Reagent, a homogeneous assay technology using luciferin-luciferase to quantify residual ATP. The assay was performed in 384-well low-volume, white, non-binding surface microtiter plates (Corning). The assay buffer was 25 mM HEPES, pH 7.5, 10 mM $MgCl_2$, 50 mM KCl, 0.2% BSA, 0.01% CHAPS, 100 μM $Na_3VO_4$ and 0.5 mM DTT. Test compounds, dissolved in neat DMSO at 500 μg/mL, were serially diluted for dose response for a final starting concentration of 3 μg/mL in 1% DMSO of assay buffer. ROCKII (1-543) (62,408Da) was diluted in assay buffer to a final concentration of 7.5 nM in a total volume of 15 μL. Positive controls were reaction mixtures containing no test compound; negative controls (blanks) were reaction mixtures containing no kinase. After 15 minutes of pre-incubation of the test compounds with the kinase, a mixture of ATP and peptide substrate (AKRRRLSSLRA) in assay buffer was added to each well for a final concentration of 750 nM ATP and 500 nM peptide, respectively. After 90 minutes of incubation of the kinase reaction at 28° C. temperature, 10 μL of PKLight ATP Detection Reagent (warmed to room temperature previously) was added to each well. The assay plate was incubated at room temperature for additional 15 minutes and then read on an Analyst in luminescence mode. Dose-response experiments for each of the test compounds were conducted in quadruplet. $IC_{50}$ values of test compounds represent 50% response of the positive control from the dose-response curve.
2. IMAP Assay This assay is performed using FAM S6 substrate peptide (Catalogue #R7184) and IMAP FP Screening Express Kit detection reagents from Molecular Devices (Sunnyvale, Calif.) in IMAP kinase reaction buffer (Tris-HCl, pH 7.2, 10 mM MgCl2, 0.05% NaN3, 0.1% phosphate-free BSA) containing 1 mM DTT. Test compounds dissolved in neat DMSO at 0.3 mg/mL are serially diluted 1 to 3 for concentration response in 100% DMSO. The DMSO serial dilutions are further diluted 33.33-fold in kinase reaction buffer, and 10 μL of this buffer dilution is transferred to Corning black 96-well half area NBS plates for a final top concentration of 3 μg/mL in 1% DMSO. 10 μL aliquot of 3 nM ROCKII (1-543) diluted in kinase reaction buffer is added to each assay well for a final concentration of 1 nM kinase. 10 μL of a mixture of 600 nM FAM S6 peptide and 300 μM ATP diluted in kinase reaction buffer is added to each well for a final concentration of 200 nM peptide and 100 μM ATP. The kinase reaction mixture is incubated for 60 minutes at room temperature. Positive controls are reaction mixtures containing no test compound and negative controls (blanks) are reaction mixtures containing no kinase. The kinase reaction is stopped by addition of 60 μL IMAP progressive binding reagent (Catalog #R7284) diluted 400-fold in 1× Binding buffer A. After 30 min of incubation at room temperature, the plates are read for fluorescence polarization on Analyst Plate Reader using Ex 485 nm, Em 530 nm, and FL 505 dichroic mirror. The mP signals are converted to percent of control (POC) values using the formula:

$POC=100*(Signal-BCTRL) \div (PCTRL-BCTRL)$

Where Signal is the test well signal, BCTRL is the average of background (negative control) well signals on the plate and PCTRL is the average of positive control well signals on the plate. For the concentration-responsive compounds, POC as a function of test compound concentration is fitted to a 4-parameter logistic equation of the form:

$Y=A+(B-A)/[1+(x/C)D]$

Where A, B, C, and D are fitted parameters (parameter B is fixed at zero POC), and x and y are the independent and dependent variables, respectively. The $IC_{50}$ is determined as the inflection point parameter, C.

Representative compounds of the present invention were tested for activity in one or both of the above assays. Preferred compounds have an $IC_{50}$<1,000 nM and more preferred compounds have an $IC_{50}$<100 nM in these assays. As examples the following data were obtained for the compounds named below:

| Compound Number (Table 1) | Assay 1 $IC_{50}$ (nM) | Assay 2 $IC_{50}$ (nM) |
| --- | --- | --- |
| 1 | 23.4 | |
| 2 | 2.8 | |
| 4 | 22.4 | |
| 5 | 19.1 | |
| 8 | 38.1 | |
| 9 | 1.7 | 2.2 |
| 10 | 5.7 | |
| 11 | 3.7 | 11 |
| 12 | 23.1 | |
| 13 | 3.4 | 8.5 |
| 14 | 3.8 | |
| 15 | 21.2 | |
| 16 | 5.8 | 23 |
| 18 | 6.0 | 19 |
| 19 | 35 | |
| 20 | 1.7 | 0.39 |
| 21 | 95.5 | |
| 22 | 2.6 | 1.0 |
| 23 | | 0.8 |
| 24 | 12.5 | |
| 26 | 1.7 | 5.8 |
| 28 | 6.0 | 44 |
| 29 | 1.6 | 0.8 |
| 30 | 33.4 | |
| 31 | 1.0 | 0.3 |
| 32 | 30.7 | |
| 33 | 1.2 | 0.5 |
| 34 | 45.1 | |
| 35 | 0.9 | 0.4 |
| 36 | 38.0 | |
| 37 | | 0.3 |
| 38 | 15.3 | |
| 39 | | 0.6 |
| 40 | 2.1 | 4.0 |
| 42 | 6.9 | 44.5 |
| 44 | 1.4 | 0.7 |
| 46 | 94.6 | |
| 47 | 17.8 | |
| 48 | 2.8 | 10 |
| 50 | 2.2 | 8.7 |
| 52 | 91.4 | |
| 53 | 11.5 | |
| 54 | 4.0 | 13 |
| 55 | 8.8 | |
| 56 | 80.4 | |
| 57 | 20.9 | |

-continued

| Compound Number (Table 1) | Assay 1 IC$_{50}$ (nM) | Assay 2 IC$_{50}$ (nM) |
|---|---|---|
| 58 | 6.1 | 16 |
| 59 | 22.4 | |
| 60 | | 4.1 |
| 61 | 74.4 | |
| 64 | | |
| 66 | 14.5 | |
| 70 | 2.6 | 11.2 |
| 74 | 2.5 | 7.4 |
| 77 | 5.4 | |
| 78 | 1.9 | 2.1 |
| 81 | 5.5 | |
| 82 | | 1.7 |
| 83 | 37.8 | |
| 84 | 20.8 | |
| 85 | 22.4 | |
| 86 | 44.9 | |
| 88 | | 3.8 |
| 89 | 3.9 | 13.0 |
| 90 | | 2.1 |
| 92 | | 1.3 |
| 93 | 9.0 | 29 |
| 94 | | 2 |
| 96 | | 0.8 |
| 97 | 3.1 | 5.8 |
| 98 | 6.2 | 11 |
| 100 | | 2 |
| 101 | 3.1 | 6.8 |
| 102 | 2.6 | 3.6 |
| 104 | | 1.7 |
| 105 | 12.5 | |
| 106 | | 1.9 |
| 108 | 2.3 | 3.6 |
| 109 | 9.5 | |
| 110 | 2.9 | 2.9 |
| 111 | 39.3 | |
| 112 | 3.6 | 6.8 |
| 114 | 5.8 | 7.9 |
| 115 | 77.5 | |
| 116 | 7.8 | 9.7 |
| 117 | 18.7 | |
| 118 | 2.5 | 6.9 |
| 120 | 3.2 | 7.9 |
| 122 | 3.5 | 8.3 |
| 124 | 2.3 | 6.7 |
| 126 | 2.7 | 7 |
| 128 | 3.6 | 29 |
| 130 | 2.5 | 6.3 |
| 132 | 2.6 | 17 |
| 134 | 2.7 | 30 |
| 136 | 2.6 | 6.9 |
| 138 | | 4.2 |
| 140 | 2.5 | 4.9 |
| 141 | 8.9 | |
| 142 | 5.2 | 27 |
| 143 | 14.0 | |
| 145 | 10.5 | |
| 146 | 5.1 | 32 |
| 147 | 18.9 | |
| 148 | 2.9 | 12 |
| 149 | 57.5 | |
| 150 | 25.5 | |
| 152 | 6.1 | 24 |
| 153 | 9.5 | |
| 154 | 6.5 | 33 |
| 155 | 9.7 | |
| 156 | 7.2 | 31 |
| 157 | 45.7 | |

METHODS OF THERAPEUTIC USE

In accordance with the invention, there are provided novel methods of using the compounds of formula (I). The compounds disclosed herein effectively inhibit Rho kinase. The inhibition of Rho kinase is an attractive means for preventing and treating a variety of cardiovascular diseases or conditions associated with Rho kinase activation. Thus, the compounds are useful for the treatment of diseases and conditions as described in the Background section, including the following conditions and diseases: hypertension, atherosclerosis, restenosis, stroke, myocardial infarction, heart failure, coronary artery disease, peripheral artery disease, coronary vasospasm, cerebral vasospasm, ischemia/reperfusion injury, pulmonary hypertension, angina, erectile dysfunction, renal disease and organ failure. As disclosed in the Background section, the compounds of the invention will also be useful for treating diseases or conditions associated with smooth muscle hyper reactivity or with activated Rho-kinase under other pathophysiological conditions. These diseases include but are not limited to asthma, glaucoma, cancer, Alzheimer's disease, multiple sclerosis, spinal cord injury, neuropathic pain, rheumatoid arthritis, psoriasis and inflammatory bowel disease.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of the formula I

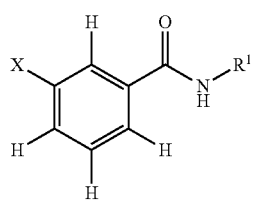

I wherein:

$R^1$ is selected from the group $R^{1a}$ consisting of

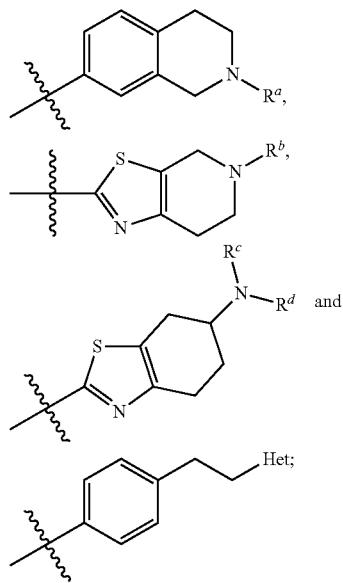

$R^a$ is selected from the group $R^{a1}$ consisting of H and $C_{1-6}$alkyl;
$R^b$ is selected from the group $R^{b1}$ consisting of $C_{1-6}$alkyl and benzyl;
$R^c$ and $R^d$ are independently selected from the group $R^{cd1}$ consisting of H, $C_{1-6}$alkyl, —$(CH_2)_2$OMe, —$(CH_2)_2$CF$_3$, and —$(CH_2)_2$CN; or
$R^c$ and $R^d$, together with the N they are bonded to, form a heterocycle selected from morpholine and piperazine, optionally substituted with cyclopropyl or methyl;
Het is selected from N-pyrrolidinyl and N-morpholinyl;

X is selected from the group $X^a$ consisting of

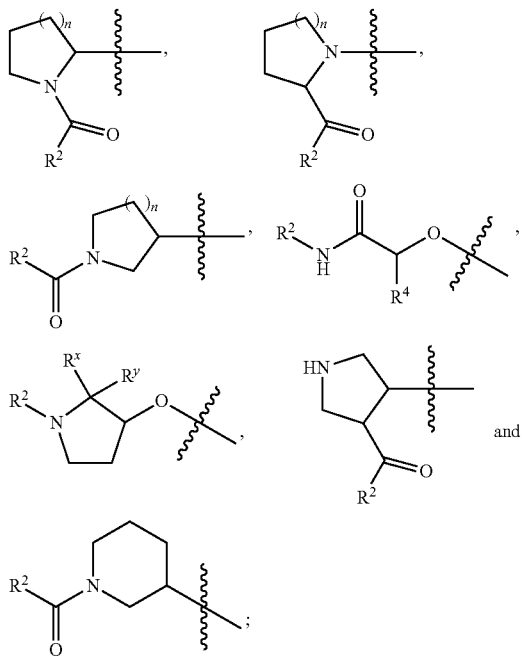

wherein n=1 or 2;
$R^x$ and $R^y$ are H; or
$R^x$ and $R^y$ taken together represent oxo;
$R^2$ is selected from the group $R^{2a}$ consisting of

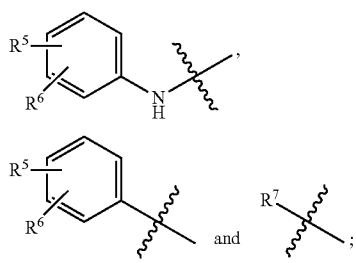

with the proviso that if $R^2$ is

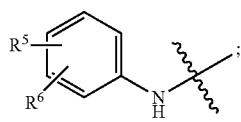

X is not

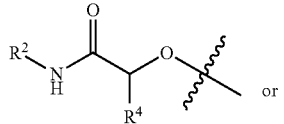

or

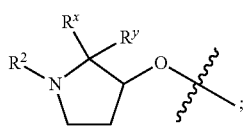
R⁴ is selected from H and —CH₃;
R⁵ and R⁶ are independently selected from H, —CH₃, —OCH₃, —C(O)NH₂, and —CN, provided that R⁵ and R⁶ are not both H;
R⁷ is selected from the group R⁷ᵃ consisting of
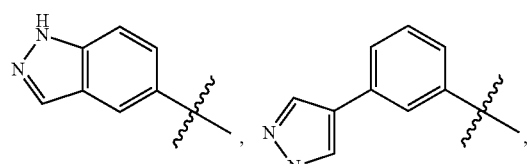
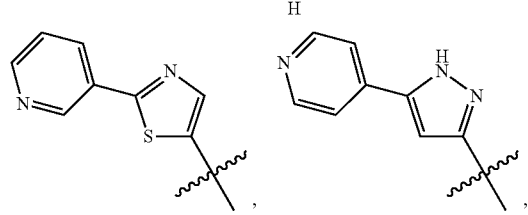
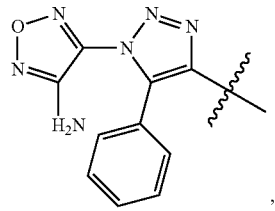
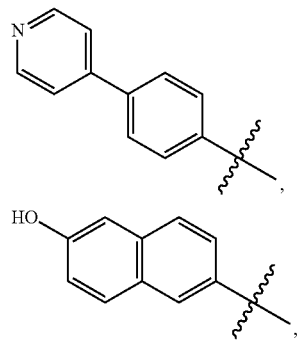
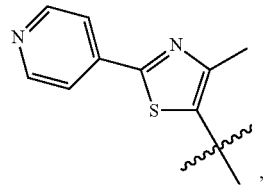
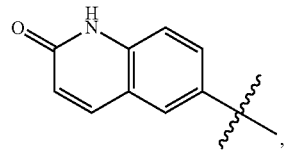
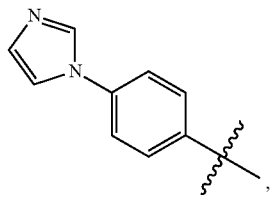
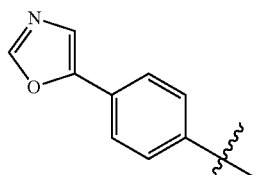
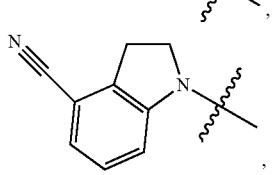
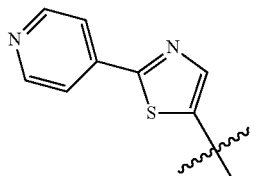
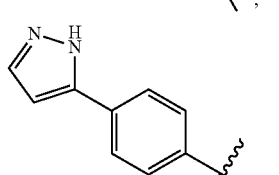
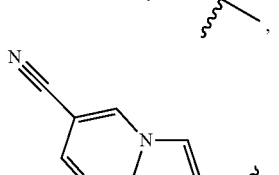
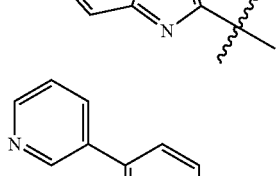
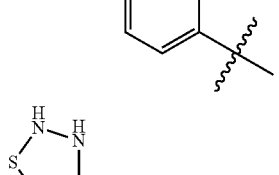
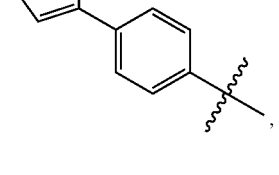

-continued

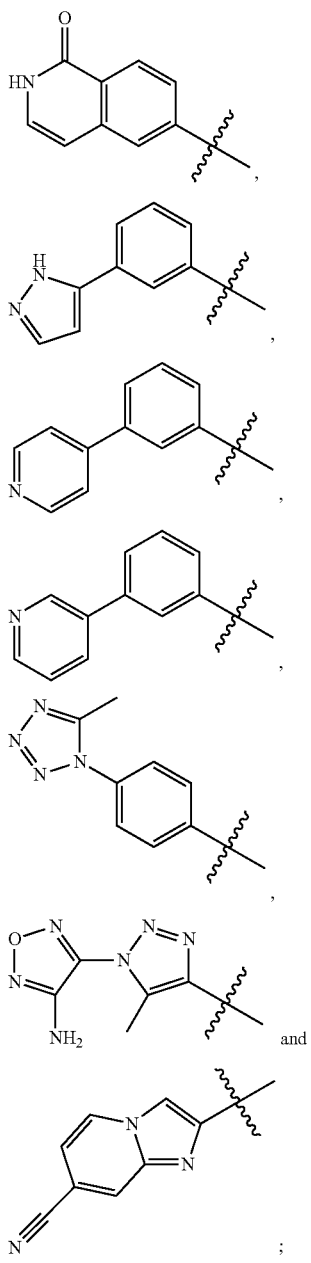

or a salt thereof.

2. The compound of claim 1 wherein $R^1$ is selected from the group $R^{1b}$ consisting of

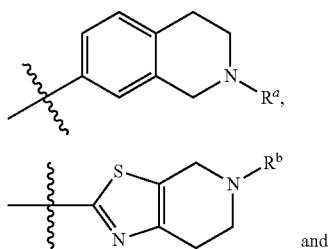
and

-continued

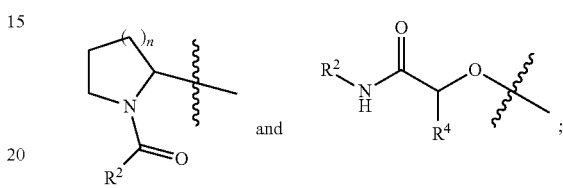

and
X is selected from the group $X^b$ consisting of

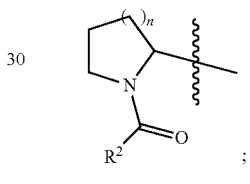

or a salt thereof.

3. The compound of claim 2 wherein X is selected from the group $X^d$ consisting of

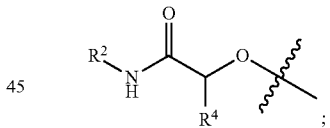

or a salt thereof.

4. The compound of claim 3 wherein n is 1; or a salt thereof.

5. The compound of claim 2 wherein X is selected from the group $X^e$ consisting of

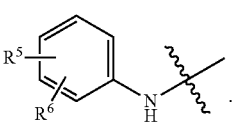

or a salt thereof, with the proviso that $R^2$ is not

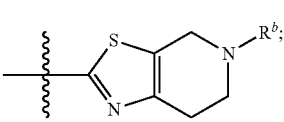

6. The compound of claim 2 wherein $R^1$ is selected from the group $R^{1d}$ consisting of

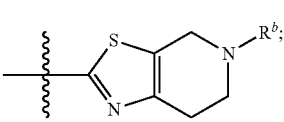

or a salt thereof.

7. The compound of claim 2 wherein R¹ is selected from the group $R^{1e}$ consisting of
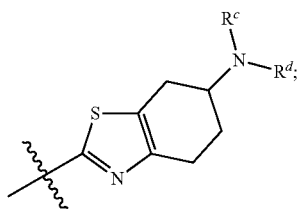
or a salt thereof.
8. The compound of claim 1 wherein R¹ is selected from the group $R^{1d}$ consisting of
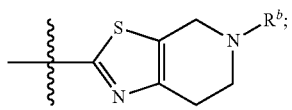
X is selected from the group $X^d$ consisting of
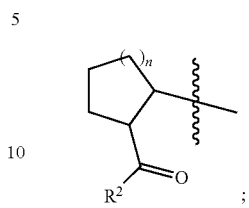
and
n=1;
or a salt thereof.
9. A compound selected from the group consisting of
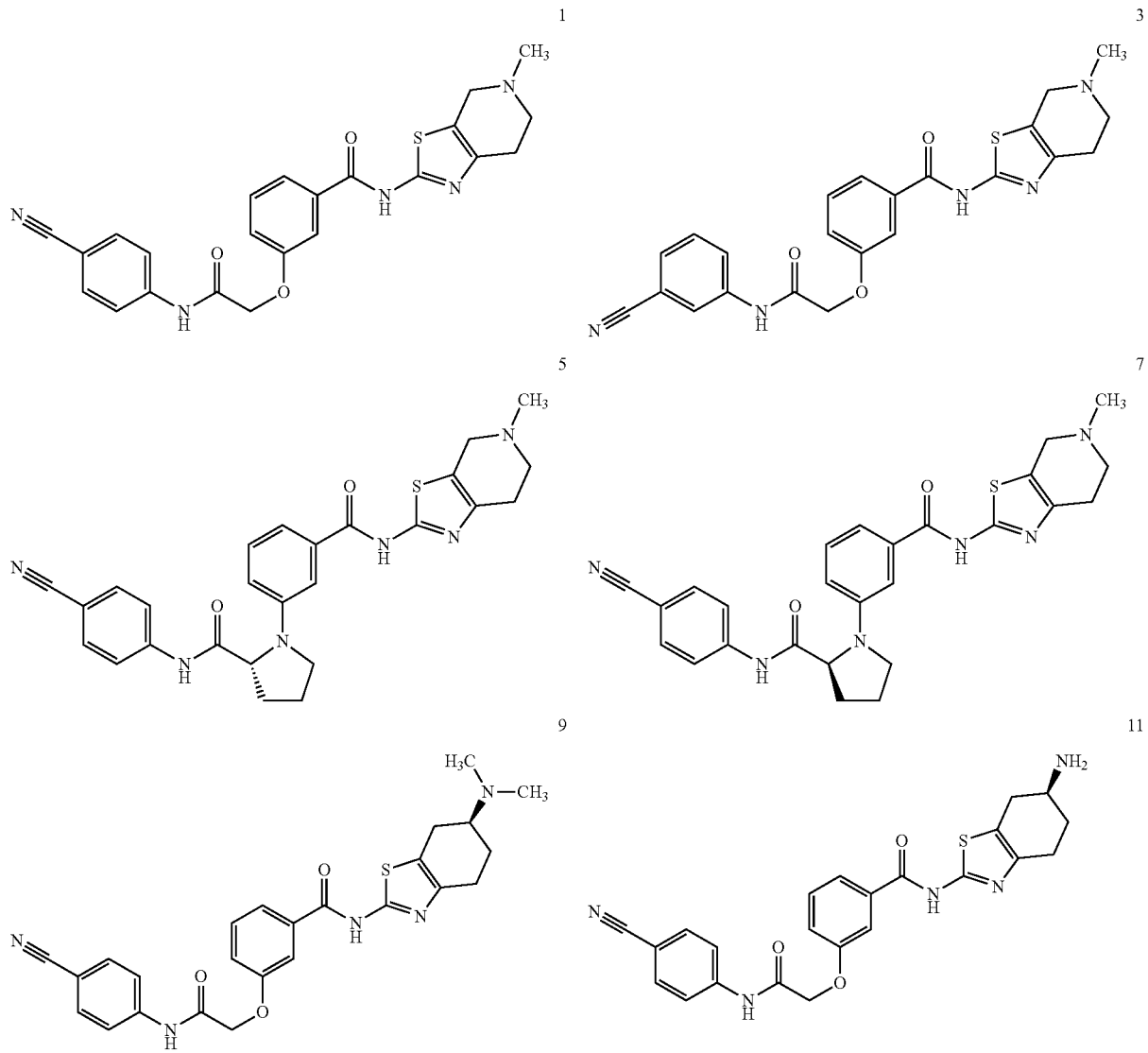

-continued
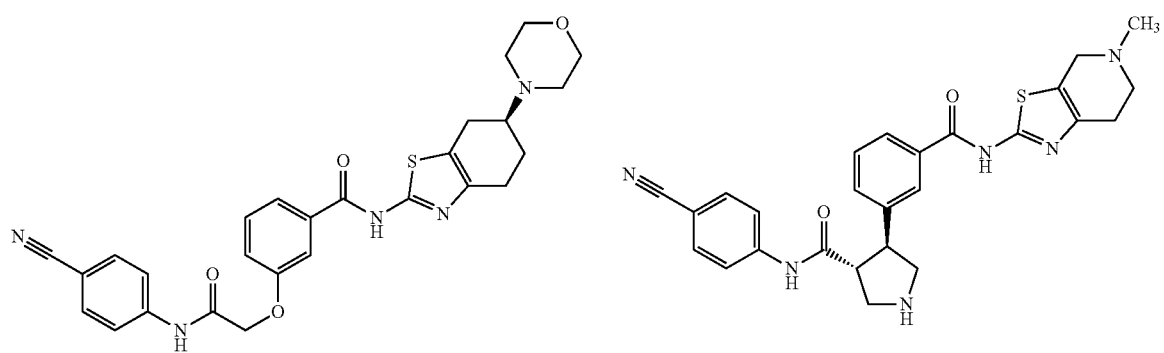
13
15
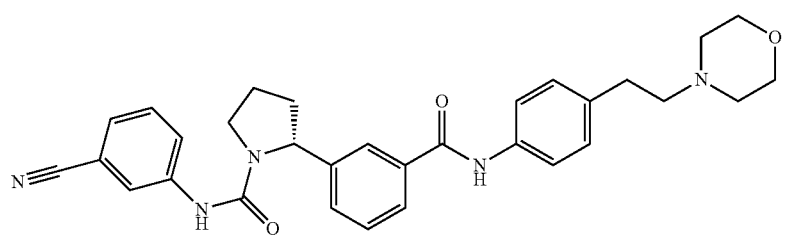
16
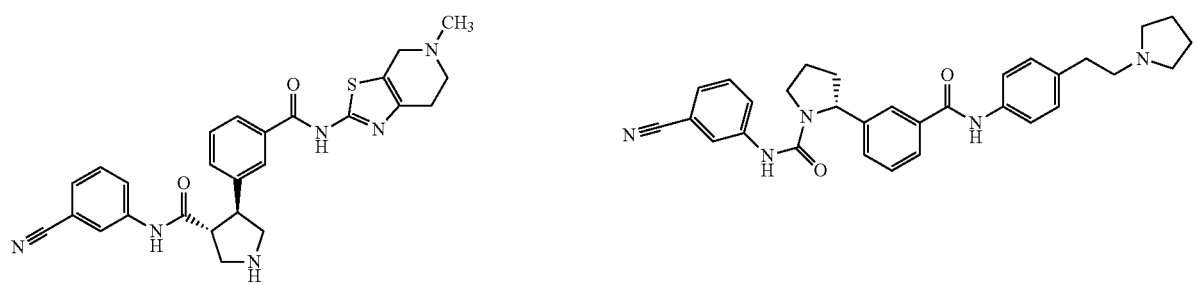
17
18
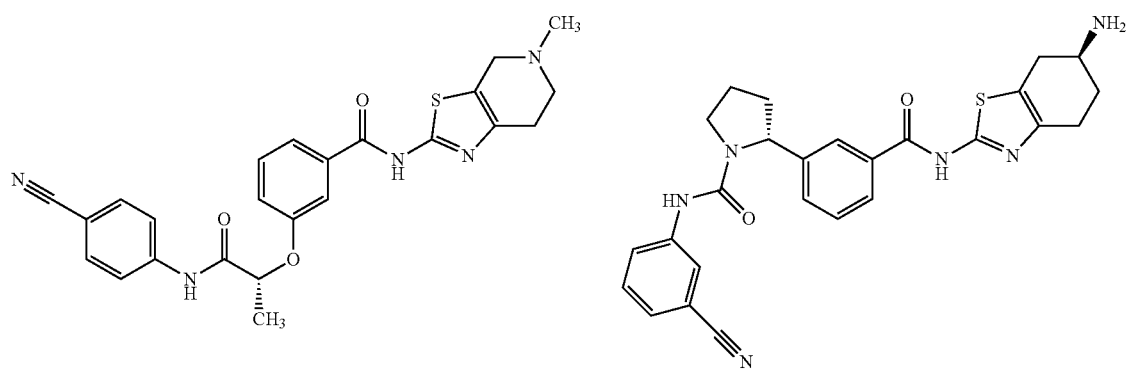
19
20

| 21 | 22 |
|---|---|
| 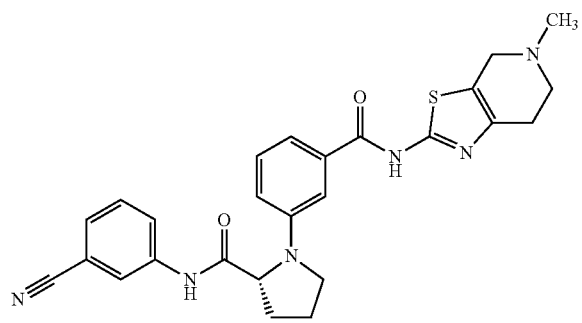 | 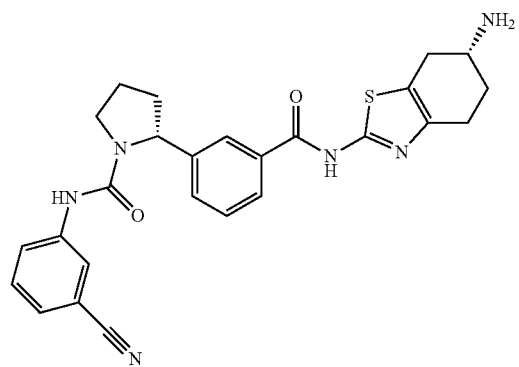 |
| 23 | 24 |
| 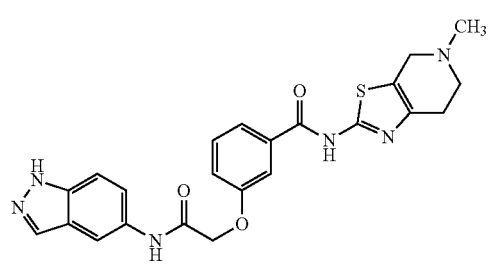 | 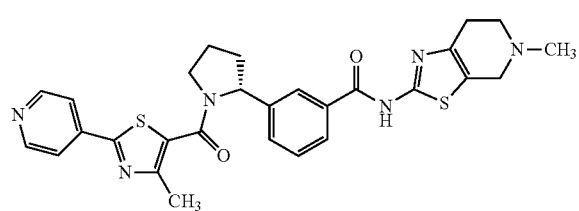 |
| 25 | 26 |
| 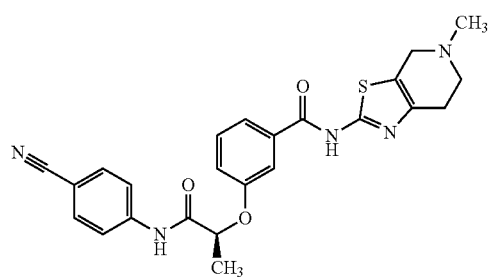 | 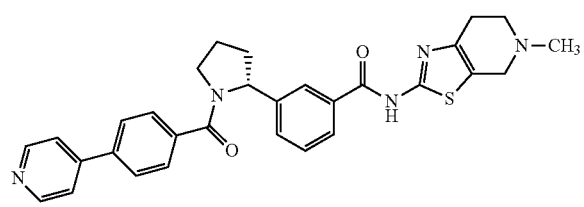 |
| 27 | 28 |
| 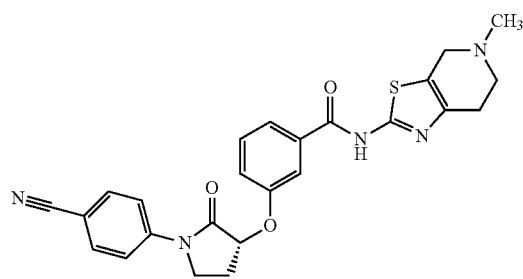 | 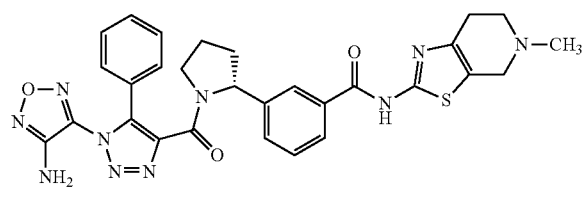 |
| 29 | 30 |
| 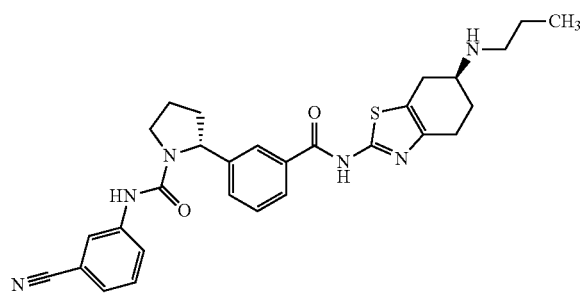 | 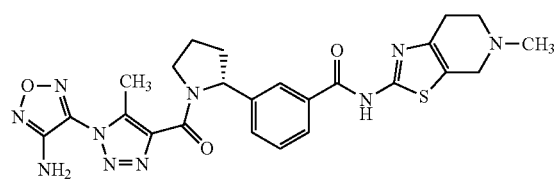 |

32
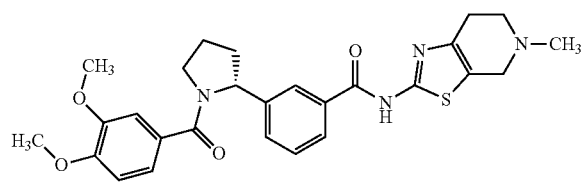
34
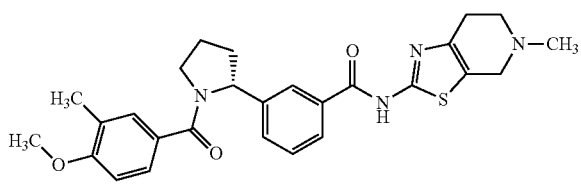
36
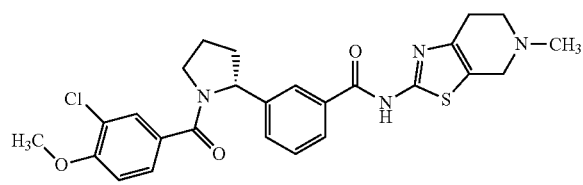
37
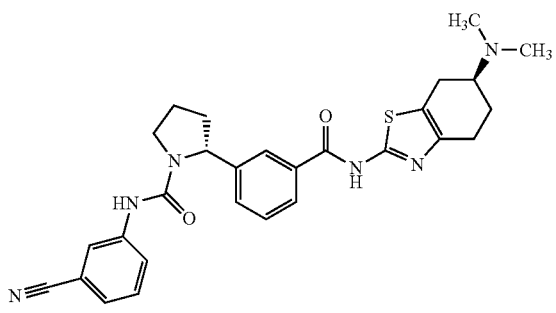
38
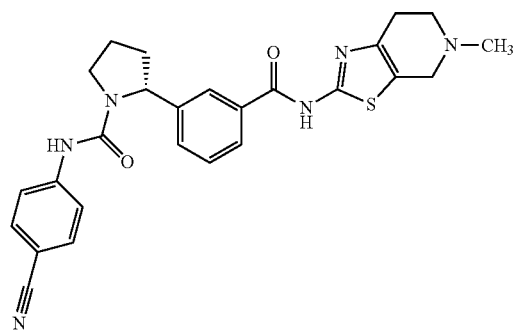
39
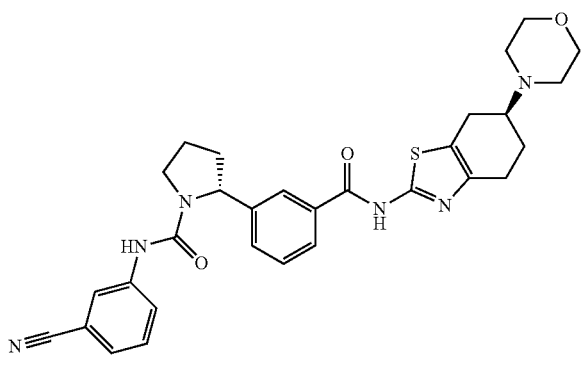
40
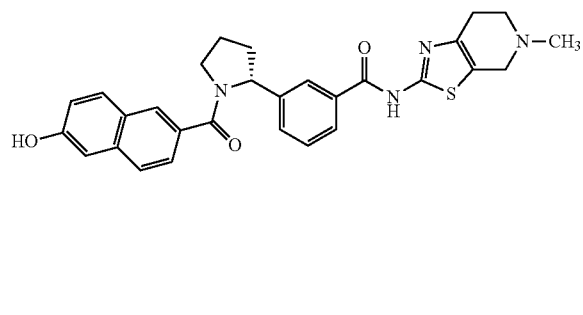
41
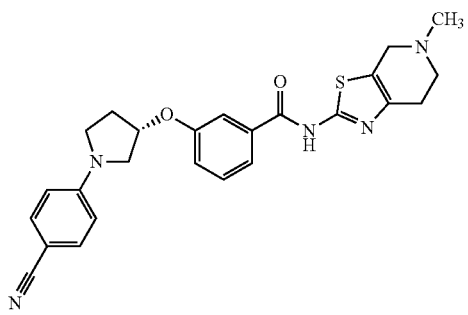
42
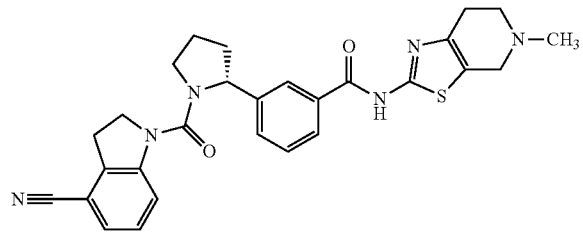
43
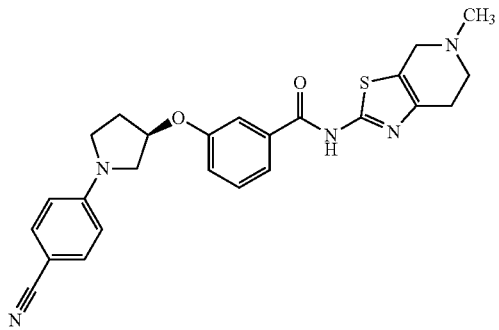

44
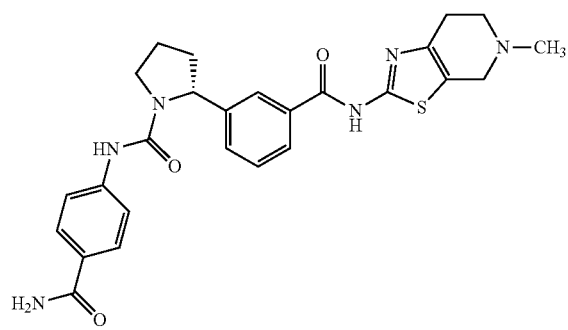
45
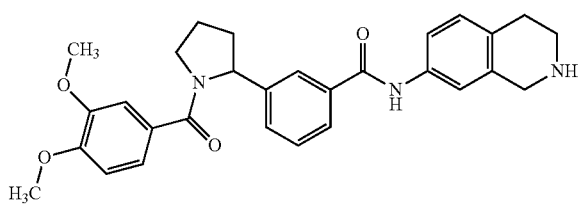
46
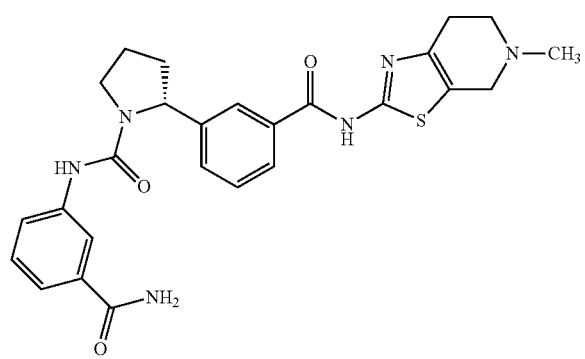
47
48
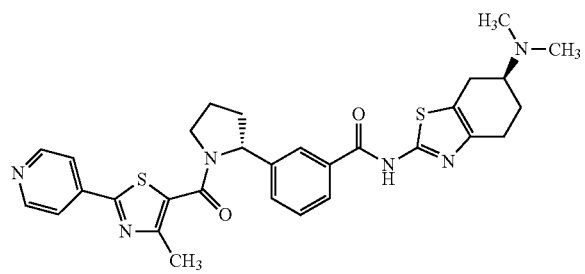
49
50
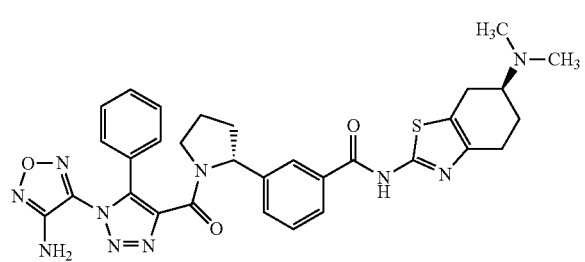
51
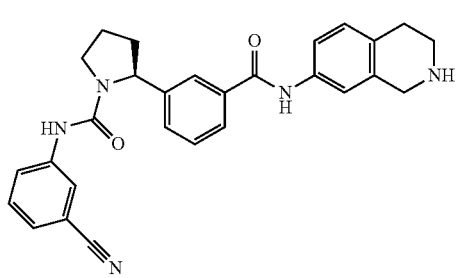
52
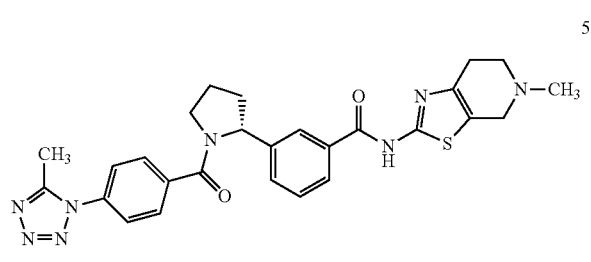
53
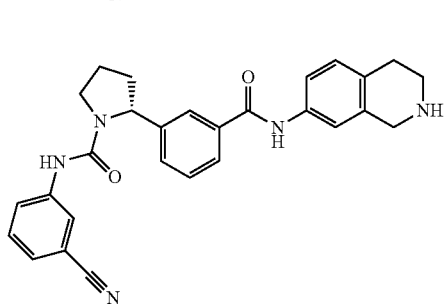

54
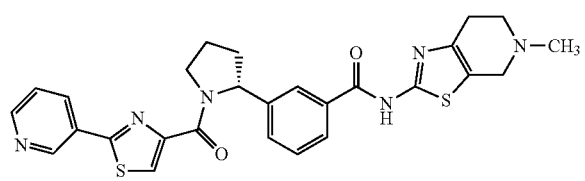
55
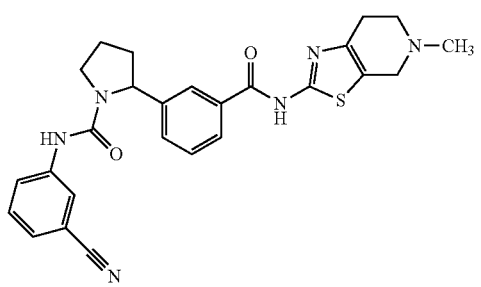
56
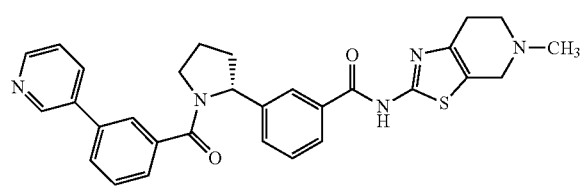
57
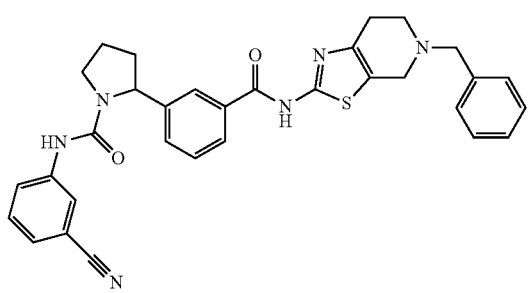
58
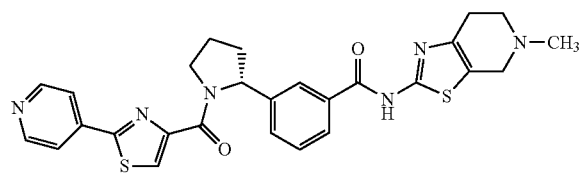
59
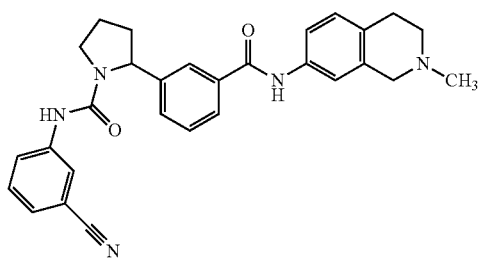
60
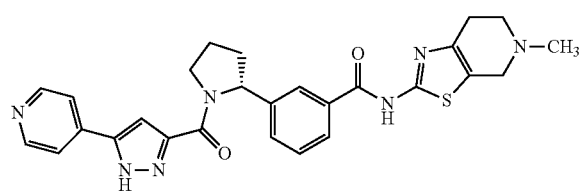
61
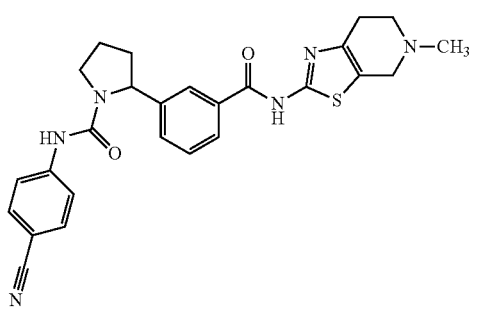
62
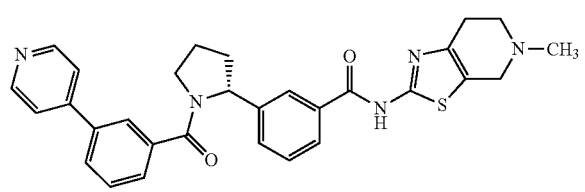
63
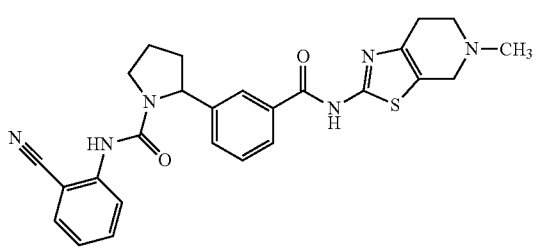

-continued
65
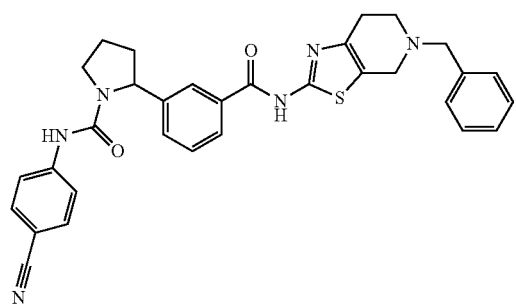
66
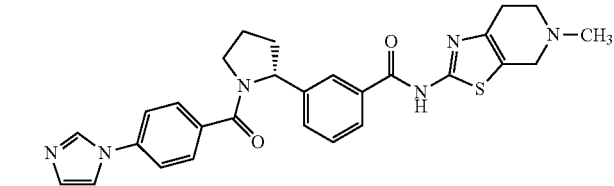
67
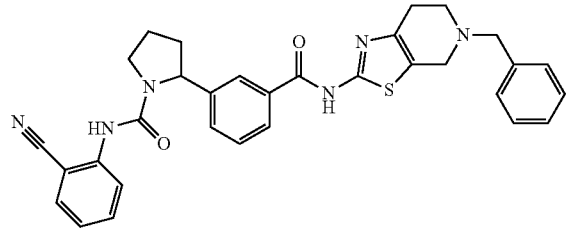
68
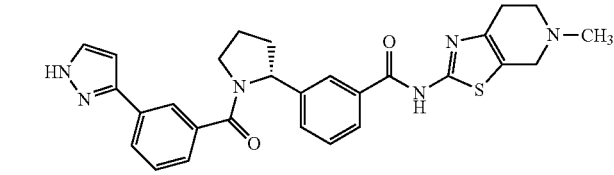
69
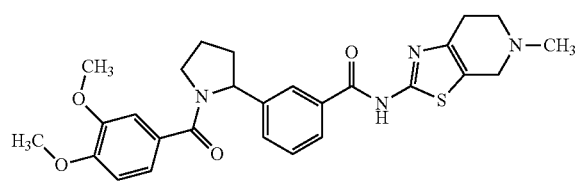
70
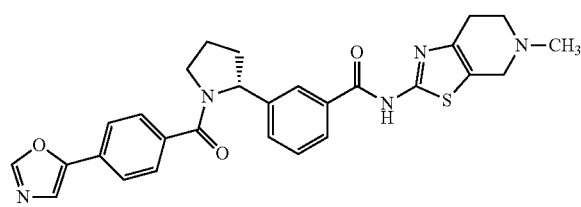
71
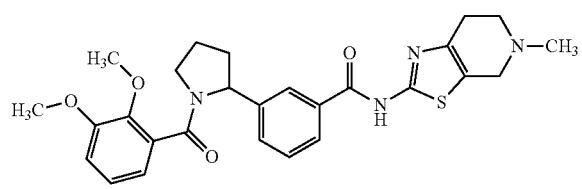
72
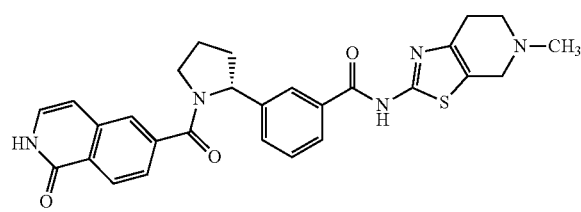
73
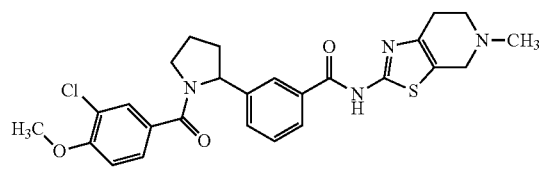
74
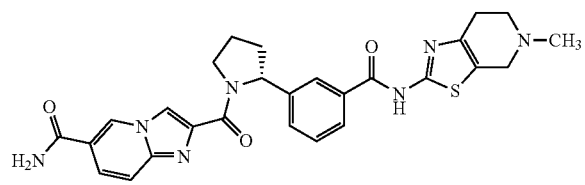
75
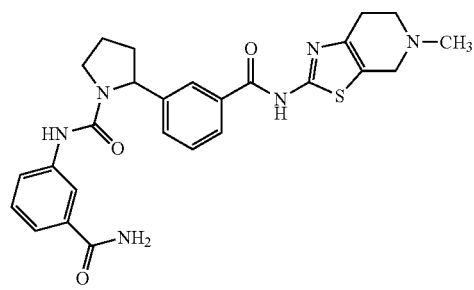
76
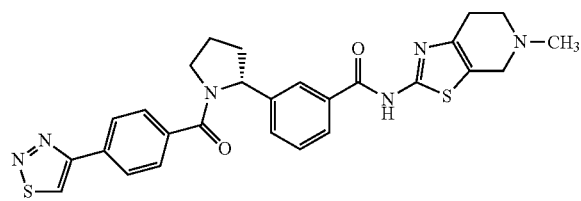

-continued
77
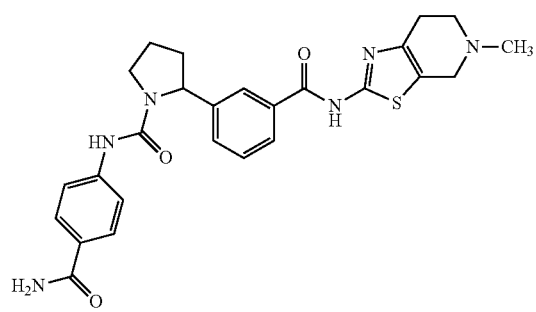
78
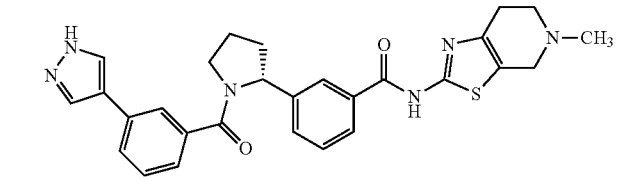
80
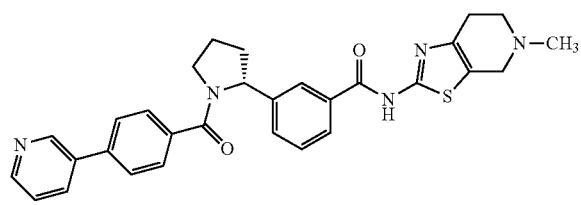
82
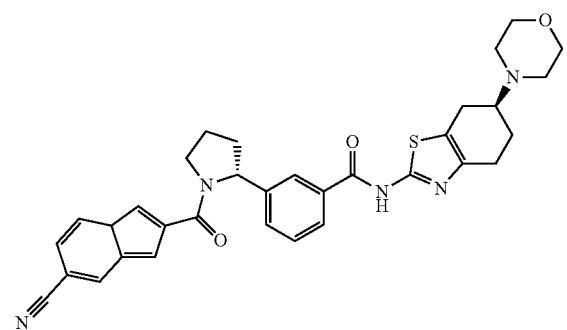
84
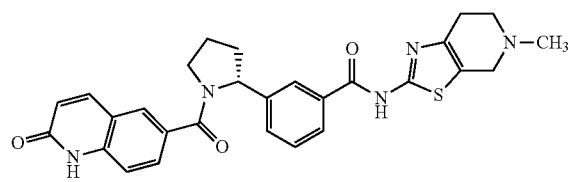
86
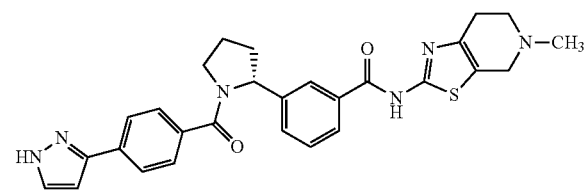
88
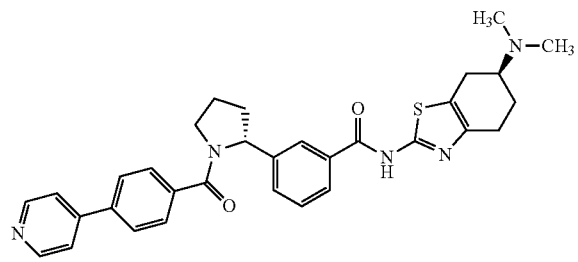
90
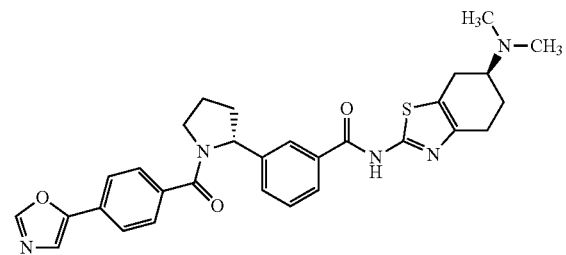
92
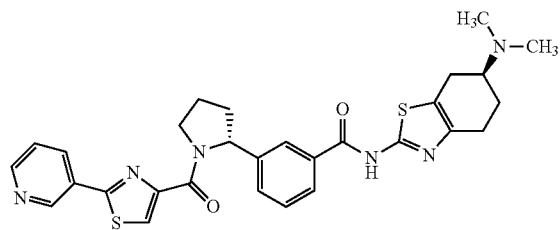
94
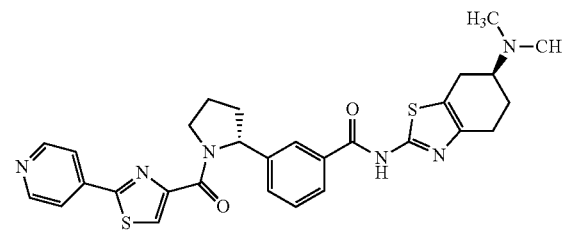

-continued
96
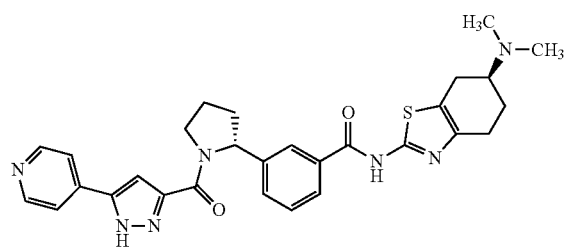
99
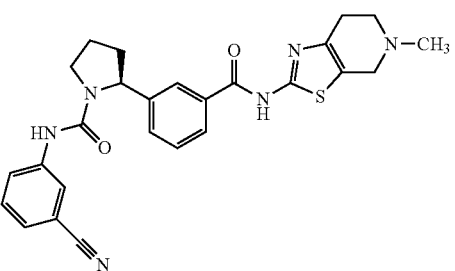
100
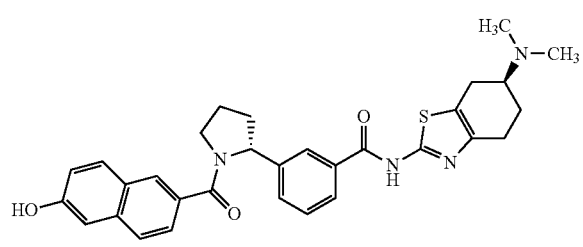
101
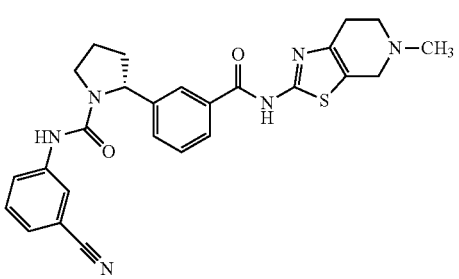
102
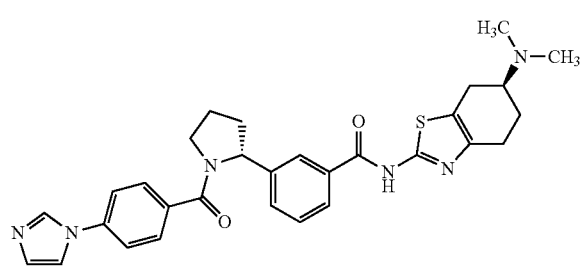
103
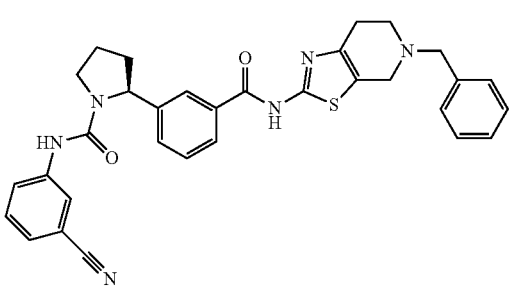
104
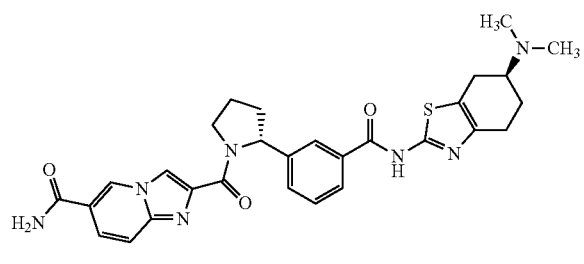
105
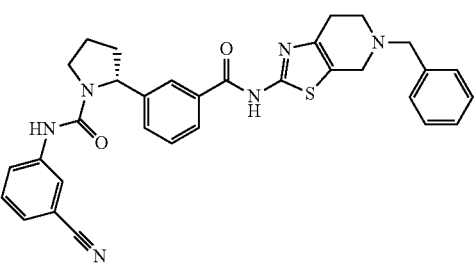
106
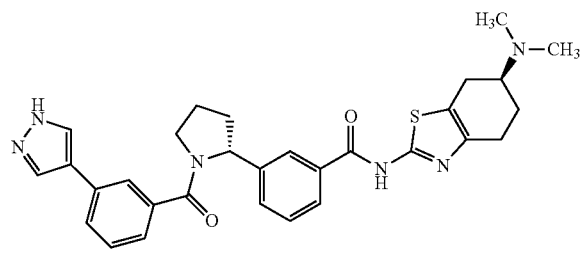
107
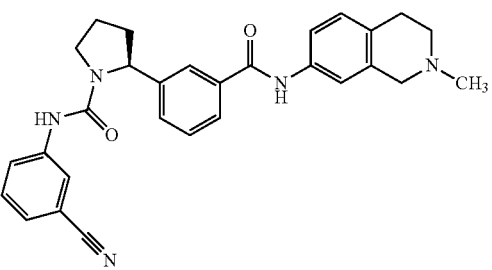

-continued
108
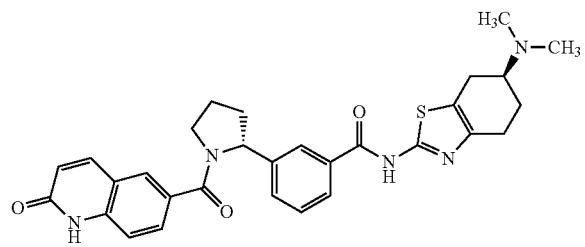
109
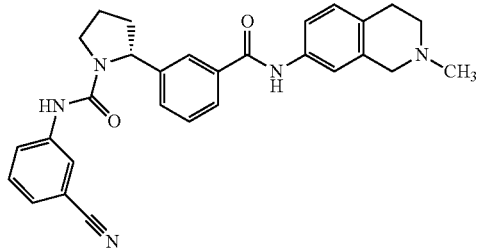
110
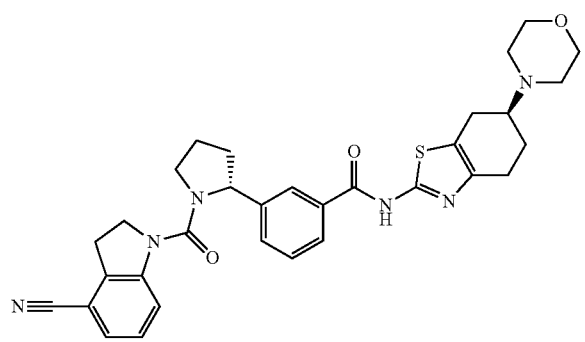
111
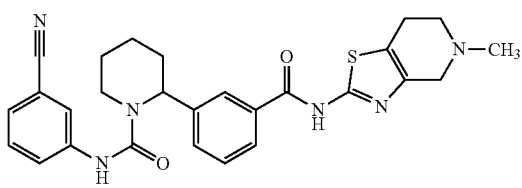
112
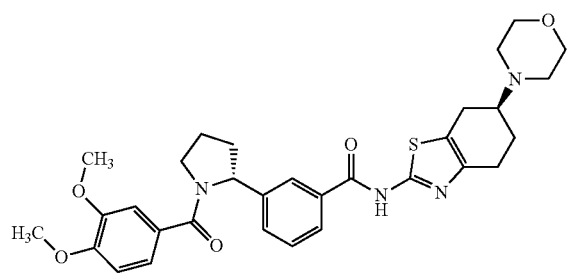
113
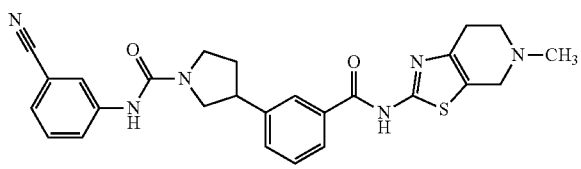
114
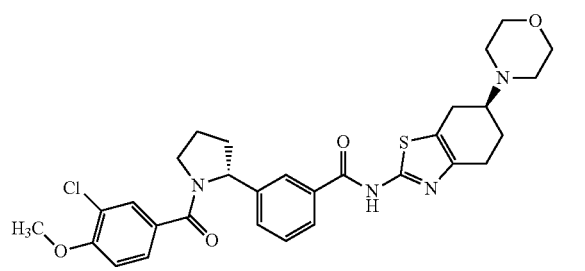
115
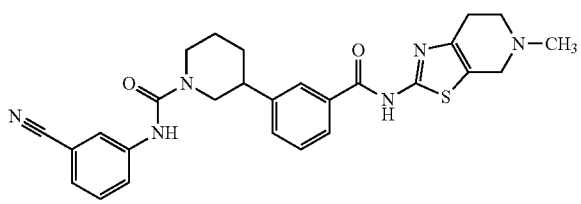
116
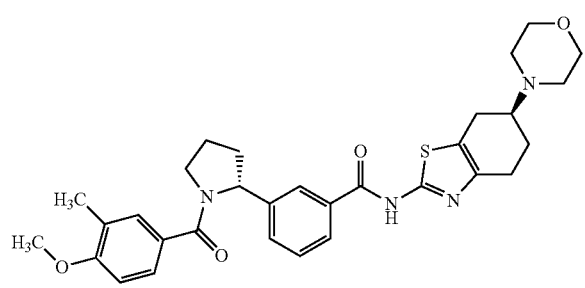
117
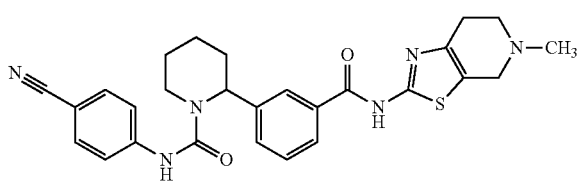

118
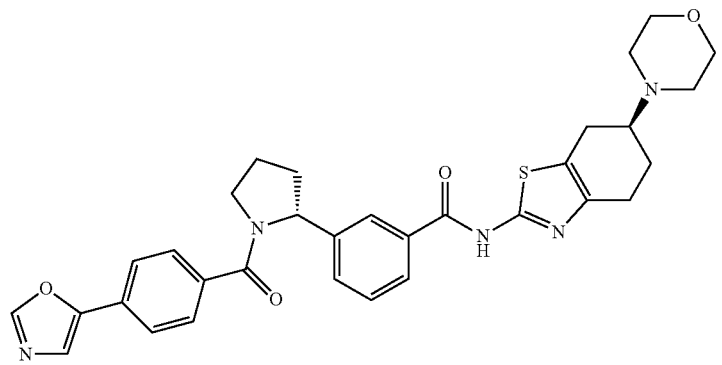
119
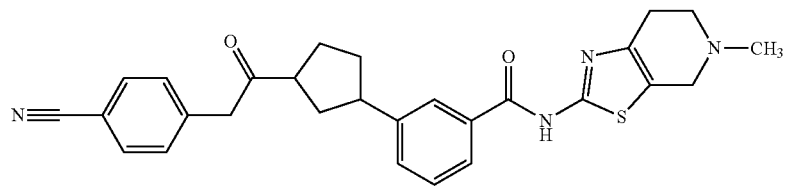
120
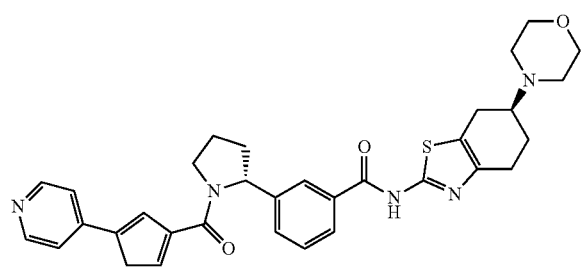
121
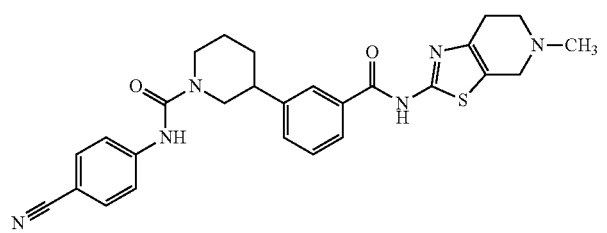
122
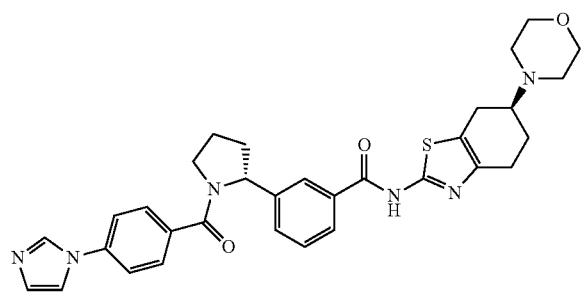
123
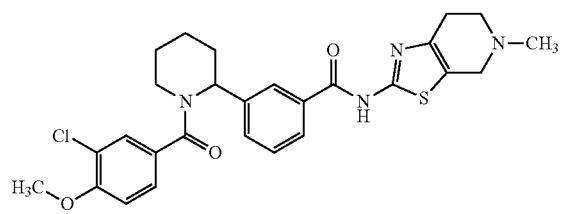
124
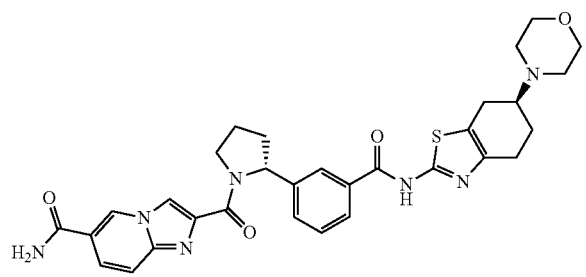
125
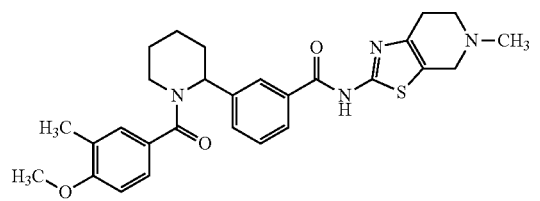

-continued
126
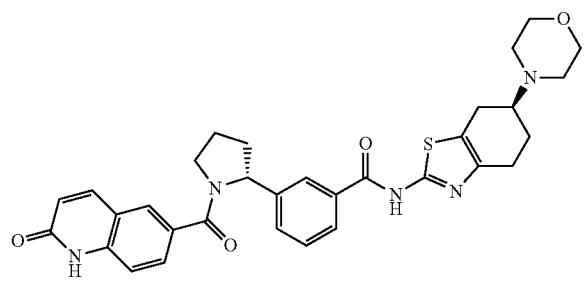
127
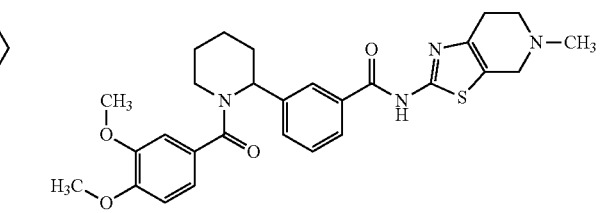
128
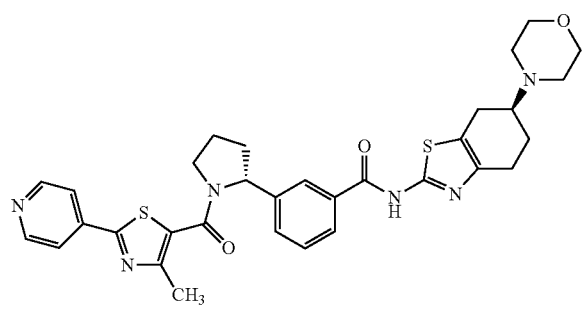
129
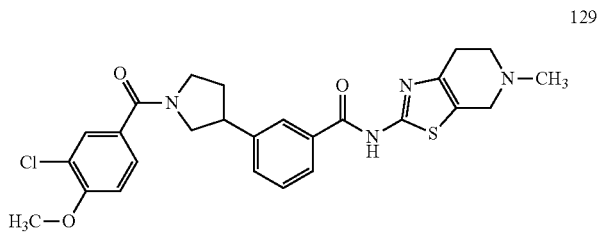
130
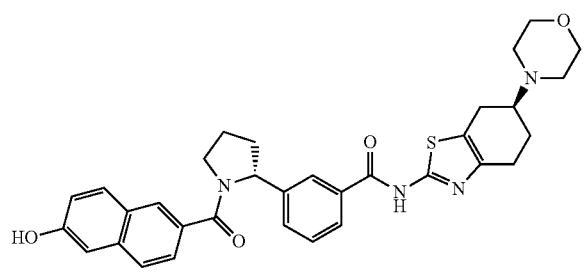
131
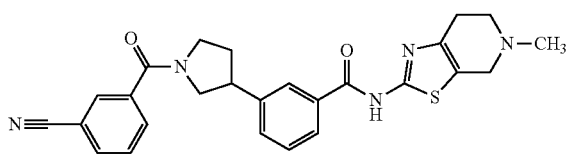
132
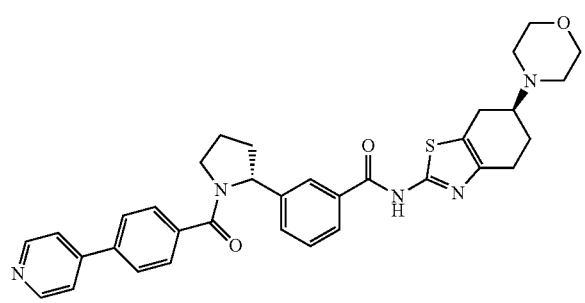
133
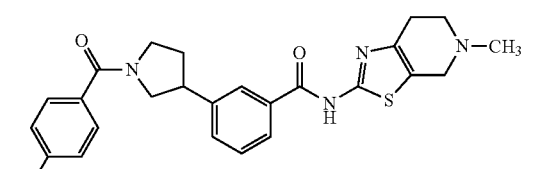
134
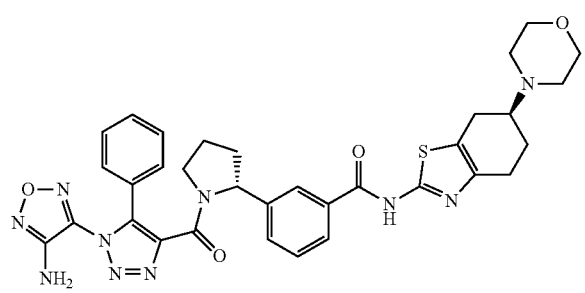
135
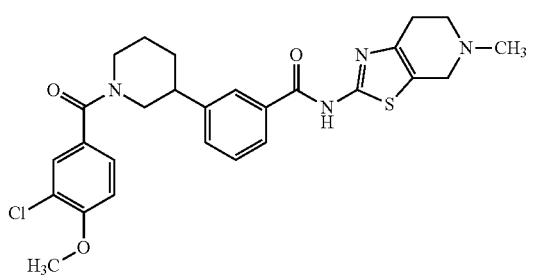

-continued
136
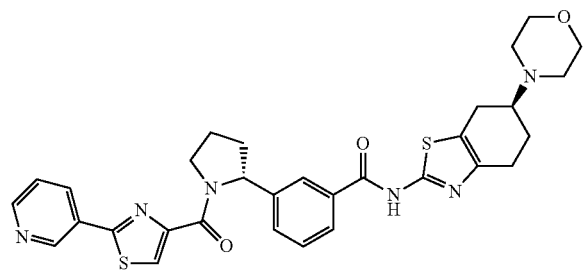
137
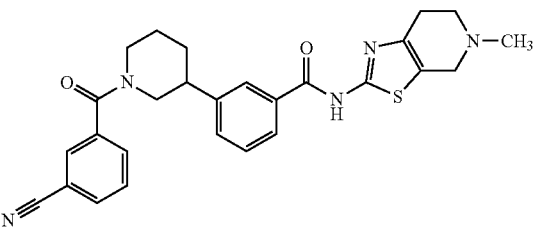
138
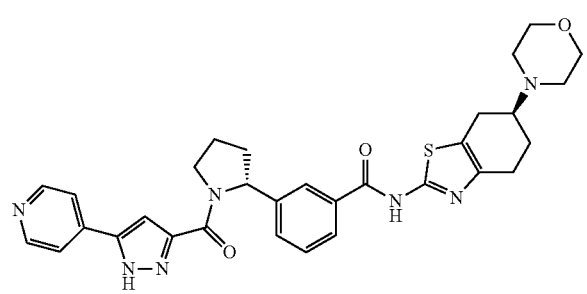
139
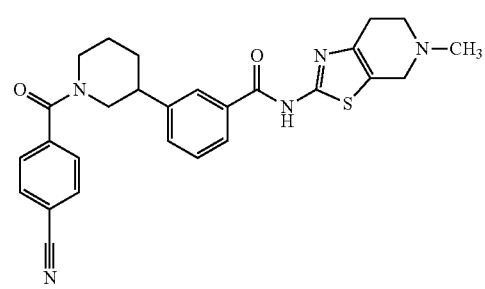
140
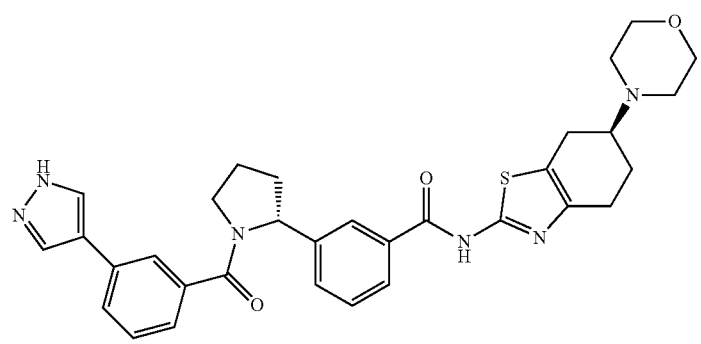
142
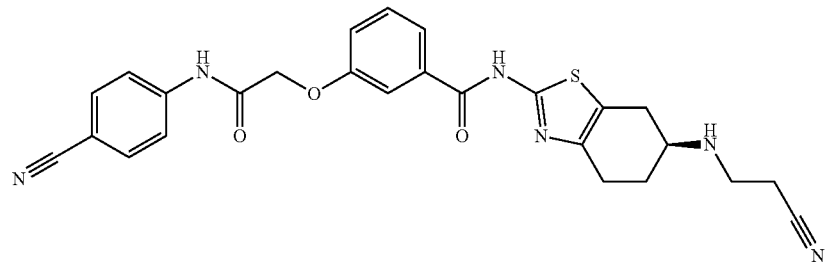
144
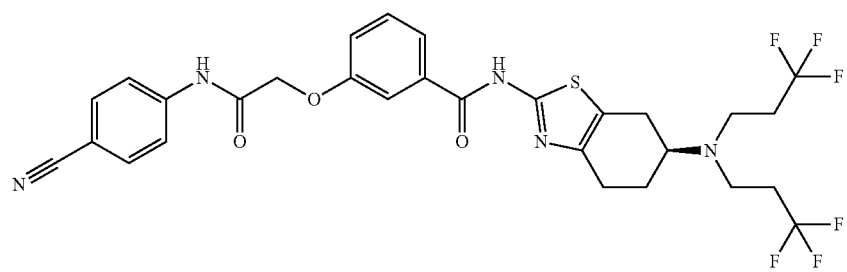

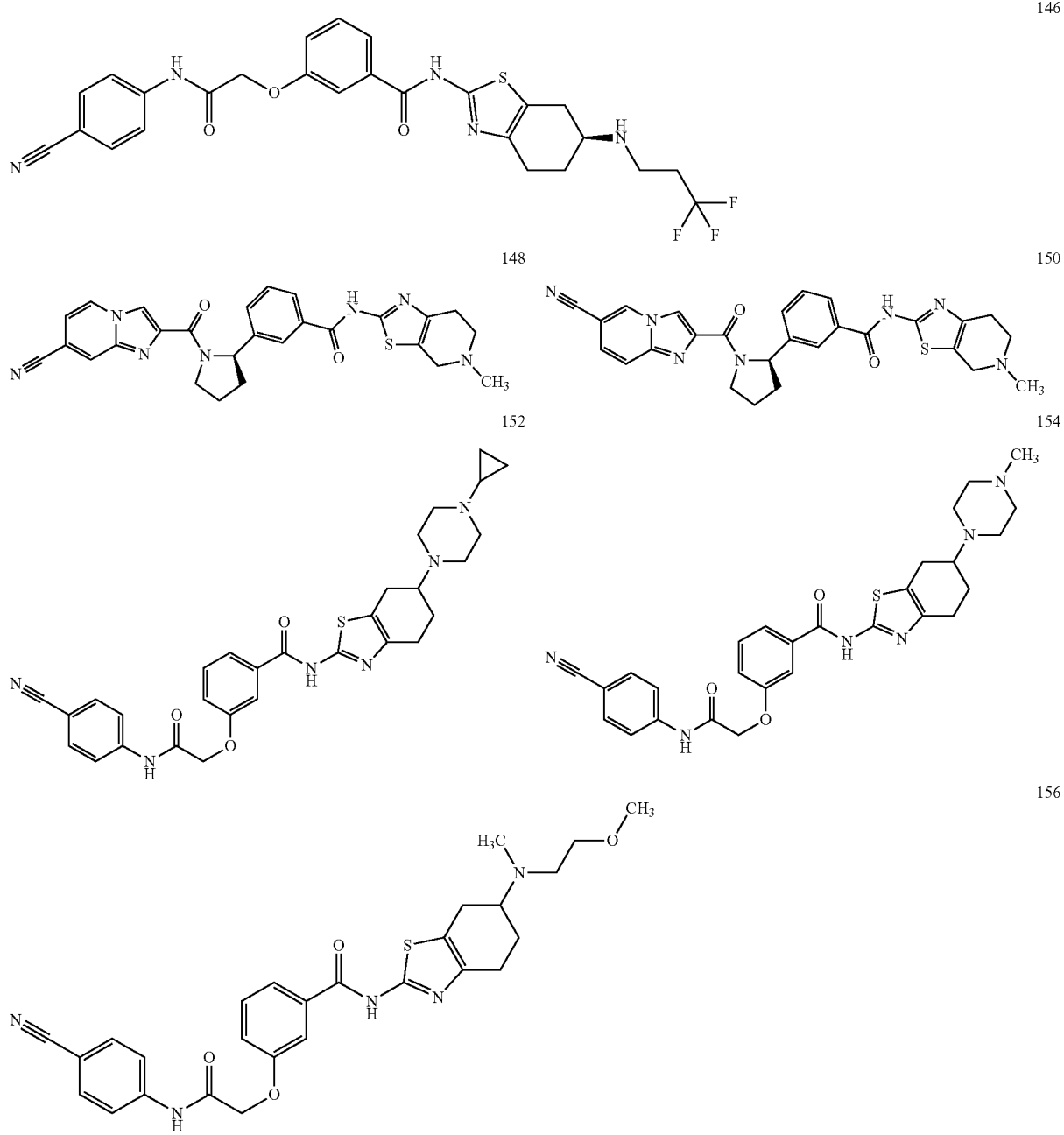
and the pharmaceutically acceptable salts thereof.
10. The compound of claim 9 selected from the group consisting of compound number 1, 5, 9, 11, 13, 15, 18-24, 26, 28-30, 32, 34, 36-40, 42, 44, 46-48, 50, 52-61, 66, 70, 74, 77, 78, 82, 84, 86, 88, 90, 92, 94, 96, 100-102, 104-106, 108-112, 114-118, 120, 122, 124, 126, 128, 130, 132, 134, 136, 138, 140, 142, 146, 148, 150, 152, 154 and 156, or the pharmaceutically acceptable salt thereof.
11. A pharmaceutical composition comprising the compound of claim 1 and a pharmaceutically acceptable excipient or carrier.
* * * * *